(12) United States Patent
Kim et al.

(10) Patent No.: US 9,994,618 B2
(45) Date of Patent: Jun. 12, 2018

(54) HIGH EFFICIENCY METHOD FOR PURIFYING HUMAN PAPILLOMAVIRUS VIRUS-LIKE PARTICLES

(71) Applicant: Hong-Jin Kim, Seoul (KR)

(72) Inventors: Hong-Jin Kim, Seoul (KR); Hyoung Jin Kim, Seoul (KR)

(73) Assignee: Hong-Jin Kim, Seoul (KR)

( * ) Notice: Subject to any disclaimer, the term of this patent is extended or adjusted under 35 U.S.C. 154(b) by 164 days.

(21) Appl. No.: 14/418,004

(22) PCT Filed: Jul. 30, 2013

(86) PCT No.: PCT/KR2013/006823
§ 371 (c)(1),
(2) Date: Jan. 28, 2015

(87) PCT Pub. No.: WO2014/021604
PCT Pub. Date: Feb. 6, 2014

(65) Prior Publication Data
US 2015/0266927 A1  Sep. 24, 2015

(30) Foreign Application Priority Data

Jul. 30, 2012 (KR) .................. 10-2012-0083472
Jul. 19, 2013 (KR) .................. 10-2013-0085605

(51) Int. Cl.
| | |
|---|---|
| C07K 14/005 | (2006.01) |
| C07K 14/025 | (2006.01) |
| C12N 7/00 | (2006.01) |
| C12N 7/02 | (2006.01) |
| A61K 39/00 | (2006.01) |
| A61K 39/12 | (2006.01) |

(52) U.S. Cl.
CPC .............. *C07K 14/005* (2013.01); *C12N 7/00* (2013.01); *A61K 39/00* (2013.01); *C12N 2710/20034* (2013.01); *C12N 2710/20051* (2013.01)

(58) Field of Classification Search
None
See application file for complete search history.

(56) References Cited

U.S. PATENT DOCUMENTS

| 6,602,697 B1 | 8/2003 | Cook, III |
| 7,351,533 B2 | 4/2008 | McCarthy et al. |

FOREIGN PATENT DOCUMENTS

| CN | 101139570 A | 3/2008 |
|---|---|---|
| CN | 101153280 A | 4/2008 |
| EP | 2 154 148 A1 | 2/2010 |
| JP | 2001-515922 A | 9/2001 |
| JP | 2002-540167 A | 11/2002 |
| KR | 2001-0072470 A | 7/2001 |
| KR | 10-0959145 B1 | 5/2010 |
| KR | 10-2011-0009249 A | 1/2011 |
| KR | 10-2011-0053340 A | 5/2011 |
| KR | 10-1178056 B1 | 8/2012 |
| KR | 10-1181907 B1 | 9/2012 |
| WO | 99/13056 A1 | 3/1999 |
| WO | 00/57906 A1 | 10/2000 |
| WO | 01/28585 A1 | 4/2001 |
| WO | 01/42780 A1 | 6/2001 |
| WO | 2010/147268 A1 | 12/2010 |

OTHER PUBLICATIONS

Buck, C.B., et al. 2005 Journal of Virology 79(5): 2839-2846.*
Woodman et al., "The natural history of cervical HPV infection: unresolved issues", Nat Rev Cancer 7: 11-22, (2007).
"Women's Health Report, Fiscal Years 2005-2006", National Cancer Institute (2007).
Burk et al., "Human Papillomaviruses: Genetic Basis of Carcinogenicity", Public Health Genomics, vol. 12, pp. 281-290, (2009).
De Villiers et al., "Classification of papillomaviruses", Virology, vol. 324, pp. 17-27, (2004).
Clifford et al., "Chapter 3: HPV type-distribution in women with and without cervical neoplastic diseases", Vaccine, vol. 24, Suppl. 3, pp. S3/26-S3/34, (2006).
Conway et al., "Replication and assembly of human papillomaviruses", J Dent Res, vol. 88, pp. 307-317, (2009).
Kim et al., "Purification and immunogenicity study of human papillomavirus type 16 L1 protein in *Saccharomyces cerevisiae*", J Virol Methods, vol. 139, pp. 24-30, (2007).
Li et al., "Expression of the human papillomavirus type 11 L1 capsid protein in *Escherichia coli*: characterization of protein domains involved in DNA binding and capsid assembly", J Virol, vol. 71, pp. 2988-2995, (1997).
Rao et al., "Expression of codon optimized major capsid protein (L1) of human papillomavirus type 16 and 18 in Pichia pastoris; purification and characterization of the virus-like particles", Vaccine, vol. 29, pp. 7326-7334, (2011).
Aires et al., "Production of human papillomavirus type 16 L1 virus-like particles by recombinant Lactobacillus casei cells", Appl Environ Microbiol, vol. 72, pp. 745-752, (2006).
Baek et al., "Production and purification of human papillomavirus type 33 L1 virus-like particles from Spodoptera frugiperda 9 cells using two-step column chromatography", Protein Expr Purif, vol. 75, pp. 211-217, (2011).
MacLean et al., "Optimization of human papillomavirus type 16 (HPV-16) L1 expression in plants: comparison of the suitability of different HPV-16 L1 gene variants and different cell-compartment localization", J Gen Virol, vol. 88, pp. 1460-1469, (2007).
Garland et al., "Human papillomavirus vaccines: current status and future prospects", Drugs, vol. 70, pp. 1079-1098, (2010).
Madrid-Marina et al., "Advantages and disadvantages of current prophylactic vaccines against HPV", Arch Med Res, vol. 40, pp. 471-477, (2009).

(Continued)

*Primary Examiner* — Marsha Tsay
(74) *Attorney, Agent, or Firm* — Vorys, Sater, Seymour and Pease LLP; Mih Suhn Koh

(57) ABSTRACT

Provided is a method of purifying human papillomavirus (HPV) L1 proteins with high purity and high efficiency. According to the purification method, a purification purity and yield of HPV L1 proteins can be considerably increased when heating/chilling is formed by treating a cell homogenate with a reducing agent. In addition, VLPs of the HPV L1 protein purified by the purification method have excellent antigenicity and immunogenicity.

10 Claims, 38 Drawing Sheets

(56) References Cited

OTHER PUBLICATIONS

National Cancer Institute Human Papillomavirus (HPV) Vaccines, http://www.cancer.gov/cancertopics/factsheet/prevention/HPV-vaccine, eight pages (2011).
Mukhopadhyay et al., "Introducing HPV Vaccine in Developing Countries—Addressing the Challenge", Indian J Community Med, vol. 34, pp. 370-371, (2009).
Walsh, "Biopharmaceutical benchmarks 2010", Nat Biotechnol, vol. 28, pp. 917-924, (2010).
Vicente et al., "Large-scale production and purification of VLP-based vaccines", J Invertebr Pathol, vol. 107, Suppl, pp. S42-S48, (2011).
Hofmann et al., "Sequence determination of human papillomavirus type 6a and assembly of virus-like particles in *Saccharomyces cerevisiae*", Virology, vol. 209, pp. 506-518, (1995).
Park et al., "Optimum conditions for production and purification of human papillomavirus type 16 L1 protein from *Saccharomyces cerevisiae*", Protein Expr Purif, vol. 59, pp. 175-181, (2008).
Kim et al., "One-step chromatographic purification of human papillomavirus type 16 L1 protein from *Saccharomyces cerevisiae*", Protein Expr Purif, vol. 70, pp. 68-74, (2010).
Kim et al., "Optimizing the secondary structure of human papillomavirus type 16 L1 mRNA enhances L1 protein expression in *Saccharomyces cerevisiae*", J Biotechnol, vol. 150, pp. 31-36, (2010).
Kim et al., "A method for removing contaminating protein during purification of human papillomavirus type 18 L1 protein from *Saccharomyces cerevisiae*", Arch Pharm Res, vol. 32, pp. 1759-1766, (2009).
Kim et al., "The composition of the carbon source and the time of cell harvest are critical determinants of the final yield of human papillomavirus type 16 L1 protein produced in *Saccharomyces cerevisiae*", Protein Expr Purif, vol. 80, pp. 52-60, (2011).
Kim et al., "The choice of resin-bound ligand affects the structure and immunogenicity of column-purified human papillomavirus type 16 virus-like particles", PLoS One, vol. 7, p. e35893, (2012).
Jin et al., "A single serum dilution enzyme-linked immunosorbent assay for determining anti-human papillomavirus (HPV) antibody titres in humans immunised with prophylactic HPV vaccines", J Pharm Biomed Anal, vol. 66, pp. 352-355, (2012).
Han et al., "Comparison of the immune responses to the CIA06-adjuvanted human papillomavirus L1 VLP vaccine with those against the licensed HPV vaccine Cervarix in mice", Vaccine, vol. 30, pp. 4127-4134, (2012).
Hagensee et al., "Three-dimensional structure of vaccinia virus-produced human papillomavirus type 1 capsids", J Virol, vol. 68, pp. 4503-4505, (1994).
Baker et al., "Structures of bovine and human papillomaviruses. Analysis by cryoelectron microscopy and three-dimensional image reconstruction", Biophys J, vol. 60, pp. 1445-1456, (1991).
Shi et al., "Stabilization of human papillomavirus virus-like particles by non-ionic surfactants", J Pharm Sci, vol. 94, pp. 1538-1551, (2005).
Ryding et al., "Deletion of a major neutralizing epitope of human papillomavirus type 16 virus-like particles", J Gen Virol, vol. 88, pp. 792-802, (2007).
Culp et al., "Binding and neutralization efficiencies of monoclonal antibodies, Fab fragments, and scFv specific for L1 epitopes on the capsid of infectious HPV particles", Virology, vol. 361, pp. 435-446, (2007).
White et al., "Characterization of a major neutralizing epitope on human papillomavirus type 16 L1", J Virol, vol. 73, pp. 4882-4889, (1999).
Laemmli, "Cleavage of structural proteins during the assembly of the head of bacteriophage T4", Nature, vol. 227, pp. 680-685, (1970).
Chang et al., "Effects of downstream processing on structural integrity and immunogenicity in the manufacture of papillomavirus type 16 L1 virus-like particles", Biotechnol Bioprocess Eng, vol. 17, pp. 755-763, (2012).
International Search Report for PCT/KR2013/006823, three pages, dated Oct. 18, 2013.
Yuan et al., "Reversed-phase high-performance liquid chromatography of virus-like particles", Journal of Chromatography A, vol. 816, pp. 21-28, (1998).
Zhang et al., "Expression of Human Papillomavirus Type 16 L1 Protein in *Escherichia coli*: Denaturation, Renaturation, and Self-Assembly of Virus-like Particles in Vitro", Virology, vol. 243, pp. 423-431, (1998).
Extended European search report, for EP Application No. 13824788, 11 pages, dated Mar. 10, 2016.

\* cited by examiner (A)

| | 2.5 μL loading | | 1.2 μL loading | |
|---|---|---|---|---|
| | H only | HC | H only | HC |
| Protein 1 | 31691 | 16784 | 18913 | 14335 |
| Protein 2 | 32788 | 16133 | 12248 | 7413 |
| Protein 3 | 33943 | 18877 | 20739 | 9327 |

HPV18 L1 VLP (88 ± 0.2 nm)

FIG. 36

HPV16 L1 NG2

```
   1 atgtcgttat ggttaccttc agaagctacc gtttatcttc ctccagtacc agtttccaaa
  61 gtcgtttcta cagatgaata cgttgctaga actaacattt actaccatgc aggcacttcc
 121 aggttattag ctgtcggtca tccctattc ccaattaaaa agcccaacaa taataagata
 181 ttagttccaa agtttccgg cttacaatac agagtcttta gaatacattt accagatcct
 241 aataaatttg gttttccaga tactttcttt tataatccag atactcaaag attggttttg
 301 gcttgtgttg gtgttgaagt tggtagaggt caaccattgg gtgttggtat ttctgtcat
 361 ccaattgtga ataaattgga tgatactgaa aatgcttctg cttatgctgc taatgctggt
 421 gttgataata gagaatgtat ttctatggat tataaacaaa ctcaattgtg tttgattggt
 481 tgtaaaccac caattggtga acattggggt aaaggtctc catgtactaa tgttgctgtt
 541 aatccaggtg atgtccacc attggaattg actaatactc ttattcaaga tggtgatatg
 601 gttgatactg gttttggtgc tatgaatttt actactttgc aagctaataa atctgaagtt
 661 ccattggata tttgtacttc tatttgtaaa tatccagatt atattaaaat ggtttctgaa
 721 ccatatggtg atcttcttgt ttttatttg agaagagaac aatgttgt tagacatttg
 781 tttaatagag ctgtgctgt tgtgaaaat gttccagatg atttgtatat taaaggttct
 841 ggttctactg ctaattggc ttcttctaat tattttccaa ctccatctgg ttctatgctt
 901 acttctgatg ctcaaatttt taataaacca tattgttgc aaagagctca agtcataat
 961 aatggtattt gttgggtaa tcaattgttt gttactgttg ttgatactac tagatctact
1021 aatatgtctt tgtgtgctgc tatttctact tctgaaacta tattttcta tactaatttt
1081 aaagaatatt tgagacatgg tgaagaatat gatttgcaat gattgtaaa attgtgtaaa
1141 ataactttaa ctgcagacgt aatgacttat attcactcac tgaacttcac aatactagaa
1201 gactggaatt tcggtttaca acccccaccc ggaggaacac tggaagacac ttatagattc
1261 gttacttcac aagctattgc ctgtcaaaaa catacccctc ctgccccaa agaagatcct
1321 ctaaaaaat acacattctg ggaagttaat ttaaaagaaa aatttctcagc agacttagat
1381 caattccat ctgaagaaa atttttatta caagcaggtt tgaaggctaa accaaaattt
1441 actttaggaa aagaaaagc acacccctaca acctcatcaa cctcaacaac tgctaaaaga
1501 aaaaaagaa aattataa
```

FIG. 37

```
HPV18 L1 NG3
   1 atggctttat ggagaccatc ggataacaca gtttacctic cccccccaag tgtcgcaagg
  61 gttgttaata ctgatgatta tgttactaga actictatit tttatcatgc tgttcttcet
 121 agattgttga ctgttgtaa tccatatttt agagttccag ctggtggtgg taataaacaa
 181 gatattccaa agttictgc ttatcaatat agagtitta gagticaatt gccagatcca
 241 ataaaatitg gtttgccaga tactictatt tatctictatt aaactcaaag attgttigg
 301 gctgtgctg gtgttgaaat tggtagaggt caaccattgg gtgttggttt gtctggtcat
 361 ccattttata ataaattgga tgatactgaa tcttctcatg ctgctactc taatgtttct
 421 gaagatgtta gagataatgt ttctgttgat tataacaaa ctcaattgt tatttgggt
 481 tgtgctccag ctattggtga acattgggct aaagtactg cttgtaaatc tagaccattg
 541 tctcaaggtg atgtccacc attggaattg aaaaatactg ttttggaaga tggtgatatg
 601 gttgatactg gtatggtgc tatgdatttt tacacttgc aagatactaa atgtgagtt
 661 ccattggata tttgtcaatc tatttgtaaa tatccagatt atttgcaaat gtctgctgat
 721 ccatatgtg atctatgtt tttttgttg agagagaaac aattgtttgc tagacattc
 781 tggaatagag ctgtactact gggtgatact gttccacaat cttgtatat taaagtact
 841 ggtatgagag cttcccagg ttctgtgtt tattctccat ctcatcgg ttctattgtt
 901 acttctgatt ctcaattgtt taataaacca tatggtgtgc ataagtca agtcataat
 961 aatggtgtt gttggcataa tcaattgttt gttactgttg ttgatactac tagatctact
1021 aatttgacta ttctgtcctc tactcaatct ccagtcccag gtcaatatga tgctactaaa
1081 tttaaacaat attctagaca tgttgaagaa tatgatttgc aatttattt tcaattgtgt
1141 actattactt tgactgctga tgtatgtct tatattcatt ctatgaattc ttctatttg
1201 gaagattgga attttggtgt tccaccacca ccaactactt cttggttga tacttataga
1261 tttgttcaat ctgttgctat tacttgtcaa aaagatgctg ctccagtga aaataaagat
1321 ccatatgata aattgaatt ttggaatgtt gattgaag gtttgaaag tttgatttg
1381 gatcaatatc cattgggtag aaaattttg gttcaagctg gtttgagaag aaaaccaact
1441 attggtccaa gaaaaagatc tgctccatct gctactactt ctctaaacc agctaaaaga
1501 gtcagagtaa gagcaagaaa ataa
```

FIG. 38

<HPV16 L1>

MSLWLPSEATVYLPPVPVSKVVSTDEYVARTNIYYHAGTSRLLAVGHPYFPIKKPNNNKI 60
LVPKVSGLQYRVFRIHLPDPNKFGFPDTSFYNPDTQRLVWACVGVEVGRGQPLGVGISGH 120
PLLNKLDDTENASAYAANAGVDNRECISMDYKQTQLCLIGCKPPIGEHWGKGSPCTNVAV 180
NPGDCPPLELINTVIQDGDMVDTGFGAMDFTTLQANKSEVPLDICTSICKYPDYIKMVSE 240
PYGDSLFFYLRREQMFVRHLFNRAGAVGENWPDDLYIKGSGSTANLASSNYFTTPSGSMV 300
TSDAQIFNKPYWLQRAQGHNNGICWGNQLFVTVVDTTRSTNMSLCAAISTSETTYKNTNF 360
KEYLRHGEEYDLQFIFQLCKITLTADVMTYIHSMNSTILEDWNFGLQPPPGGTLEDTYRF 420
VTSQAIACQKHTPPAPKEDPLKKYTFWEVNLKEKFSADLDQFPLGRKFLLQAGLKAKPKF 480
TLGKRKATPTTSSTSTTAKRKKRKL (taa) 505

<HPV18 L1>

MALWRPSDNTVYLPPPSVARVVNTDDYVTRTSIFYHAGSSRLLTVGNPYFRVPAGGGNKQ 60
DIPKVSAYQYRVFRVQLPDPNKFGLPDTSIYNPETQRLVWACAGVEIGRGQPLGVGLSGH 120
PFTNKLDDTESSHAATSNVSEDVRDNVSVDYKQTQLCLIGCARPAIGEHWAKGTACKSRPL 180
SQGDCPELELKNTVLEDGDMVDTGYGAMDFSTLQDTKCEVPLDICQSICKYPDYLQMSAD 240
PYGDSMFFCLRREQLFARHFWNRAGTMGDTVPQSLYIKGTGMRASPGSSCVYSPSPSGSIV 300
TSDSQLFNKPYWLHKAQGHNNGVCWHNQLFVTVVDTTRSTNLTICASTQSPVPGQYDATK 360
FKQISHVEYDLQFIFQLCTITLTPADVMSYIHSMNSSILEDWNFGVPPPTTSLVDTYR 420
FVQSVAITCQKDAAPAENKDPYDKLKFWNVDLKEKFSLDLDQYPLGRKFLVQAGLRRKPT 480
IGPRKRSAPSAITSSKPAKRVRVRARK (taa) 507

SEQUENCE LISTING

<160> NUMBER OF SEQ ID NOS: 4

<210> SEQ ID NO 1
<211> LENGTH: 1518
<212> TYPE: DNA
<213> ORGANISM: HPV16 L1 NG2

<400> SEQUENCE: 1

```
atgtcgttat ggttaccttc agaagctacc gtttatcttc ctccagtacc agtttccaaa      60
gtcgtttcta cagatgaata cgttgctaga actaacattt actaccatgc aggcacttcc     120
aggttattag ctgtcggtca tccctatttc ccaattaaaa agcccaacaa taataagata     180
ttagttccaa aagtttccgg cttacaatac agagtcttta gaatacattt accagatcct     240
aataaatttg gttttccaga tacttctttt tataatccag atactcaaag attggtttgg     300
gcttgtgttg gtgttgaagt tggtagaggt caaccattgg gtgttggtat ttctggtcat     360
ccattgttga ataaattgga tgatactgaa atgcttctg cttatgctgc taatgctggt     420
gttgataata gagaatgtat ttctatggat tataaacaaa ctcaattgtg tttgattggt     480
tgtaaaccac caattggtga acattggggt aaaggttctc catgtactaa tgttgctgtt     540
aatccaggtg attgtccacc attggaattg attaatactg ttattcaaga tggtgatatg     600
gttgatactg gttttggtgc tatggatttt actactttgc aagctaataa atctgaagtt     660
ccattggata tttgtacttc tatttgtaaa tatccagatt atattaaaat ggtttctgaa     720
ccatatggtg attctttgtt ttttatttg agaagagaac aaatgtttgt tagacatttg     780
tttaatagag ctggtgctgt tggtgaaaat gttccagatg atttgtatat taaaggttct     840
ggttctactg ctaatttggc ttcttctaat tattttccaa ctccatctgg ttctatggtt     900
acttctgatg ctcaaatttt taataaacca tattggttgc aaagagctca aggtcataat     960
aatggtattt gttggggtaa tcaattgttt gttactgttg ttgatactac tagatctact    1020
aatatgtctt gtgtgctgc tatttctact tctgaaacta cttataaaaa tactaatttt    1080
aaagaatatt tgagacatgg tgaagaatat gatttgcaat ttatttttca attgtgtaaa    1140
ataactttaa ctgcagacgt aatgacttat attcactcaa tgaactccac aatactagaa    1200
gactggaatt tcggtttaca accccacccc ggaggaacac tggaagacac ttatagattc    1260
gttacttcac aagctattgc ctgtcaaaaa catacccctc ctgccccaa agaagatcct    1320
ctaaaaaat acacattctg ggaagttaat ttaaaagaaa aattctcagc agacttagat    1380
caatttccat tgggaagaaa attttttatta caagcaggtt tgaaggctaa accaaaattt    1440
actttaggaa aagaaaagc aacacctaca acctcatcaa cctcaacaac tgctaaaaga    1500
```
aaaaaaagaa aattataa                                                    1518

<210> SEQ ID NO 2
<211> LENGTH: 1524
<212> TYPE: DNA
<213> ORGANISM: HPV18 L1 NG3

<400> SEQUENCE: 2
atggctttat ggagaccatc ggataacaca gtttaccttc cccccccaag tgtcgcaagg      60
gttgttaata ctgatgatta tgttactaga acttctattt tttatcatgc tggttcttct     120
agattgttga ctgttggtaa tccatatttt agagttccag ctggtggtgg taataaacaa     180
gatattccaa aagtttctgc ttatcaatat agagttttta gagttcaatt gccagatcca     240
aataaatttg gtttgccaga tacttctatt tataatccag aaactcaaag attggtttgg     300
gcttgtgctg tgttgaaat tggtagaggt caaccattgg gtgttggttt gtctggtcat     360
ccatttttata ataaattgga tgatactgaa tcttctcatg ctgctacttc taatgtttct     420
gaagatgtta gagataatgt ttctgttgat tataaacaaa ctcaattgtg tattttgggt     480
tgtgctccag ctattggtga acattgggct aaaggtactg cttgtaaatc tagaccattg     540
tctcaaggtg attgtccacc attggaattg aaaaatactg ttttggaaga tggtgatatg     600
gttgatactg gttatggtgc tatggatttt tctactttgc aagatactaa atgtgaagtt     660
ccattggata tttgtcaatc tatttgtaaa tatccagatt atttgcaaat gtctgctgat     720
ccatatggtg attctatgtt tttttgtttg agaagagaac aattgttgtc tagacatttt     780
tggaatagag ctggtactat gggtgatact gttccacaat ctttgtatat taaaggtact     840
ggtatgagag cttctccagg ttcttgtgtt tattctccat ctccatctgg ttctattgtt     900
acttctgatt ctcaattgtt taataaacca tattggttgc ataaagctca aggtcataat     960
aatggtgttt gttggcataa tcaattgttt gttactgttg ttgatactac tagatctact    1020
aatttgacta tttgtgcttc tactcaatct ccagttccag tcaatatga tgctactaaa    1080
tttaaacaat attctagaca tgttgaagaa tatgatttgc aatttatttt tcaattgtgt    1140
actattactt tgactgctga tgttatgtct tatattcatt ctatgaattc ttctatttg    1200
gaagattgga attttggtgt tccaccacca ccaactactt cttttggttga tacttataga    1260
tttgttcaat ctgttgctat tacttgtcaa aaagatgctg ctccagctga aaataaagat    1320
ccatatgata aattgaaatt ttggaatgtt gatttgaaag aaaaattttc tttggatttg    1380
gatcaatatc cattgggtag aaaattttg gttcaagctg gttgagaag aaaaccaact    1440
attggtccaa gaaaagatc tgctccatct gctactactt cttctaaacc agctaaaaga    1500
gtcagagtaa gagcaagaaa ataa                                           1524

<210> SEQ ID NO 3
<211> LENGTH: 505
<212> TYPE: PRT
<213> ORGANISM: HPV16 L1

<400> SEQUENCE: 3

Met Ser Leu Trp Leu Pro Ser Glu Ala Thr Val Tyr Leu Pro Pro Val
 1               5                  10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

```
Tyr Phe Pro Ile Lys Lys Pro Asn Asn Asn Lys Ile Leu Val Pro Lys
 50                  55                  60

Val Ser Gly Leu Gln Tyr Arg Val Phe Arg Ile His Leu Pro Asp Pro
 65                  70                  75                  80

Asn Lys Phe Gly Phe Pro Asp Thr Ser Phe Tyr Asn Pro Asp Thr Gln
                 85                  90                  95

Arg Leu Val Trp Ala Cys Val Gly Val Glu Val Gly Arg Gly Gln Pro
                100                 105                 110

Leu Gly Val Gly Ile Ser Gly His Pro Leu Leu Asn Lys Leu Asp Asp
            115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
            195                 200                 205

Asp Phe Thr Thr Leu Gln Ala Asn Lys Ser Glu Val Pro Leu Asp Ile
210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
            290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
```

```
                465                 470                 475                 480
Thr Leu Gly Lys Arg Lys Ala Thr Pro Thr Thr Ser Thr Ser Thr
                        485                 490                 495

Thr Ala Lys Arg Lys Lys Arg Lys Leu
            500                 505

<210> SEQ ID NO 4
<211> LENGTH: 507
<212> TYPE: PRT
<213> ORGANISM: HPV18 L1

<400> SEQUENCE: 4

Met Ala Leu Trp Arg Pro Ser Asp Asn Thr Val Tyr Leu Pro Pro
 1               5                  10                  15

Ser Val Ala Arg Val Val Asn Thr Asp Asp Tyr Val Thr Arg Thr Ser
                20                  25                  30

Ile Phe Tyr His Ala Gly Ser Ser Arg Leu Leu Thr Val Gly Asn Pro
                35                  40                  45

Tyr Phe Arg Val Pro Ala Gly Gly Asn Lys Gln Asp Ile Pro Lys
         50                  55                  60

Val Ser Ala Tyr Gln Tyr Arg Val Phe Arg Val Gln Leu Pro Asp Pro
 65                  70                  75                  80

Asn Lys Phe Gly Leu Pro Asp Thr Ser Ile Tyr Asn Pro Glu Thr Gln
                85                  90                  95

Arg Leu Val Trp Ala Cys Ala Gly Val Glu Ile Gly Arg Gly Gln Pro
                100                 105                 110

Leu Gly Val Gly Leu Ser Gly His Pro Phe Tyr Asn Lys Leu Asp Asp
            115                 120                 125

Thr Glu Ser Ser His Ala Ala Thr Ser Asn Val Ser Glu Asp Val Arg
            130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
            180                 185                 190

Thr Val Leu Glu Asp Gly Asp Met Val Asp Thr Gly Tyr Gly Ala Met
            195                 200                 205

Asp Phe Ser Thr Leu Gln Asp Thr Lys Cys Glu Val Pro Leu Asp Ile
        210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
                260                 265                 270

Gln Ser Leu Tyr Ile Lys Gly Thr Gly Met Arg Ala Ser Pro Gly Ser
            275                 280                 285

Cys Val Tyr Ser Pro Ser Pro Ser Gly Ser Ile Val Thr Ser Asp Ser
        290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335
```

```
Thr Arg Ser Thr Asn Leu Thr Ile Cys Ala Ser Thr Gln Ser Pro Val
            340                 345                 350

Pro Gly Gln Tyr Asp Ala Thr Lys Phe Lys Gln Tyr Ser Arg His Val
            355                 360                 365

Glu Glu Tyr Asp Leu Gln Phe Ile Phe Gln Leu Cys Thr Ile Thr Leu
    370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Thr Thr Ser Leu Val
            405                 410                 415

Asp Thr Tyr Arg Phe Val Gln Ser Val Ala Ile Thr Cys Gln Lys Asp
            420                 425                 430

Ala Ala Pro Ala Glu Asn Lys Asp Pro Tyr Asp Lys Leu Lys Phe Trp
            435                 440                 445

Asn Val Asp Leu Lys Glu Lys Phe Ser Leu Asp Leu Asp Gln Tyr Pro
        450                 455                 460

Leu Gly Arg Lys Phe Leu Val Gln Ala Gly Leu Arg Arg Lys Pro Thr
465                 470                 475                 480

Ile Gly Pro Arg Lys Arg Ser Ala Pro Ser Ala Thr Thr Ser Ser Lys
            485                 490                 495

Pro Ala Lys Arg Val Arg Val Arg Ala Arg Lys
            500                 505
```

HIGH EFFICIENCY METHOD FOR PURIFYING HUMAN PAPILLOMAVIRUS VIRUS-LIKE PARTICLES

The Sequence Listing submitted in text format (.txt) filed on May 4, 2015, named "SequenceListing.txt", created on Apr. 28, 2015, 12.1 KB), is incorporated herein by reference.

TECHNICAL FIELD

The present invention relates to a method of purifying virus-like particles (VLPs) of human papillomavirus (HPV) having excellent structural and immunological characteristics with high efficiency.

BACKGROUND ART

HPV is a pathogen causing approximately 100% of cervical cancer cases [1]. It is reported that, annually, 500,000 women are diagnosed with cervical cancer around the world, and 250,000 women die from cervical cancer [2]. Types 16, 18, 45, 31, 33, 52, 58, 35, and 59 are known as high risk types of HPV that cause cervical cancer, whereas types 6 and 11 are known as low risk types of HPV [3,4]. In particular, HPV16 and HPV18 are known to cause 70% of all cervical cancer cases, and thus are recognized as the most important types in prevention of cervical cancer [5]. Types of HPVs causing cervical cancer vary by region [5]. In Africa, Europe, North America and Central and South America, HPV16, HPV18, HPV31 and HPV45 infections are main causes of cervical cancer, and in Asia, HPV16, HPV18, HPV58 and HPV33 infections are main causes of cervical cancer [5].

A capsid of HPV is composed of L1 protein as a major antigen and L2 protein as a minor antigen [6]. Here, the L1 protein has been used as an antigen for prophylactic vaccine of cervical cancer and an antigen for diagnosis because it has a property of self-assembly that forming virus-like particles (VLPs) [6, 27]. Recombinant L1 protein was produced in *Escherichia coli, Saccharomyces cerevisiae, Pichia Pastoris, Lactobacillus casei*, or *Spodoptera frugiperda* (Sf) cells, or plant cells as expression cells [7-12, 28]. Today, commercially available cervical cancer vaccines are Gardasil™ (Merck) and Cervarix™ (GlaxosmithKline, GSK). Gardasil™ includes L1 VLPs with respect to HPV16, HPV18, HPV6 and HPV11 as antigens, and Cervarix™ includes L1 VLPs with respect to HPV16 and HPV18 as antigens [13]. Gardasil™ uses *Saccharomyces cerevisiae* as an antigen-expressing cell, and Cervarix™ uses *Spodoptera frugiperda* (Sf) cells, which are insect cells, as antigen-expressing cells [13,14]. Both of the two vaccines are injected by intramuscular injection, and have high costs of $120 for one dose and $360 for three doses [15]. Due to the high injection costs of the commercially available cervical cancer vaccines, the vaccines have many limits to be widely used in a developing country, which is a region in which cervical cancer mainly occurs [16]. Accordingly, development of a low-cost and highly-effective cervical cancer vaccine still remains an important issue.

In the case of a drug using recombinant protein, a cost for downstream processing is as high as 80% of the total production cost [17]. To produce an antigen for the cervical cancer vaccine, a method of sequentially increasing purity of a target antigen through several steps of purification in the downstream processing is used [18]. In the case of VLPs produced in *Saccharomyces cerevisiae*, to increase the purity of the target protein, sucrose cushion using ultracentrifugation or size-exclusion chromatography has been mainly used. To purify VLPs, Hofmann et al. used a sucrose cushion using ultracentrifugation, anion exchange chromatography, ammonium sulfate precipitation and size-exclusion chromatography [19]. Kim et al. sequentially used a sucrose cushion using ultracentrifugation, size-exclusion chromatography and cation exchange chromatography to purify the VLPs [7]. Park et al. used a purification method including ammonium sulfate precipitation, size-exclusion chromatography, and cation exchange chromatography, which were sequentially performed [20]. According to the methods, high purity VLPs may be obtained, but the methods have a limit in increasing a purification unit, and are not suitable to be applied in large scale production.

For large scale production of VLPs of HPV produced from *Saccharomyces cerevisiae*, the following methods were used. Cook et al. used a method of sequentially using cross-flow microfiltration, cation exchange chromatography, and hydroxyapatite chromatography [21]. Kim et al. used a method of purifying VLPs through heparin chromatography or cation exchange chromatography after foreign proteins were removed by ammonium sulfate precipitation and step removing precipitated contaminants [22]. A HPV L1 protein produced from *Saccharomyces cerevisiae* numbers no more than 1% of all known homogenate proteins, and recovery of that is not easy [20]. To purify HPV VLPs produced by a method of preparing a recombinant protein with high purity, several steps of precipitation and chromatography should be performed, and repeated dialysis is also needed. In addition, since the VLPs of HPV are easily disrupted, assembly of the VLPs in an excellent structure is considered to be very important [31]. While researchers have made a lot of effort to develop a process of effectively removing a foreign substance in a homogenate of a host cell such as a yeast expression system, technology for purifying VLPs with high efficiency has not definitely advanced yet.

Throughout the specification, various publications and patent documents are referred and citations thereof are represented. The contents of the cited publications and patent documents are inserted into the specification as references, and thus a level of the field of technology including the present invention and the content of the present invention are more clearly explained.

DISCLOSURE

Technical Problem

The inventors made an effort to develop a new method of purifying HPV L1 proteins produced from a host cell expressing a HPV L1 protein with high purity and high efficiency. As a result, the fact that when the HPV L1 proteins were purified by chromatography including treating a homogenate of the host cell expressing the HPV L1 protein with a reducing agent, or treating a homogenate with a reducing agent and performing heating and chilling, a purity of the HPV L1 proteins may be remarkably enhanced, and structural and immunological characteristics of VLPs assembled from the L1 proteins may also be remarkably enhanced was confirmed by an experiment, and therefore the present invention was completed.

Accordingly, the present invention is directed to providing a method of purifying HPV L1 protein with high purity and high efficiency.

An object and advantages of the present invention become more apparent by the detailed description, claims and drawings of the invention.

Technical Solution

In one aspect of the present invention, the present invention provides a method of purifying HPV L1 proteins, which includes: (a) culturing transformed host cells expressing an HPV L1 protein, harvesting the cultured host cells, and disrupting the cells; (b) adding a reducing agent to a homogenate of the host cells; and (c) purifying the HPV L1 proteins by performing chromatography to the homogenate of the host cells to which the reducing agent is added.

In another aspect according to the present invention, a method of purifying HPV L1 proteins is provided. The method includes (i) culturing transformed host cells expressing an HPV L1 protein, harvesting the cultured host cells and disrupting the cells; (ii) adding a reducing agent to the homogenate of the host cells; (iii) heating and chilling the homogenate of the host cells to which the reducing agent is added; and (iv) purifying HPV L1 proteins by performing chromatography to the heated and chilled homogenate of the host cells.

As the result of the effort to develop a new method of purifying HPV L1 proteins produced from the host cells manufactured to express the HPV L1 protein with high purity and high efficiency, it was confirmed by an experiment that when the HPV L1 proteins are purified by chromatography after a homogenate of the host cells expressing the HPV L1 protein is treated with a reducing agent, or a homogenate was heated and chilled after treating with a reducing agent, a purity of the HPV L1 proteins is remarkably enhanced, and structural and immunological characteristics of the VLP assembled from the L1 protein may become excellent, and thus the present invention was completed.

Hereinafter, the present invention will be described in detail by the following operations:

(i) Operation of Culturing Transformed Host Cells Expressing HPV L1 Proteins, Harvesting the Cultured Host Cells and Disrupting the Cells The term "HPV L1 protein" used herein refers to a major protein constituting a HPV capsid, which is expressed from an L1 gene of HPV. The L1 proteins self-assembles into a VLPs alone or does in combination with a minor proteins, L2 proteins, to construct the capsids.

Papillomavirus is an icosahedral DNA genome virus, which has a maximum eight early genes (E) and two late genes (L), and a size of 50 to 60 nm, and no envelope. In the gene E, the "E" means early, and in the gene L, the "L" means late. The E gene is a gene involved in virus replication and transformation. The L1 and L2 genes encode a virus capsid protein. The L1 protein is a major capsid protein, and has a molecular weight of 55 to 60 kDa. The L2 protein is a minor capid protein having an estimated molecular weight of 55 to 60 kDa and an apparent molecular weight of 75 to 100 kDa, measured by PAGE.

In the method of the present invention, a type of HPV from which the L1 protein is derived, may be selected from, but is not particularly limited to, the group consisting of HPV type 6a, HPV type 6b, HPV type 11, HPV type 16, HPV type 18, HPV type 30, HPV type 31, HPV type 33, HPV type 35, HPV type 39, HPV type 41, HPV type 42, HPV type 43, HPV type 44, HPV type 45, HPV type 51, HPV type 52, HPV type 54, HPV type 55, HPV type 56, HPV type 58, HPV type 68 and HPV type 70, and more preferably, the L1 protein of the present invention may be derived from HPV selected from the group consisting of HPV type 6a, HPV type 6b, HPV type 11, HPV type 16, HPV type 18, HPV type 31, HPV type 33, HPV type 45 and HPV type 58, and most preferably, derived from HPV type 16, HPV type 18, or HPV type 58.

In the present invention, cells used as host cells are bacteria, yeast cells, insect cells, plant cells or animal cells.

According to an exemplary embodiment of the present invention, the yeast cell is *Saccharomyces cerevisiae, Saccharomyces pastorianus, Saccharomyces* sp., *Schizosaccharomyces pombe, Pichia Pastoris,* or *Hansenula polymorpha.*

In the present invention, the transformed host cells expressing an HPV L1 protein are host cells transformed by an expression vector successfully expressing an HPV L1 protein. The expression vector may include a transcription or translation regulatory factor known in the art, or a marker gene. The transformed host cell expressing the HPV L1 protein of the present invention may be easily manufactured using a known method in the art.

(ii) Operation of Adding Reducing Agent to Homogenate of the Host Cells

The term "reducing agent" used herein refers to an element or compound donating electrons to other species in a reduction-oxidation reaction, and preferably, a compound used to reduce a disulfide bond in a peptide or protein or stabilize a free sulfhydryl group.

In the present invention, the reducing agent is selected from, for example, the group consisting of β-mercaptoethanol, dithiothreitol (DTT), 2-mercaptoethylamine-HCl, tris (2-carboxyethyl)phosphine (TCEP) and cysteine-HCl, and preferably, β-mercaptoethanol or DTT.

In the present invention, the final concentration of the reducing agent in the cell homogenate may be 0.1 wt % or more, preferably, 0.1 to 20 wt %, more preferably 0.1 to 10 wt %, further more preferably 1 to 8 wt %, still more preferably 3 to 7 wt %, and most preferably 4 to 6 wt %.

In the present invention, a time for reacting the reducing agent with the cell homogenate is not limited to a specific range of time, and one of ordinary skill in the art may select a reaction time suitable for the method of the present invention.

(iii) Operation of Heating and Chilling the Homogenate of the Host Cells to which the Reducing Agent is Added In the present invention, the reducing agent is added to the cell homogenate, and heating and chilling is performed. As proved as an experiment result in an exemplary embodiment, when the cell homogenate to which the reducing agent is added is heated and chilled, efficiency of removing impurities from the homogenate of the transformed host cells is remarkably increased, and a VLP assembled from the L1 proteins has a preferable structure and immunological characteristic.

In the present invention, a heating temperature of the cell homogenate is higher than room temperature, preferably, more than 25° C., more preferably, more than 25 to less than 80° C., further more preferably, 30 to 65° C., still more preferably 35 to 65° C., and most preferably 35 to 60° C., and the optimal heating condition is 35 to 55° C.

In the present invention, the heating time of the cell homogenate may be changed according to the heating temperature, and may be suitably selected in the range of 10 minutes to 72 hours, but the present invention is not limited to that range. The heating time is preferably 30 minutes to 72 hours, more preferably, 30 minutes to 48 hours, further more preferably, 30 minutes to 24 hours, and most preferably, 30 minutes to 12 hours.

In the present invention, the chilling temperature is a temperature at which a sample of the cell homogenate is not frozen. Such a chilling temperature is 0 to 10° C., preferably, more than 0° C. to less than 8° C., more preferably, more than 0° C. to less than 7° C., further more preferably, more than 0° C. to less than 6° C., and most preferably, more than 0° C. to less than 5° C. Chilling time may be used by selecting a chilling time suitable for the method of the present invention.

Meanwhile, according to the example, the homogenate of the host cells to which the reducing agent is added may not be heated and chilled, and maintained at room temperature.

The term "room temperature" used herein is a non-heated or non-chilled atmospheric temperature, which is 15 to 25° C.

(iv) Operation of Purifying HPV L1 Proteins by Performing Chromatography on the Homogenate of the Host Cells to which the Reducing Agent is Added or the Heated and Chilled Homogenate of the Host Cells HPV L1 proteins are purified by performing chromatography-based purification on the homogenate of the host cells to which the reducing agent is added, or by performing chromatography-based purification on the homogenate of the host cells after adding a reducing agent to the homogenate and heating and chilling the homogenate.

In the present invention, available chromatography is known in the art, and may be, but is not limited to, for example, ion exchange chromatography such as cation exchange chromatography or anion exchange chromatography, size-exclusion chromatography (SEC), hydrophobic interaction chromatography, or affinity chromatography. In the present invention, ion exchange chromatography which is most suitable for separation of a protein or peptide is preferably used because a substance to be separated and purified is a protein. In an exemplary example of the present invention, a type of the cation exchange chromatography, heparin resin chromatography or cation exchange chromatography was used to successfully separate and purify HPV L1 proteins.

Characteristics and advantages of the present invention are summarized below:

i) The present invention provides a method of purifying HPV L1 proteins with high purity and high efficiency.

ii) The purification method of the present invention is characterized by purifying L1 proteins by chromatography after a reducing agent is added to a cell homogenate of HPV L1 protein-expressing transformed host cells, or after performing heating and chilling after treatment with reducing agent to the cell homogenate.

iii) According to the purification method of the present invention, a purification purity of HPV L1 protein may be remarkably enhanced.

iv) VLPs of the HPV L1 proteins purified by the purification method of the present invention form a high quality structure, and have very excellent immunogenicity.

Advantageous Effects

The present invention relates to a method of purifying HPV L1 proteins with high purity and high efficiency. According to the purification method of the present invention, a purification purity of the HPV L1 proteins may be remarkably enhanced, and since VLPs of the purified HPV L1 protein form a more similar structure to that of an original HPV virion, the VLPs have very excellent immunogenicity.

(Prior Art Document 1) Kim H J, Kim S Y, Lim S J, Kim J Y, Lee S J, et al. (2010) One-step chromatographic purification of human papillomavirus type 16 L1 protein from *Saccharomyces cerevisiae*. Protein Expr Purif 70: 68-74;

(Prior Art Document 2) Kim H J, Lim S J, Kim J Y, Kim S Y, Kim H-J (2009) A method for removing contaminating protein during purification of human papillomavirus type 18 L1 protein from *Saccharomyces cerevisiae*. Arch Pharm Res 32: 1759-1766;

(Prior Art Document 3) Registered patent, cervical cancer vaccine, Application No: 10-2011-0137242 (Dec. 19, 2011), Registration No: 1011780560000 (Aug. 21, 2012); and (Prior Art Document 4) Registered patent, cervical cancer vaccine, Application No:10-2009-0099982 (Oct. 20, 2009), Registration No: 1011819070000 (Sep. 5, 2012).

To performing the T-5 method, host cells, *Saccharomyces cerevisiae*, expressing an HPV L1 proteins were disrupted, and then a reducing agent was added to the cell homogenate. After the reducing agent was treated, heating and chilling were performed to remove impurities. The L1 proteins contained in impurities-removed cell homogenate were purified by heparin chromatography. The L1 proteins purified by the first-purification were further purified by second heparin chromatography with high purity.

In the T-1 method, L1 proteins in the *Saccharomyces cerevisiae* homogenate were recovered by ammonium sulfate precipitation. Impurities in the recovered fraction were removed by removal of precipitated contaminants. The L1 proteins in the homogenate processed through the above process were purified by heparin chromatography.

Figure 2:
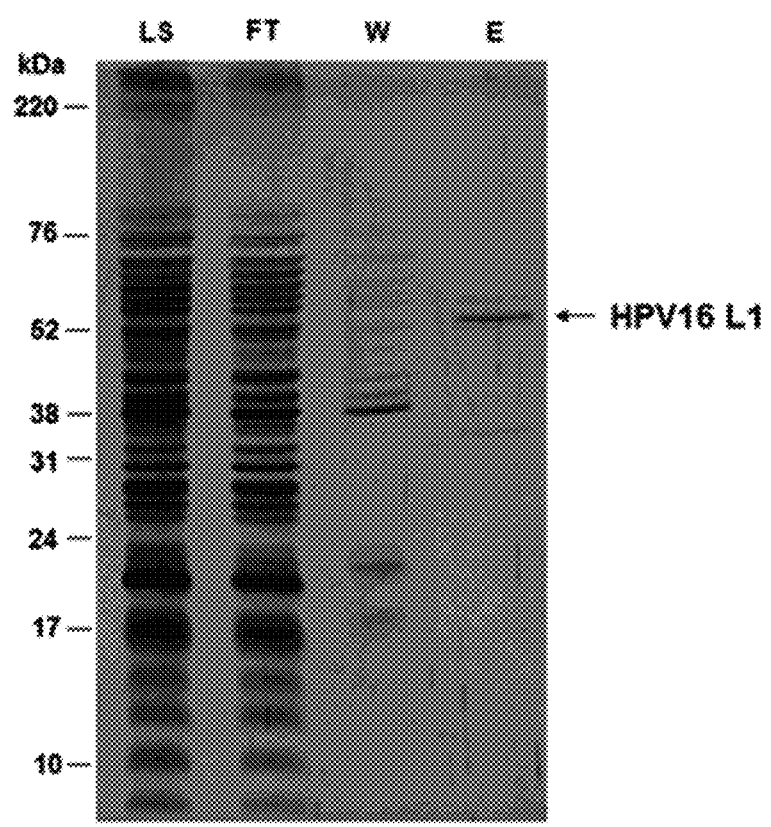

FIG. 2 shows a purification result obtained by the T-5 method including dialysis of a homogenate of a host cells expressing L1 proteins, treating the dialyzed result with a reducing agent and performing heating and chilling, performing first heparin chromatography, and the chromatography result was confirmed by SDS-PAGE. It appeared that high purity of HPV L1 proteins were recovered after the first heparin chromatography. LS indicates loading sample that was loaded onto a heparin resin, and FT indicates a flow-through, which is a fraction flowing through without binding to the heparin resin. W indicates a wash, which is a fraction flowing through while the heparin resin is washed, and E indicates an elution, which is a fraction in which HPV L1 protein is eluted with a buffer solution including 1M NaCl.

Figure 3:
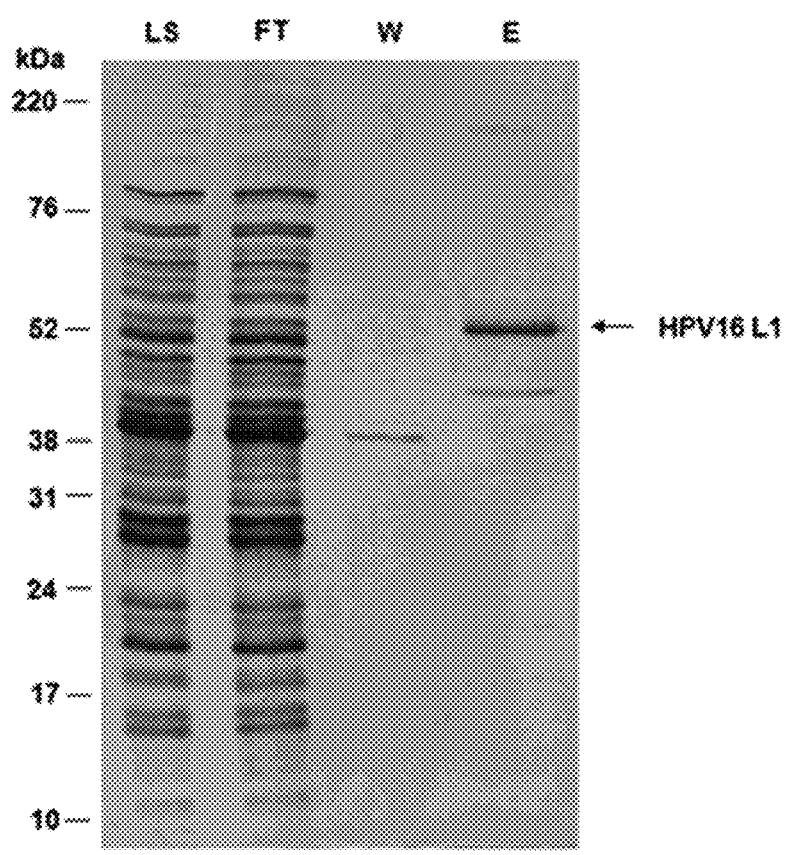

FIG. 3 shows a purification result obtained by the T-5 method, including directly treating a homogenate of HPV L1 protein-expressing host cells with a reducing agent without dialysis of the cell homogenate, performing heating and chilling, and performing first heparin chromatography. The chromatography result was confirmed by SDS-PAGE. Similar to the result of FIG. 2, high purity HPV L1 proteins were also obtained after the first heparin chromatography. LS, FT, W and E were the same as described in FIG. 2.

Figure 4:
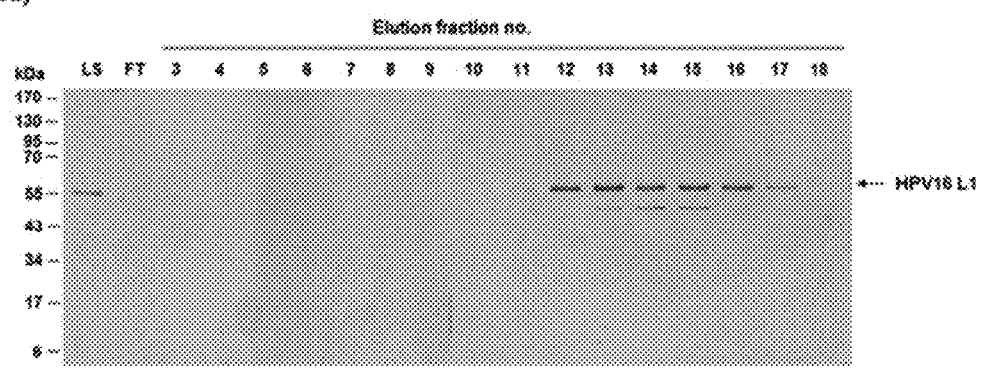
Figure 4:
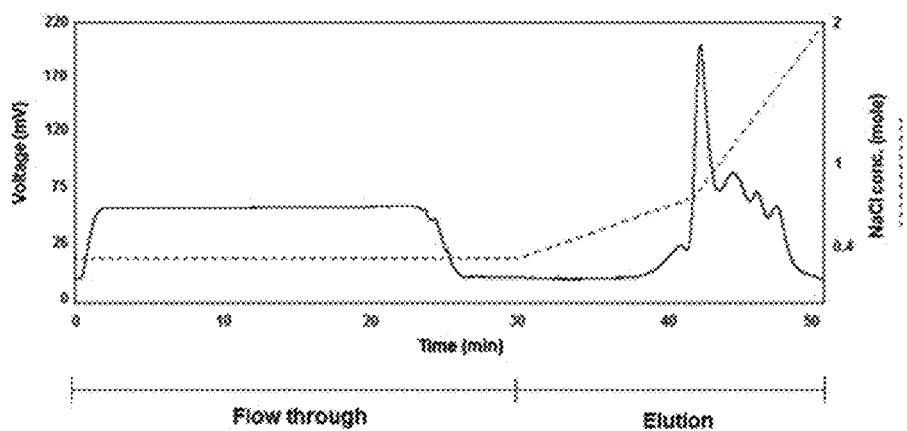

FIG. 4a shows a purification result obtained by the T-5 method, including treating a homogenate of HPV L1 protein expressing host cells with a reducing agent, performing heating and chilling, performing first heparin chromatography and performing second heparin chromatography. The result was confirmed by SDS-PAGE. LS and FT are the same as described in FIG. 2. Numerals from 3 to 18 shown in an upper part of the SDS-PAGE image indicate respective numbers of fractions obtained in a linear gradient elution using NaCl.

FIG. 4b shows a profile of the second heparin chromatography. In the flow-through (FT) of the SDS-PAGE of FIG. 4a, a protein band was not detected, whereas in the FT of FIG. 4b, it was confirmed that a great amount of contaminating substances were flowed through. Accordingly, the result of FIG. 4b shows that a considerable amount of contaminating substances were removed by the second heparin chromatography.

Figure 1:
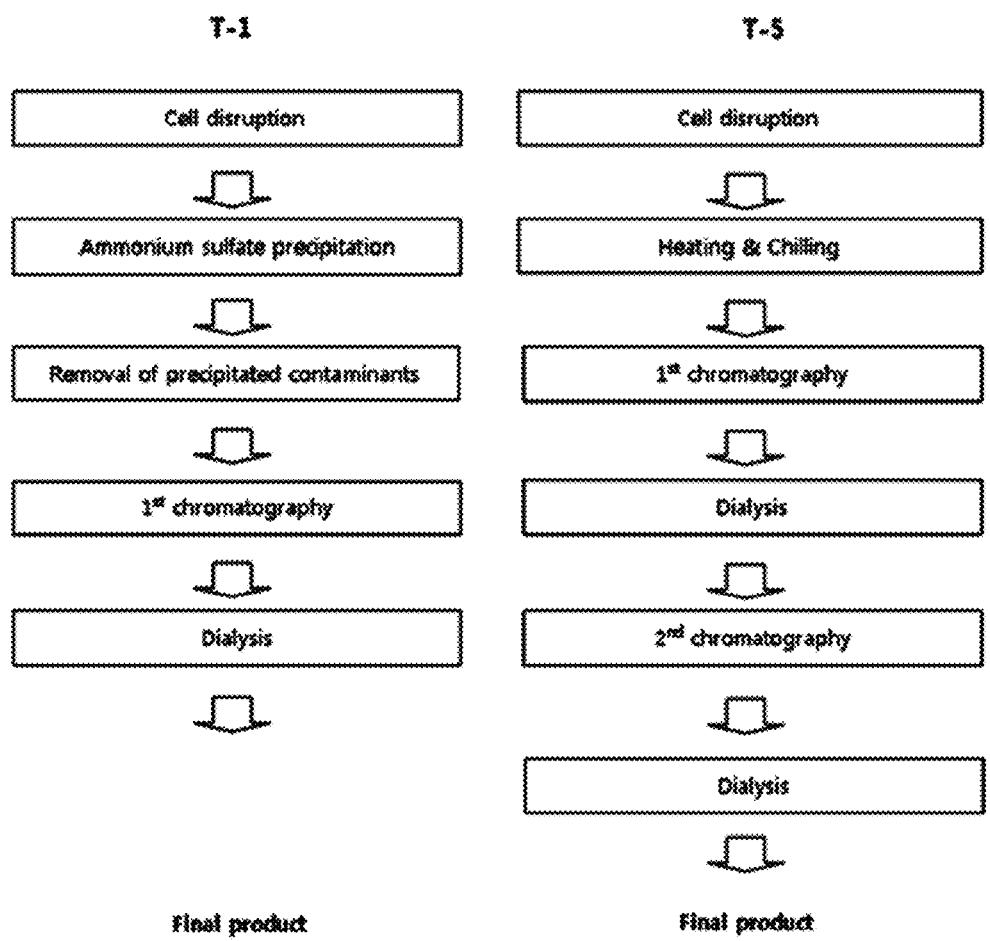
FIG. 1 shows a method described in a prior art document to purify HPV VLPs (hereinafter, referred to as a "T-1" method) and a method of the present invention (hereinafter, referred to as a "T-5" method). The prior art documents relating to the T-1 method are as follows.
Figure 5:
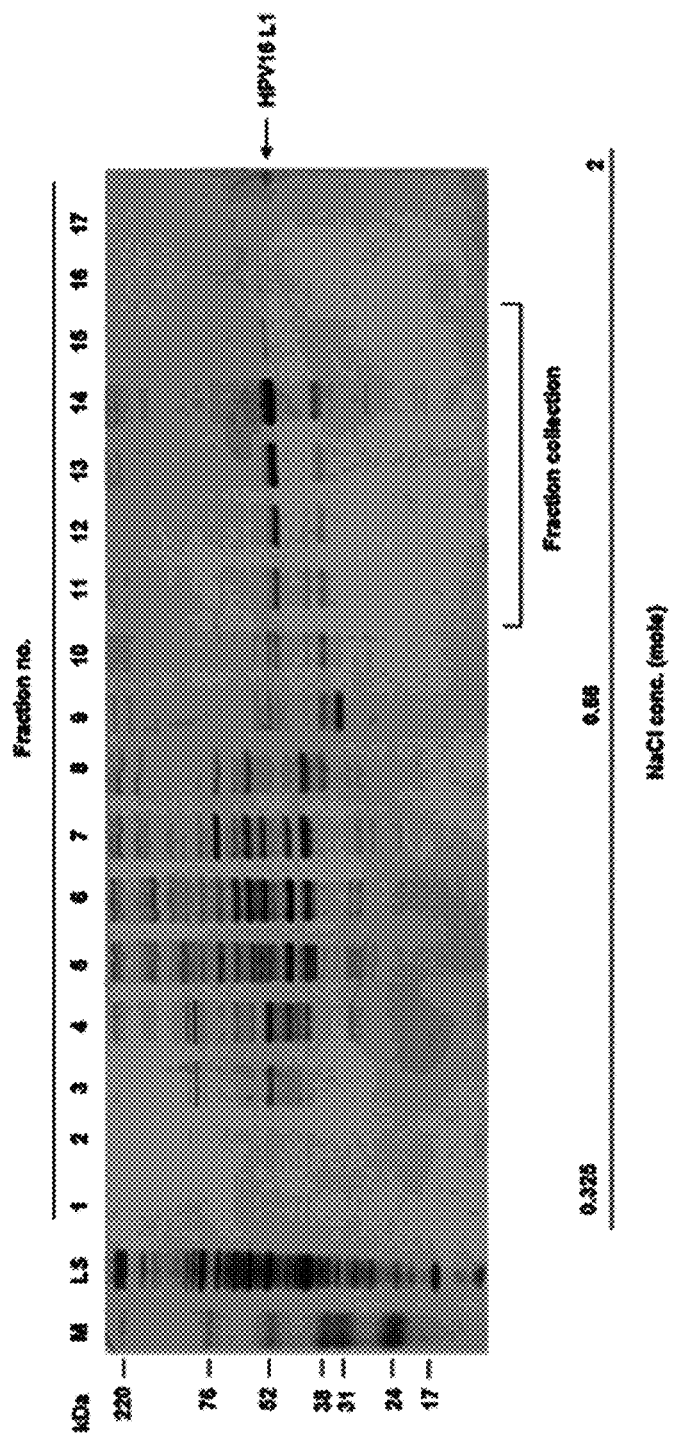

FIG. 5 shows an SDS-PAGE result for heparin chromatography according to the T-1 method. Treatment of a sample before the heparin chromatography was performed as shown in FIG. 1. LS indicates a loading sample. Proteins bound with a heparin resin were eluted by a method of linear gradient of increasing NaCl. The linear gradient elution was performed to have a content of NaCl from 0.325 M to 2 M. In the SDS-PAGE result, numerals of the upper part indicate numbers of elution fractions. It is shown that, in fractions 11 to 14, an L1 protein was eluted with high purity.

Figure 6:
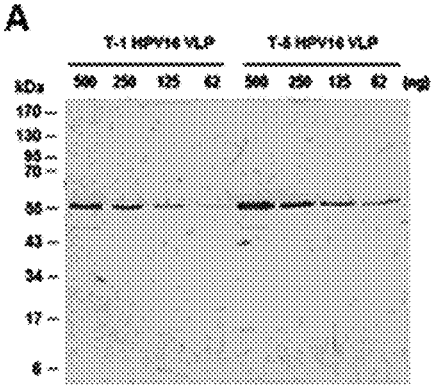
Figure 6:
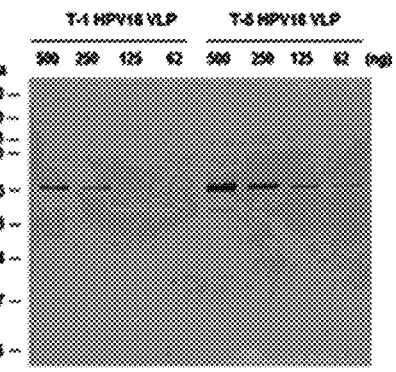
Figure 6:
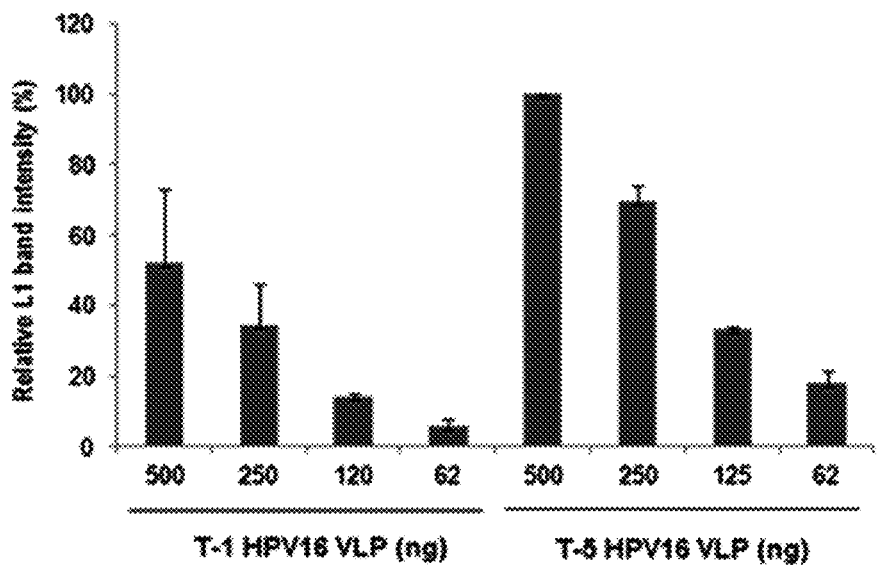

FIG. 6a shows a comparison result between purities of VLPs purified by the conventional method (T-1 method) and the T-5 method. The "T-1 HPV16 VLP" is a product purified by a conventional known method [Kim et al. (2010) Protein Expr Purif 70: 68-74; Kim et al. (2009) Arch Pharm Res 32: 1759-1766], and the "T-5 HPV16 VLP" is a product purified by the method of the present invention. In SDS-PAGE analysis of the HPV L1 proteins, quantification of the protein was performed, and proteins were loaded at 500 ng, 250 ng, 125 ng and 62 ng per well. Independently, an experiment was performed twice, and respective experiments were represented as Panel A and Panel B. According to the results obtained by the two experiments, it was seen that an intensity of an L1 protein band of the T-5 HPV 16 VLPs was much higher than that of the T-1 HPV 16 VLPs.

FIG. 6b are a graph showing intensities of L1 protein bands of T-1 HPV 16 VLP and T-5 HPV 16 VLP detected in the two experiments shown in FIG. 6a. The results were presented as mean±standard deviation, and the intensity of the L1 protein band of T-5 HPV 16 VLP loaded at 500 ng per well was set at 100%. This result shows that the purity of VLPs purified by the T-5 method is far superior to that of the VLPs purified by the T-1 method.

Figure 7:
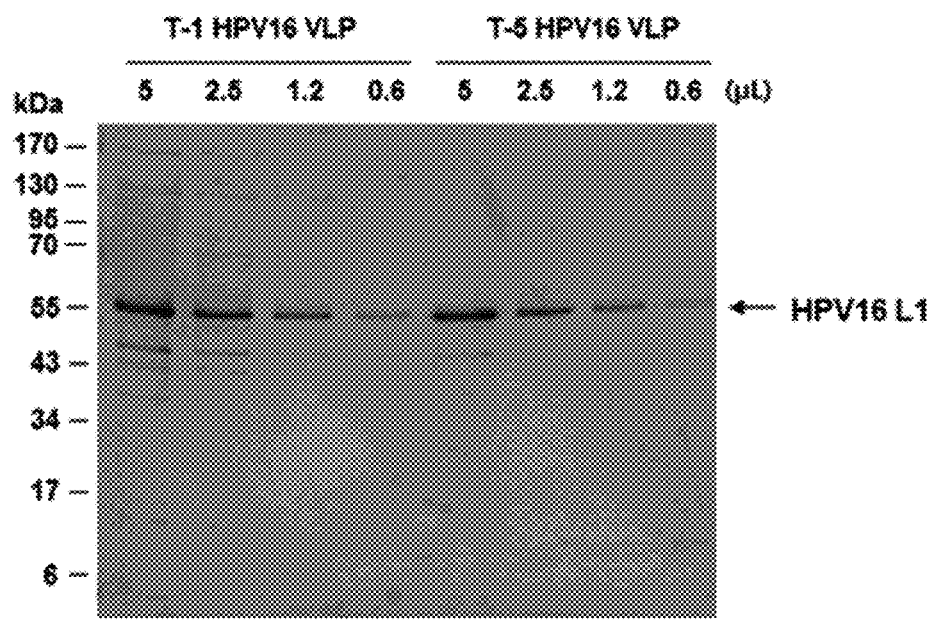

FIG. 7 shows a SDS-PAGE result when T-1 HPV 16 VLPs were loaded to have the same intensity of an L1 protein band as that of T-5 HPV 16 VLPs.

Figure 8:
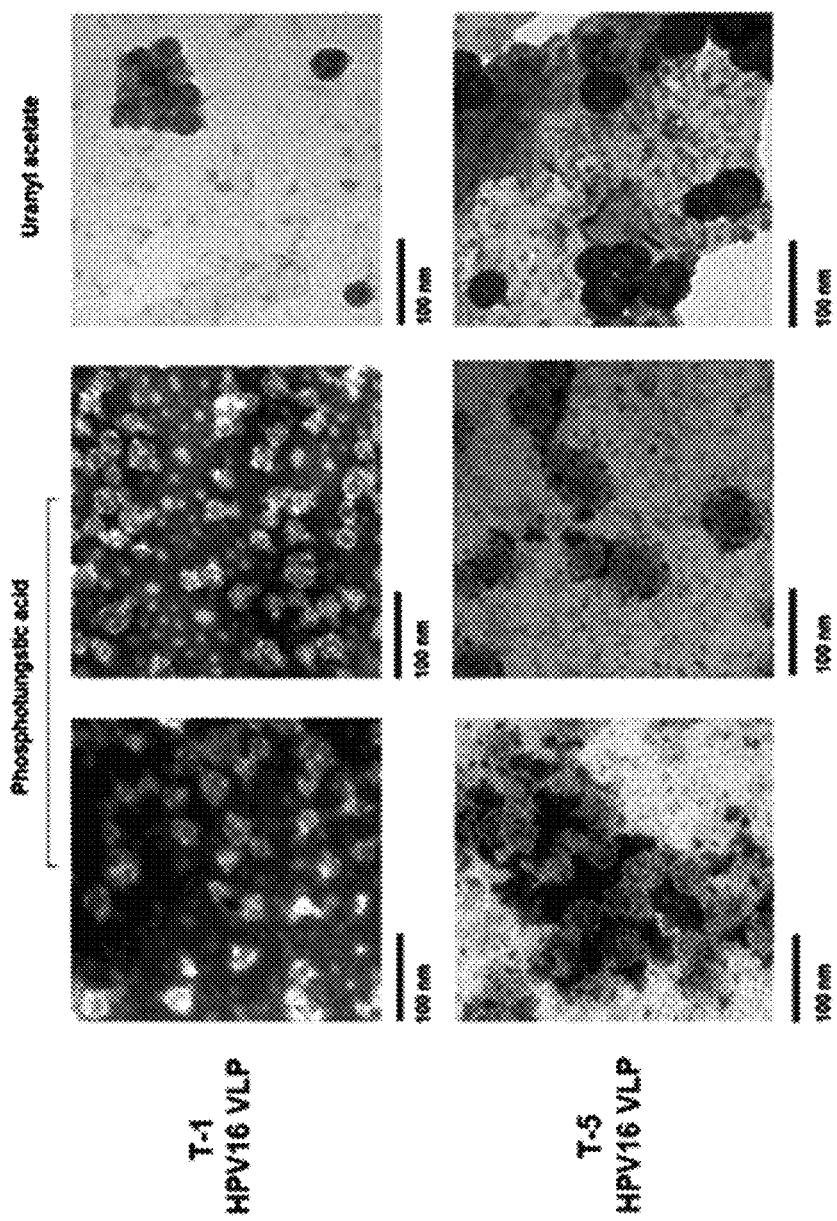

FIG. 8 shows electron microscopy results for T-1 HPV16 VLPs and T-5 HPV 16 VLPs. It was confirmed that the T-1 HPV 16 VLPs had a size of 20 to 50 nm, and the T-5 HPV16 VLPs had a size of 40 to 65 nm. This denotes that the size of the T-5 HPV 16 VLP is closer to an original size of HPV (50 to 60 nm) [29, 30].

Figure 9:
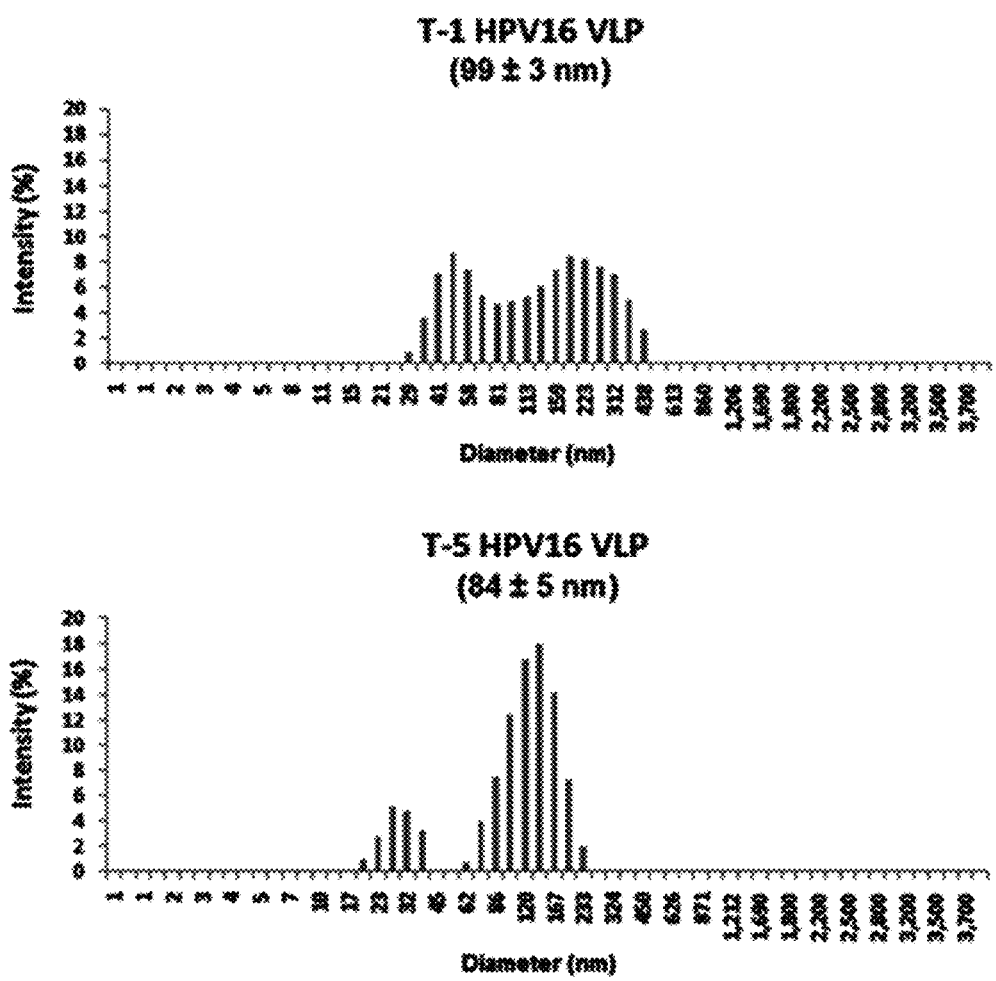
Figure 10:
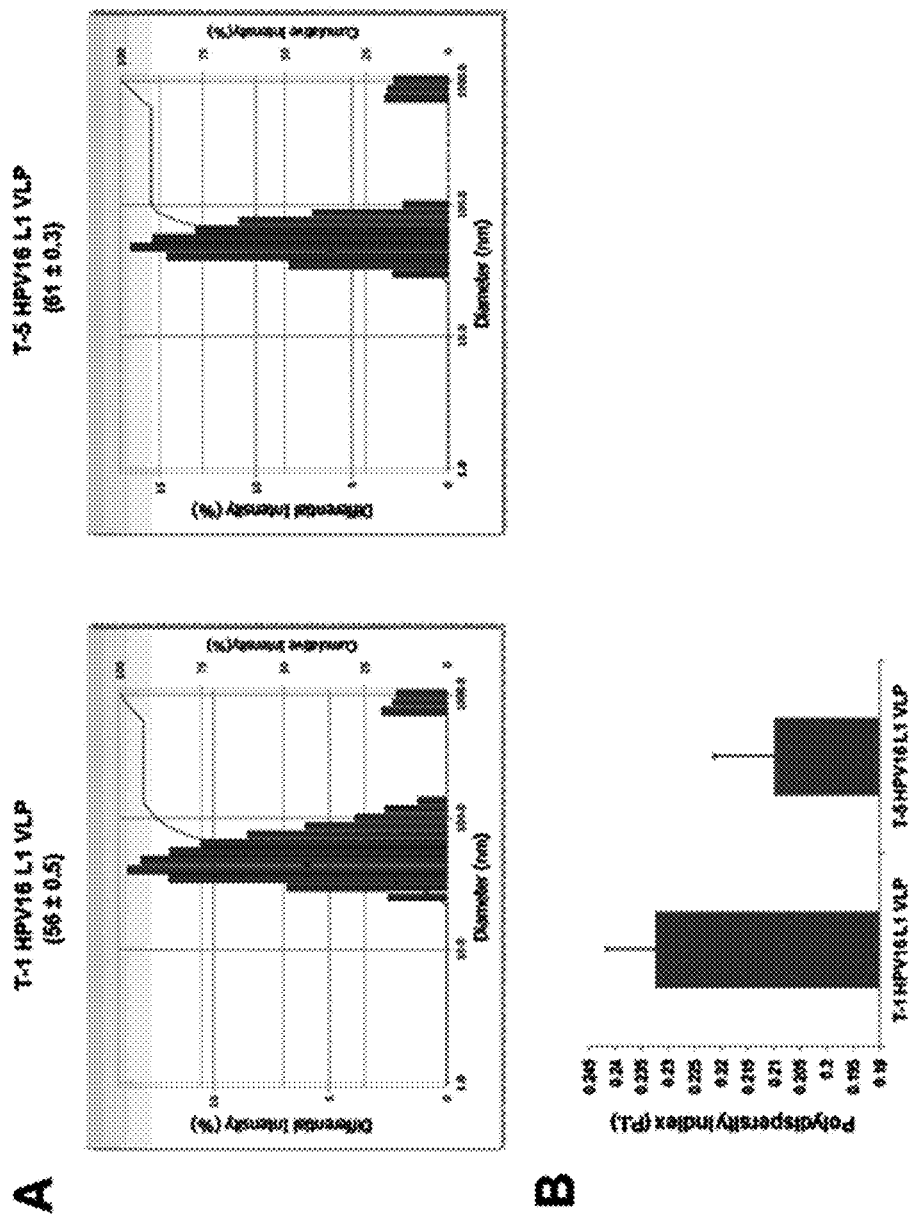

FIGS. 9 and 10 show dynamic light scattering (DLS) results. The DLS measures a size of VLP in a solution. Size distribution of VLPs in the solution was analyzed using DLS-700 (FIG. 9) and ELS-Z2 (FIG. 10) systems. As shown in the results of FIGS. 9 and 10, it appeared that size distributions of the two types of VLPs are different from each other. The result shows that physical properties of the T-5 HPV 16 VLPs are different from those of the T-1 HPV16 VLPs.

Figure 11:
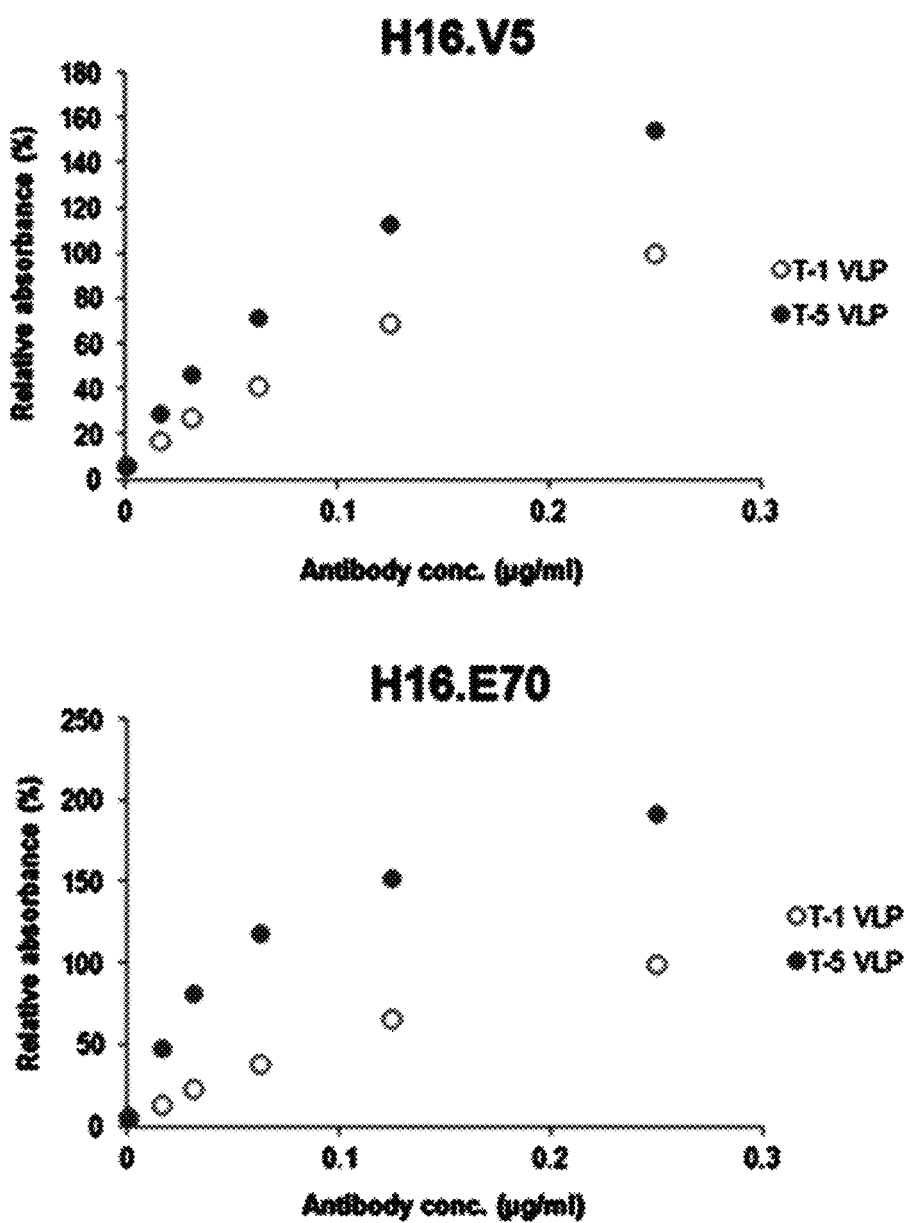

FIG. 11 shows reactivity of monoclonal antibodies with respect to T-1 HPV 16 L1 VLP and T-5 HPV16 L1 VLP. To investigate the reactivity of anti-HPV 16 L1 monoclonal antibodies, previously known monoclonal antibodies, H16.V5 and H16.E70, were used. An increase in reactivity of VLPs with respect to the two antibodies is known to have a close relationship with an increase in immunogenicity [26, 32-34]. It was confirmed that the reactivity of T-5 HPV 16 VLPs with respect to the H16.V5 and H16.E70 antibodies is far higher than those of T-1 HPV 16 VLPs.

Figure 12:
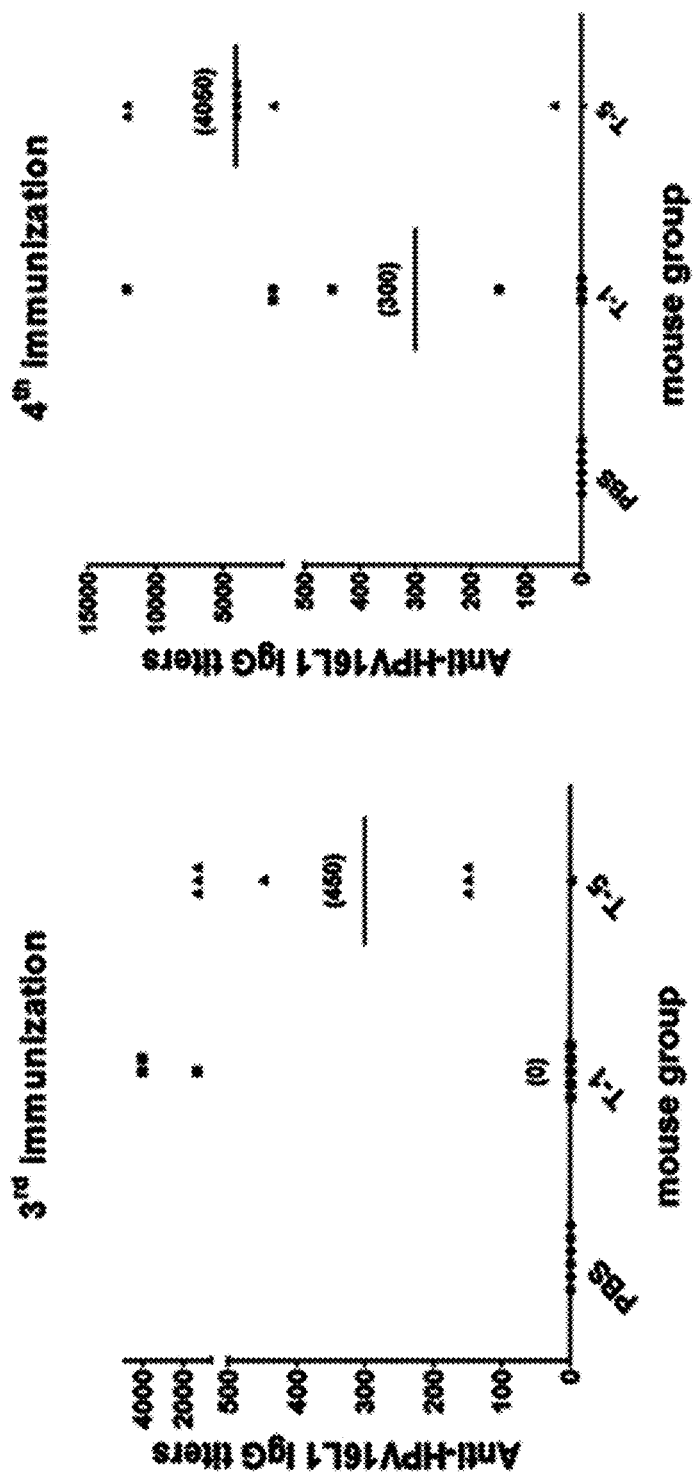

FIG. 12 shows results obtained by analyzing immunogenicities of T-1 HPV16 L1 VLPs and T-5 HPV16 L1 VLPs. To compare the immunogenicities, 1 ng of VLPs was subcutaneously injected into a mouse with 200 μg of aluminum hydroxide. The immunization was performed four times at two week intervals. 10 days after the third and fourth immunizations, anti-HPV 16 L1 IgG antibody titers were detected from a serum. As the result of anti-HPV16 L1 IgG antibody titration, it was confirmed that the level of anti-HPV16 L1 IgG induced by T-5 HPV16 L1 VLPs is 10 times higher than that of T-1 HPV16 L1 VLPs.

Figure 13:
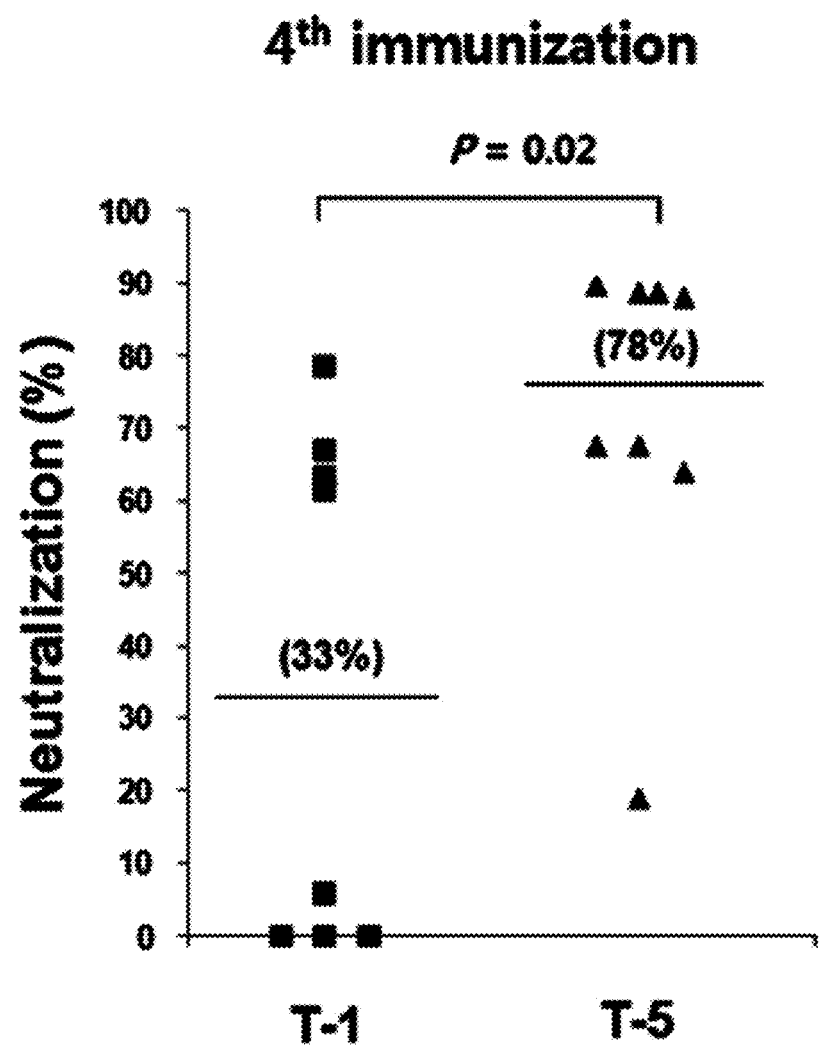

FIG. 13 shows anti-HPV16 neutralizing antibody activity of serum collected after fourth immunization in the immunization performed in FIG. 12. A neutralizing activity of a mouse serum immunized with T-5 HPV16 L1 VLPs was 78%, whereas a neutralizing activity of a mouse serum immunized with T-1 HPV16 L1 VLPs was 33%.

Figure 14:
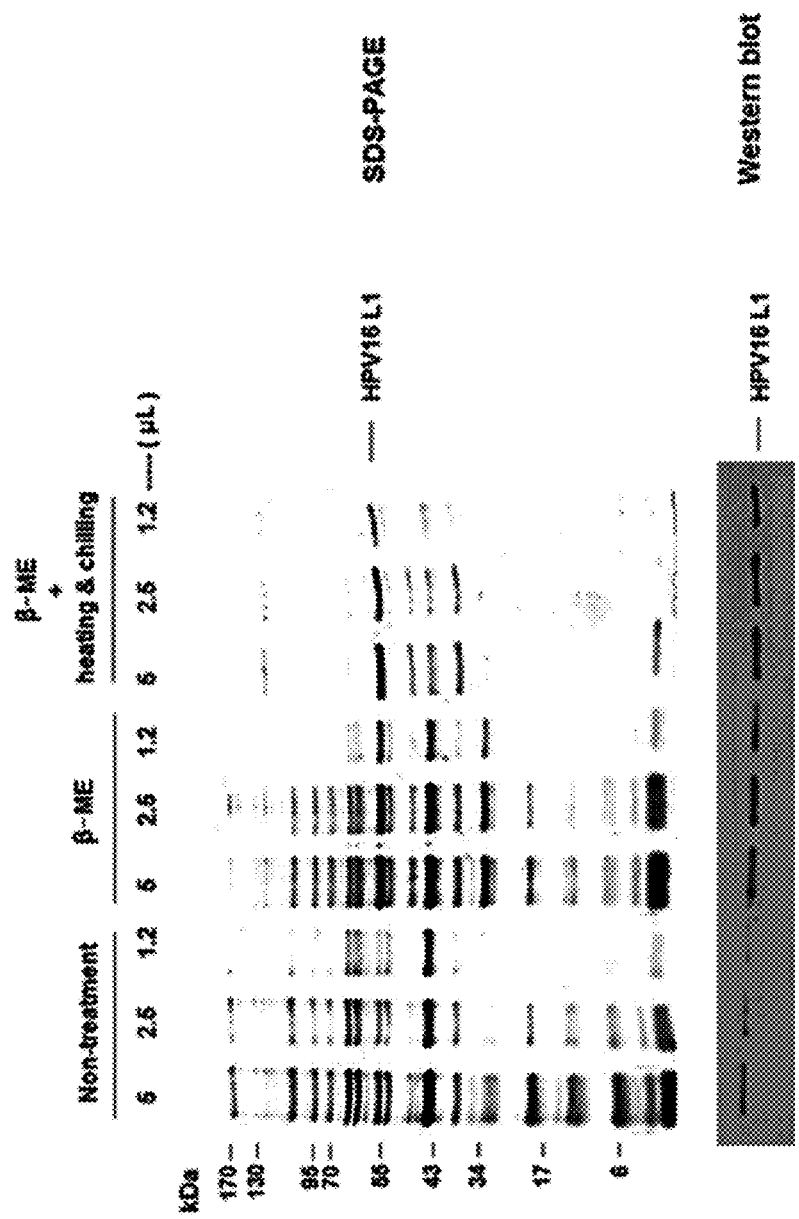

FIG. 14 shows comparison of purities of an HPV L1 protein purified when a homogenate was not treated (non-treatment), a homogenate was treated with a reducing agent (β-ME), and when a homogenate was heated and chilled after treatment with a reducing agent (β-ME+heating and chilling). A sample going through each condition was eluted by a first heparin chromatography, and the same volume each (5, 2.5 or 1.2 μl) of the protein, for each condition, was taken from the elution fraction and loaded in a gel to perform SDS-PAGE and Western blotting. According to the result of FIG. 14, it was confirmed that a purity of the HPV L1 protein when the homogenate was treated with a reducing agent, heated and chilled (T-5, β-ME+heating and chilling) is far higher than those in the other conditions.

Figure 15:
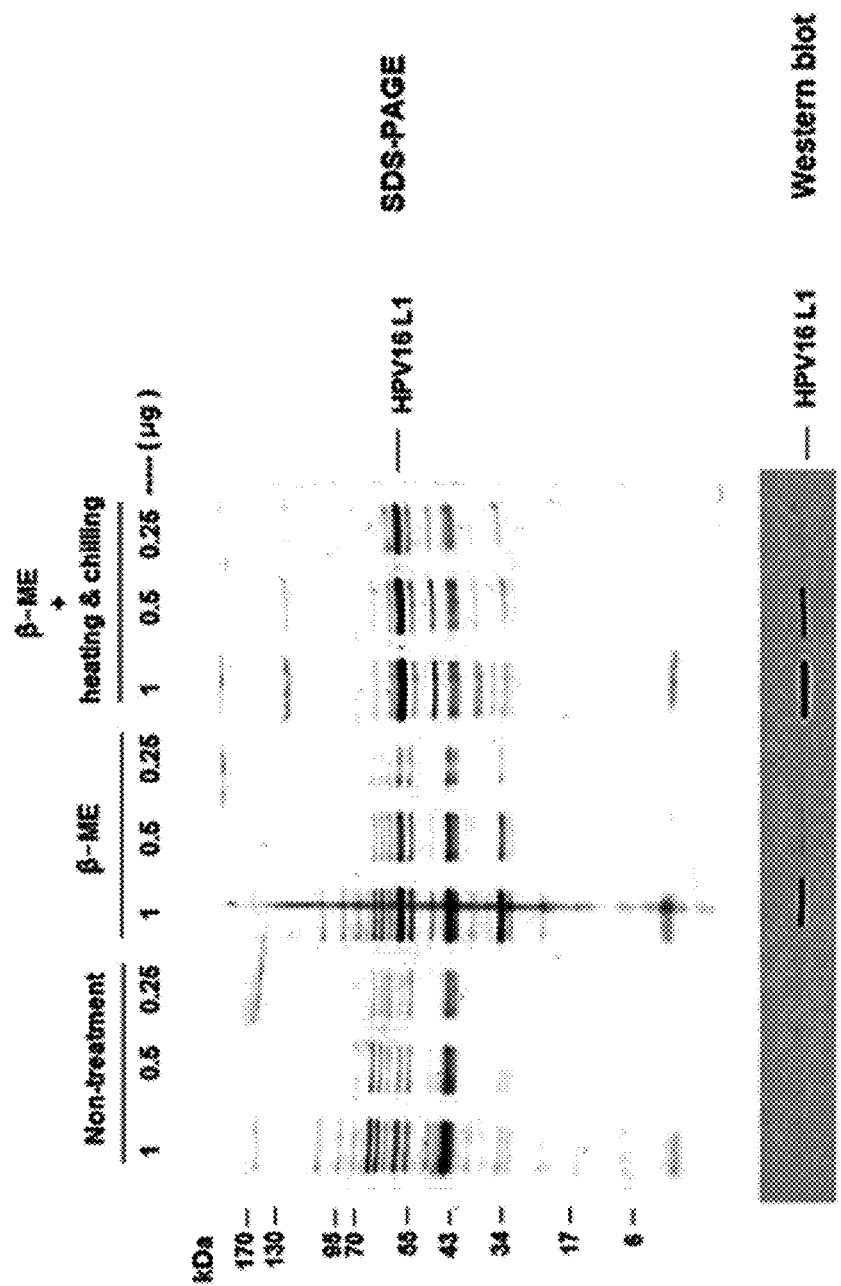

FIG. 15 shows comparison of purities of an HPV L1 protein purified when a homogenate was not treated (non-treatment), when a homogenate was treated with a reducing agent (β-ME), and when a homogenate was heated and chilled after treatment with a reducing agent (T-5, β-ME+heating and chilling). A sample going through each condition was eluted by first heparin chromatography, the same amount (1, 0.5 or 25 μg) each of the protein was taken from the elution fraction and loaded in a gel to perform SDS-PAGE and Western blotting. According to the result of FIG. 15, it was confirmed that a purity of the HPV L1 protein when a homogenate was treated with a reducing agent, heated and chilled (T-5, β-ME+heating and chilling) is far higher than those in the other conditions.

Figure 16:
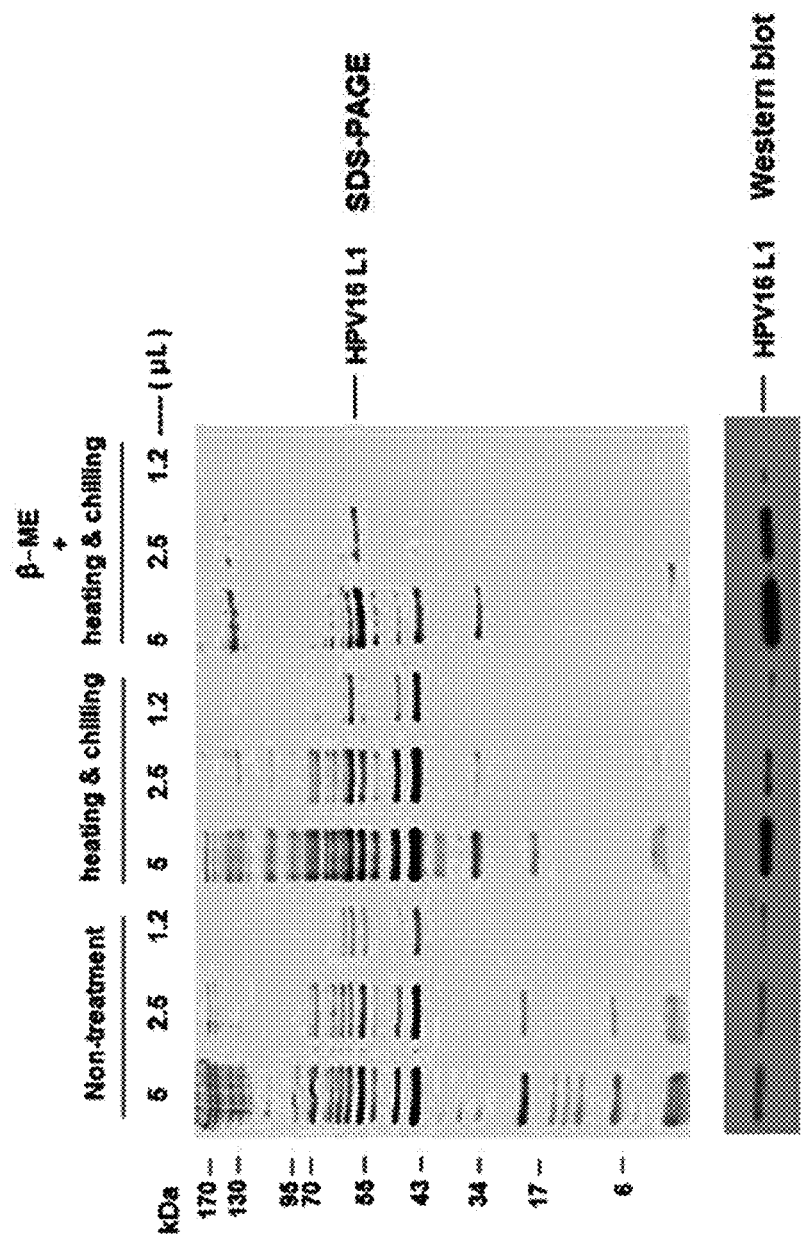

FIG. 16 shows comparison of purities of an HPV L1 protein purified when a homogenate was not treated (non-treatment), when a homogenate was not treated with a reducing agent, but was only heated and chilled (heating and chilling), and when a homogenate was treated with a reducing agent, heated and chilled (T-5, β-ME+heating and chilling). A sample going through each condition was eluted by first heparin chromatography, the same volume (5, 2.5 or 1.2 μl) each of the protein, for each condition, was taken from the elution fraction and loaded in a gel to perform SDS-PAGE and Western blotting. According to the result of FIG. 16, it was confirmed that a purity of the HPV L1 protein when a homogenate was treated with a reducing agent, heated and chilled (T-5, β-ME+heating and chilling) is far higher than those in the other conditions.

Figure 17:
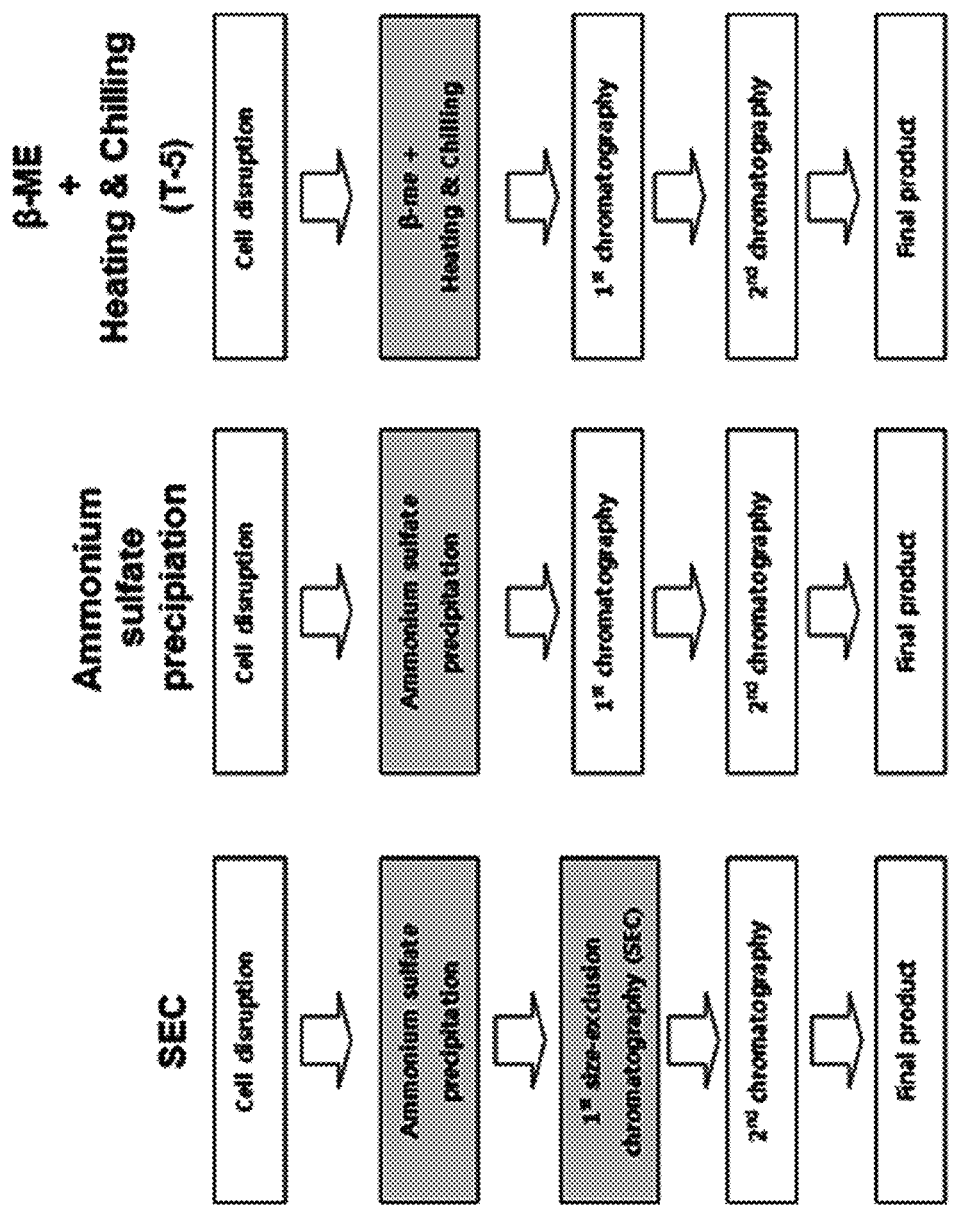

FIG. 17 shows a purification method based on size-exclusion chromatography (SEC), a purification method based on ammonium sulfate precipitation, and a purification method performed by heating and chilling after treatment with a reducing agent (T-5, β-ME+heating & chilling). To compare effects of the SEC and the ammonium sulfate precipitation with that of the method performed by heating and chilling after treatment with a reducing agent, the step that is heating and chilling after the treatment with a reducing agent in the T-5 purification method was substituted with the SEC or ammonium sulfate precipitation. The SEC and ammonium sulfate precipitation (T-1-based method) were based on a method disclosed in a prior art document.

1) Prior Art Documents Relating to SEC (Prior Art Document 1) Park M A, Kim H J, Kim H-J (2008) Optimum conditions for production and purification of human papillomavirus type 16 L1 protein from *Saccharomyces cerevisiae*. Protein Expr Purif 59: 175-181.

(Prior Art Document 2) Registered Patent, Methods of producing and purifying HPV virus-like particles, Application No: 10-2008-0026586 (2008 Mar. 21), Registration No: 1009591450000 (May 13, 2010)

2) Prior Art Documents on Ammonium Sulfate Chromatography (Prior Art Document 1) Kim H J, Kim S Y, Lim S J, Kim J Y, Lee S J, et al. (2010) One-step chromatographic purification of human papillomavirus type 16 L1 protein from *Saccharomyces cerevisiae*. Protein Expr Purif 70: 68-74.

(Prior Art Document 2) Kim H J, Lim S J, Kim J Y, Kim S Y, Kim H-J (2009) A method for removing contaminating protein during purification of human papillomavirus type 18 L1 protein from *Saccharomyces cerevisiae*. Arch Pharm Res 32: 1759-1766.

(Prior Art Document 3) Registered Patent, cervical cancer vaccine, Application No: 102011-0137242 (Dec. 19, 2011), Registration No: 1011780560000 (Aug. 21, 2012)

(Prior Art Document 4) Registered Patent, cervical cancer vaccine, Application No:102009-0099982 (Oct. 20, 2009), Registration No: 1011819070000 (Sep. 5, 2012)

Figure 18:
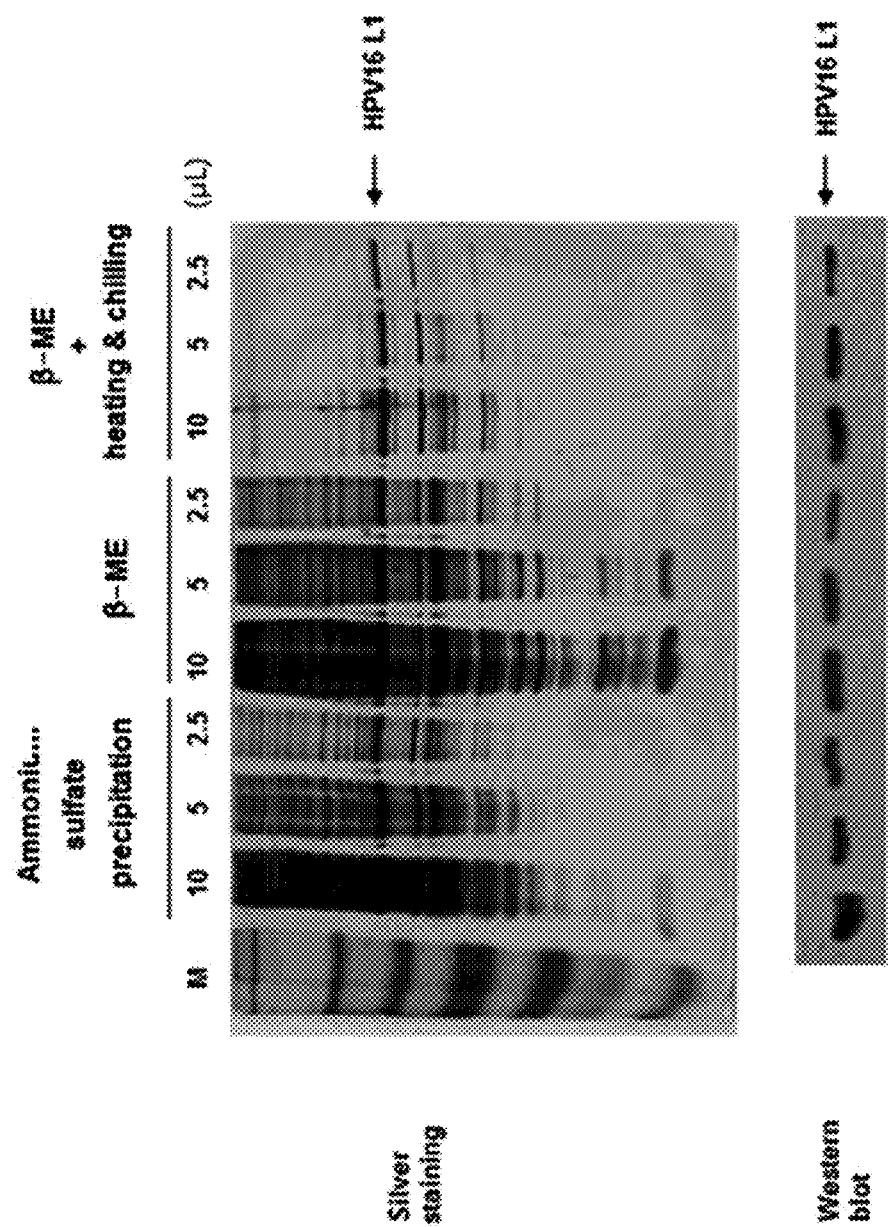

FIG. 18 shows a difference between ammonium sulfate precipitation, a reducing agent-treatment method (β-ME), and a purification method performed by treatment with a reducing agent and heating/chilling (T-5, β-ME+heating & chilling). Purity of elution fraction of first chromatography in each purification condition was analyzed by SDS-PAGE and Western blotting. As a result, it was confirmed that an L1 protein recovered by the method including treatment with β-ME and heating/chilling has the highest purity.

Figure 19:
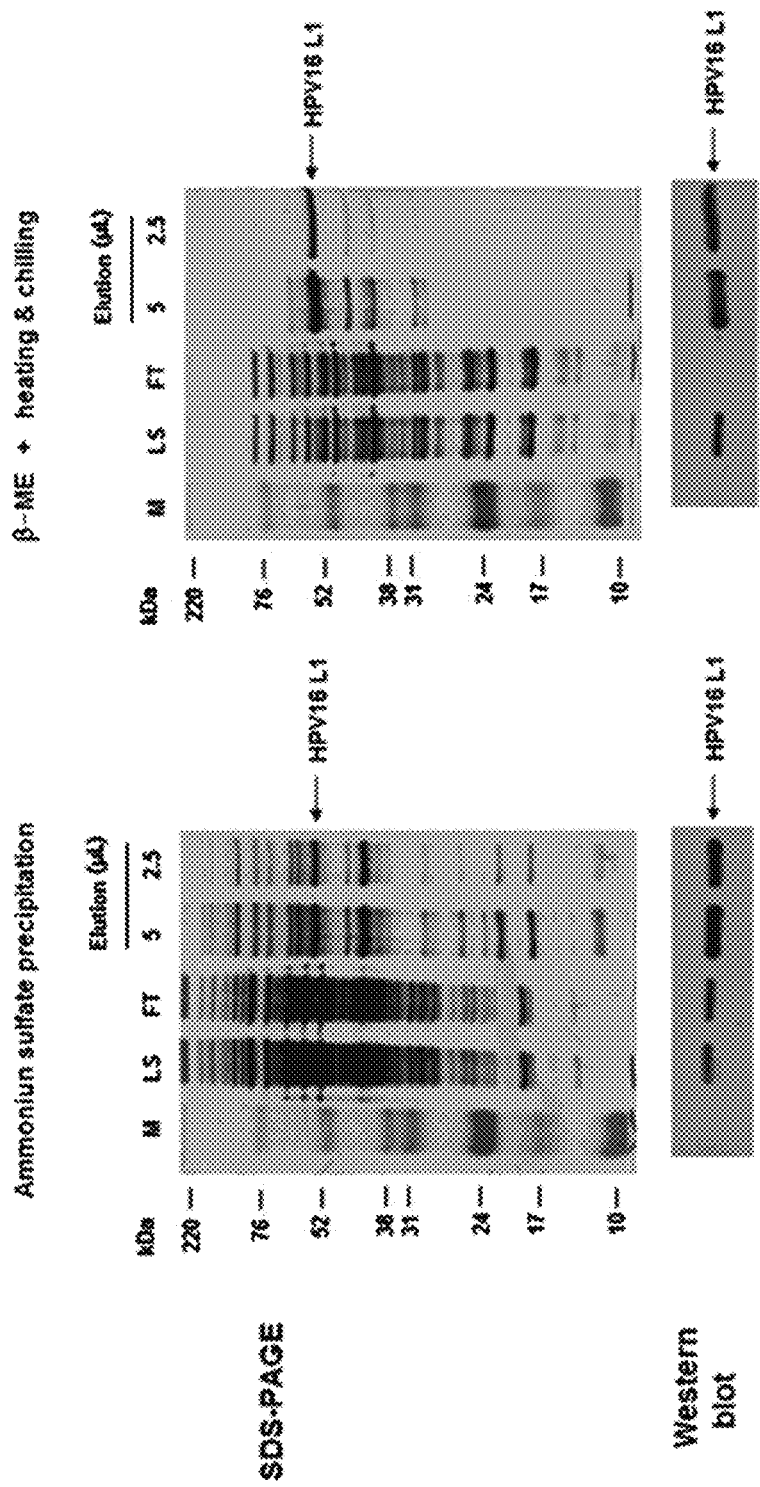

FIG. 19 shows first heparin chromatography results for the purification method according to ammonium sulfate precipitation and the purification method performed by heating and chilling after treatment with a reducing agent (T-5, β-ME +heating & chilling). Like the result shown in FIG. 18, it was confirmed that an L1 protein eluted by first heparin chromatography had a high purity in the method performed by treatment with a reducing agent and heating/chilling, whereas a plurality of contaminating proteins were included in an L1 protein fraction eluted when the first heparin chromatography was performed after ammonium sulfate precipitation. As the result of Western blotting, it was confirmed that the L1 protein was not attached to a column resin and flowed through in heparin chromatography when the L1 protein was purified by ammonium sulfate precipitation, and the L1 protein did not flow through when the L1 protein was treated with a reducing agent, and heated/chilled.

Figure 20:
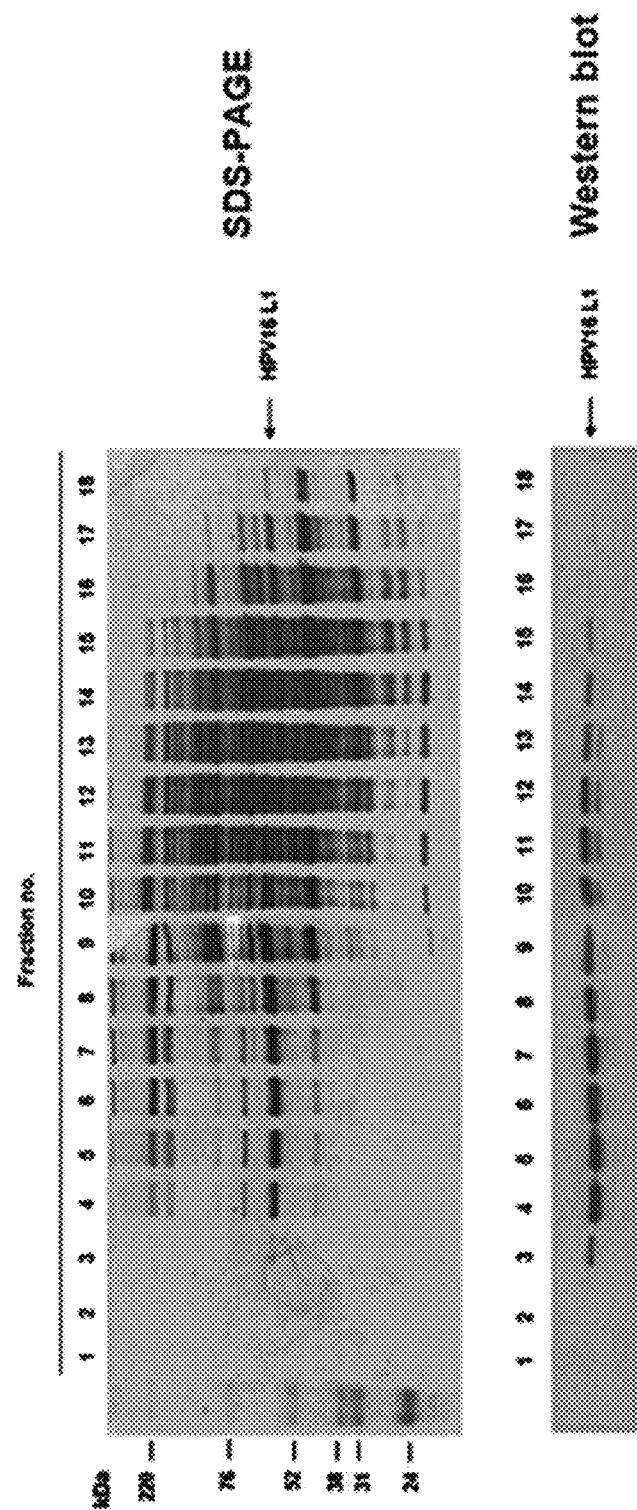

FIG. 20 shows SDS-PAGE and Western blotting results for elution fractions obtained by SEC in the purification method according to the SEC. Among the fractions 3 to 9, L1 proteins were eluted with high purity, and thus fractions in this section were collected to compare.

Figure 21:
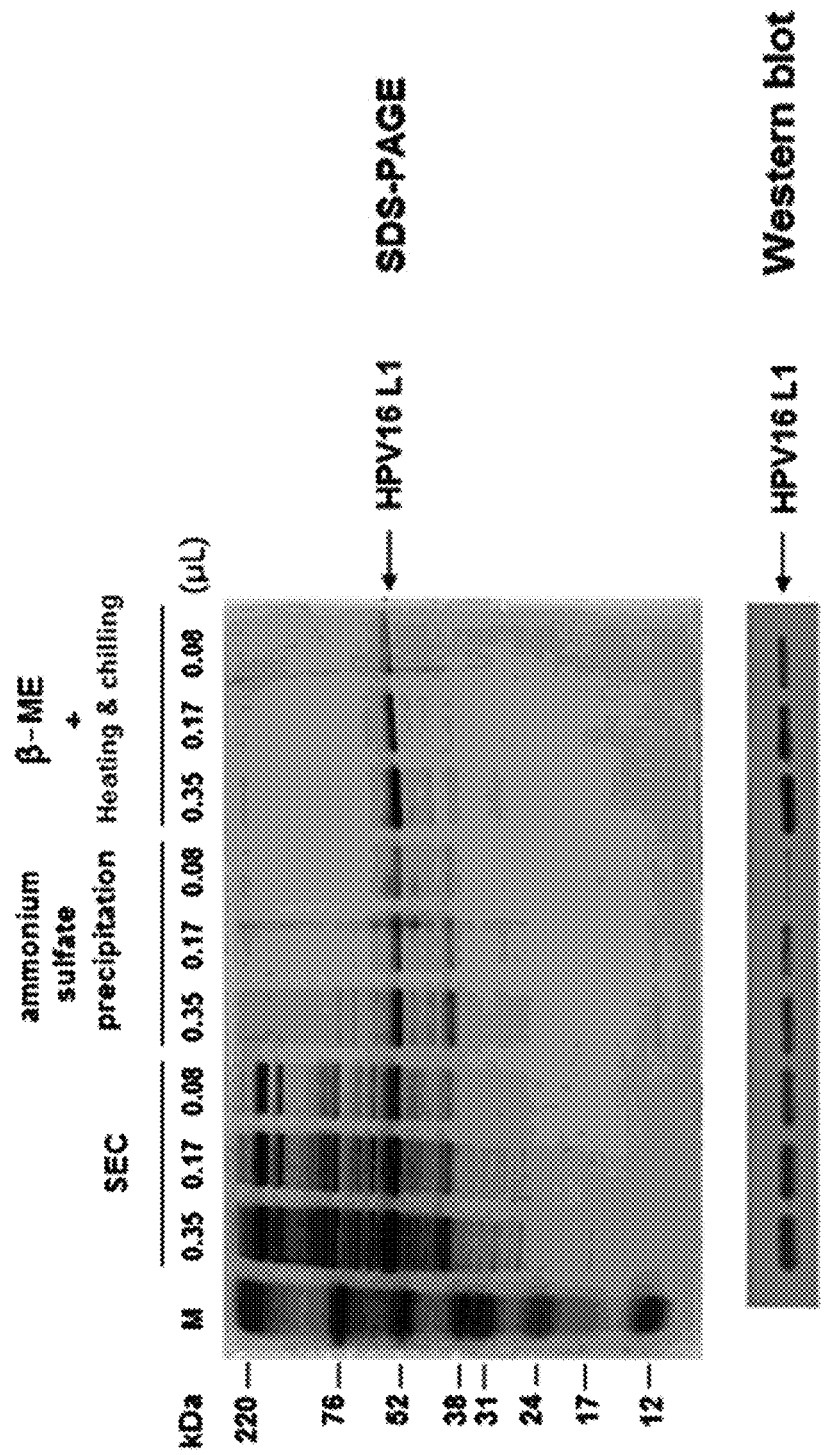

FIG. 21 shows SDS-PAGE and Western blotting results for L1 protein elution fractions obtained in first chromatography in the purification method according to SEC (SEC), the purification method according to ammonium sulfate precipitation, and the purification method performed by treatment with a reducing agent and heating/chilling (T-5, β-ME+heating & chilling). For the first chromatography, a sample for each condition was prepared as shown in FIG. 17. For the SEC, a cell homogenate went through ammonium sulfate precipitation and the SEC (first chromatography). For the method according to ammonium sulfate precipitation, the cell homogenate was subjected to the step removal of precipitated contaminants after the ammonium sulfate precipitation, and then subjected into heparin chromatography (first chromatography). For the method performed by the treatment with a reducing agent and heating/chilling, the homogenate was treated with a reducing agent, heated and chilled, and went through the heparin chromatography (first chromatography). For analysis of an elution fraction obtained by the first chromatography, a fraction for each condition was loaded at the same volume (0.35, 0.17 or 0.08 µl). According to the analysis result, it appeared that the L1 proteins obtained by the method including the treatment with a reducing agent and heating/chilling have the highest purity.

Figure 22:
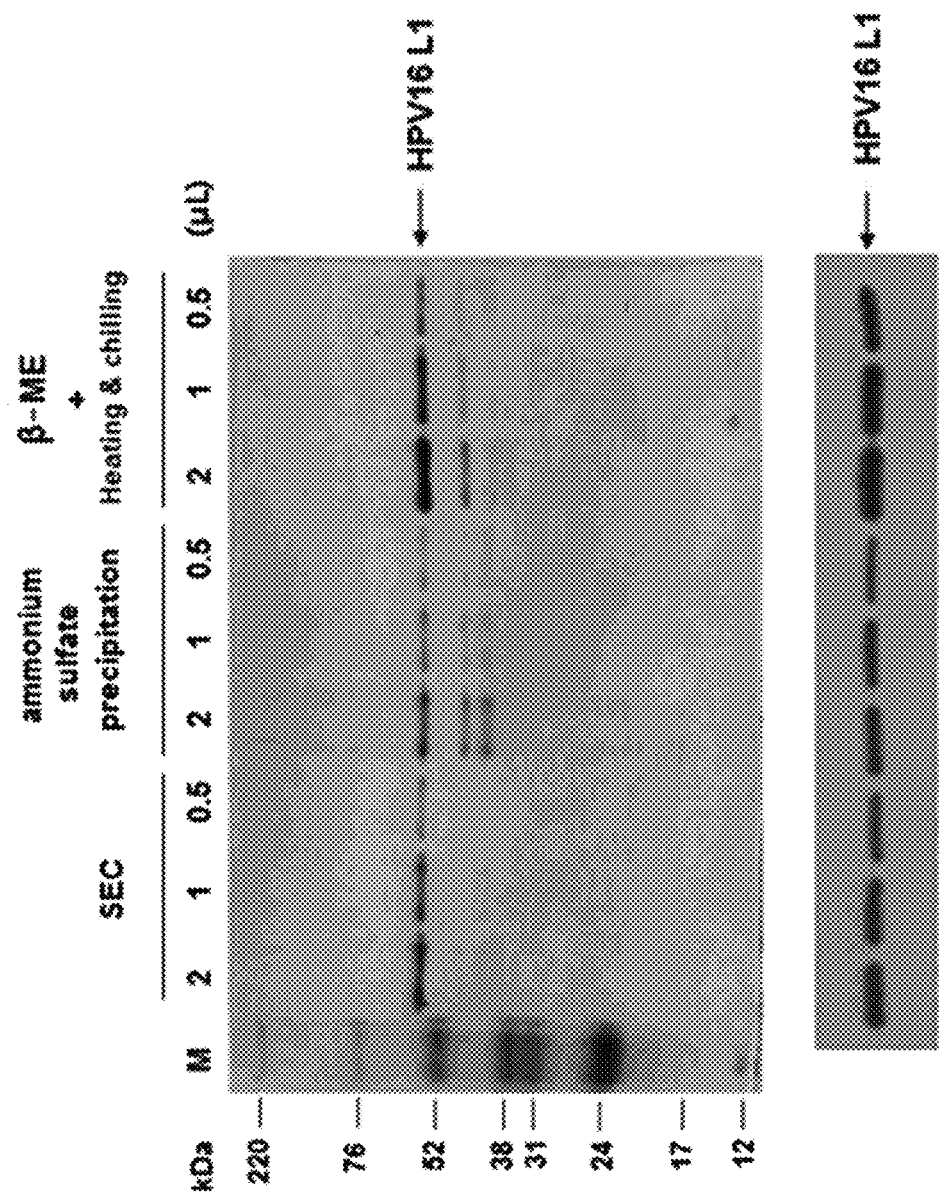

FIG. 22 shows a result obtained by further purifying the L1 protein from elution fraction obtained by the first chromatography of FIG. 21 by second chromatography. The difference between L1 protein elution fractions after the second chromatography was analyzed by SDS-PAGE and Western blotting. For analysis, an elution fraction for each purification condition was loaded at the same volume (2, 1 or 0.5 µl). According to the analysis result, it was seen that the purification method including treatment with a reducing agent and heating/chilling was the best with respect to the recovery rate of L1 protein.

Figure 23:
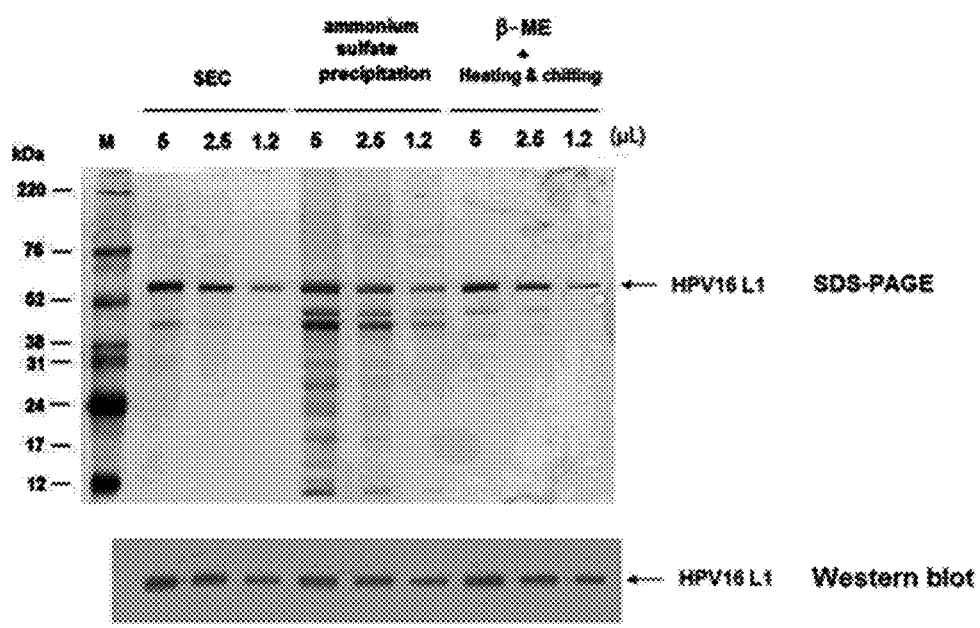
Figure 23:
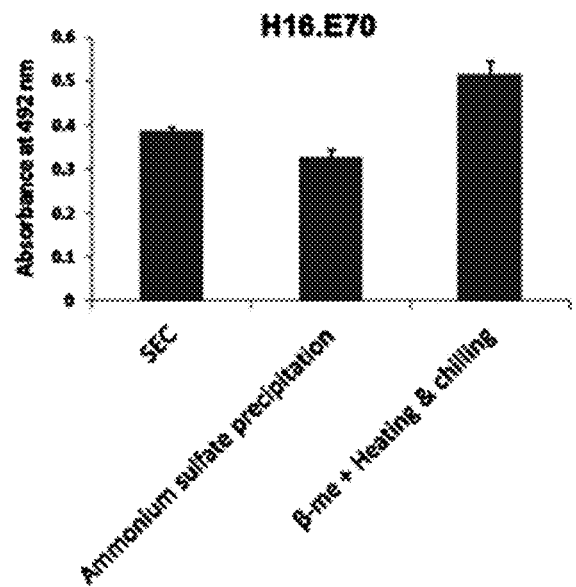

FIG. 23 shows reactivity of a monoclonal antibody (H16.E70) towards the L1 proteins finally purified in FIG. 22, which was analyzed by an enzyme-linked immunosorbent assay (ELISA). To coat HPV16 L1 VLPs obtained in each purification condition at the same amount, L1 proteins obtained from a purification method according to SEC (SEC), a purification method according to ammonium sulfate precipitation, and a purification method performed by heating and chilling after treatment with a reducing agent (β-ME+heating & chilling) were adjusted to have the same concentration, and an amount of the L1 proteins was detected by SDS-PAGE and Western blotting (FIG. 23A). Afterward, a reactivity of HPV16 L1 VLPs to H16.E70 was detected by ELISA (FIG. 23B). As a result, it was seen that the HPV16 L1 VLP purified by treatment with a reducing agent and heating/chilling (T-5 HPV16 L1 VLP) had the best reactivity towards H16.E70. This shows that HPV16 L1 VLPs obtained by the purification method performed by treatment with a reducing agent and heating/chilling have the best structural characteristic [26].

Figure 24:
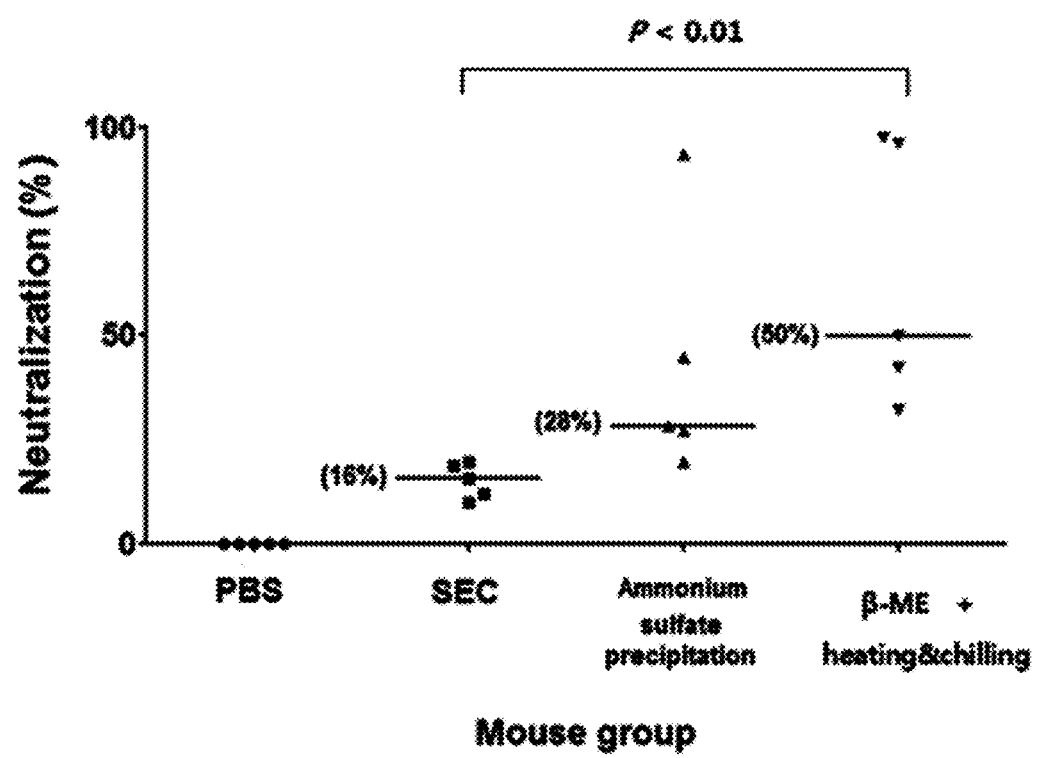

FIG. 24 shows analyses of immunogenicities of a purification method according to SEC, a purification method according to ammonium sulfate precipitation, and a purification method performed by treatment with a reducing agent and heating/chilling. An amount of L1 protein before a mouse was immunized with HPV16 L1 VLP was adjusted to the same as detected in FIG. 23A. 1 ng of HPV16 L1 VLPs was mixed with 200 μg of aluminum hydroxide, and then injected subcutaneously into the mouse. The mouse immunization was performed four times at two week intervals. After the fourth immunization, a mouse sera were taken, and a neutralizing activity of each mouse group was detected by a conventionally known pseudovirus-based method for measuring activity of neutralizing antibody [26]. As a result, it was seen that the neutralizing activity of mouse immunized with HPV16 L1 VLPs obtained by purification through size-exclusion chromatography was 16%, the neutralizing activity of mouse immunized with HPV16 L1 VLPs obtained by ammonium sulfate precipitation was 28%, and the neutralizing activity of a mouse immunized with the HPV16 L1 VLPs obtained by purification performed by treatment with a reducing agent and heating/chilling was 50%. Therefore, it appeared that the ability of HPV16 L1 VLP obtained from the purification method performed by treatment with a reducing agent and heating/chilling to induce neutralizing antibodies is the best.

Figure 25:
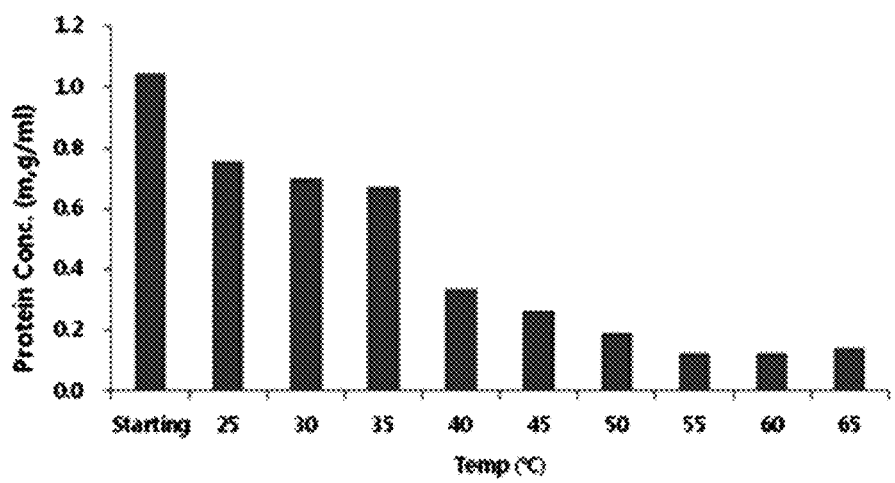
Figure 25:
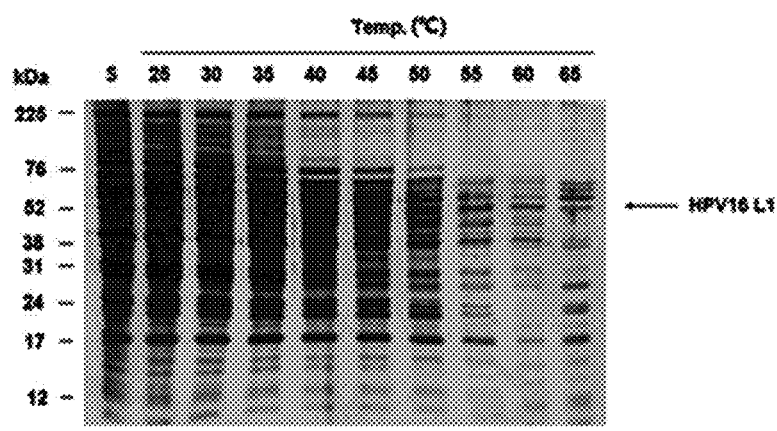
Figure 25:
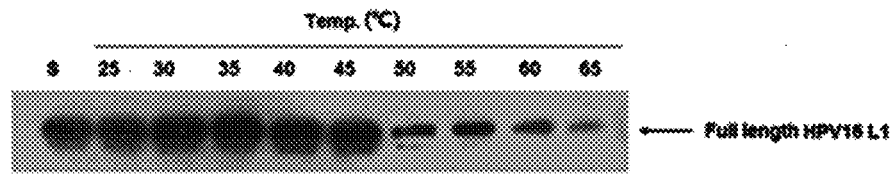
Figure 25:
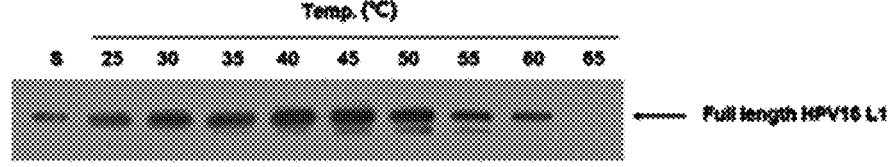

FIG. 25 shows an effect as a function of heating temperature in the process of heating/chilling after treatment with a reducing agent in T-5 method. A cell homogenate was heated at each heating temperature for 15 minutes and chilled, and then the precipitated contaminants was removed by centrifugation. Panel A shows the protein concentrations measured according to the heating temperature. Panel B shows a SDS-PAGE result for samples loaded at respective heating temperatures at the same volume. Panel C is a Western blotting result to analyze L1 proteins for samples loaded at respective heating temperatures at the same volume. Panel D is a Western blotting result to analyze L1 proteins for samples quantified at respective heating temperatures when the samples was loaded at the same protein amount. Accordingly, panel D shows a purity of the L1 proteins. According to the result, it was confirmed that HPV16 L1 proteins remained in the cell homogenate at a heating temperature of 60° C., and the purity of the L1 protein was increased when the cell homogenate was heated at 35 to 50° C.

Figure 26:
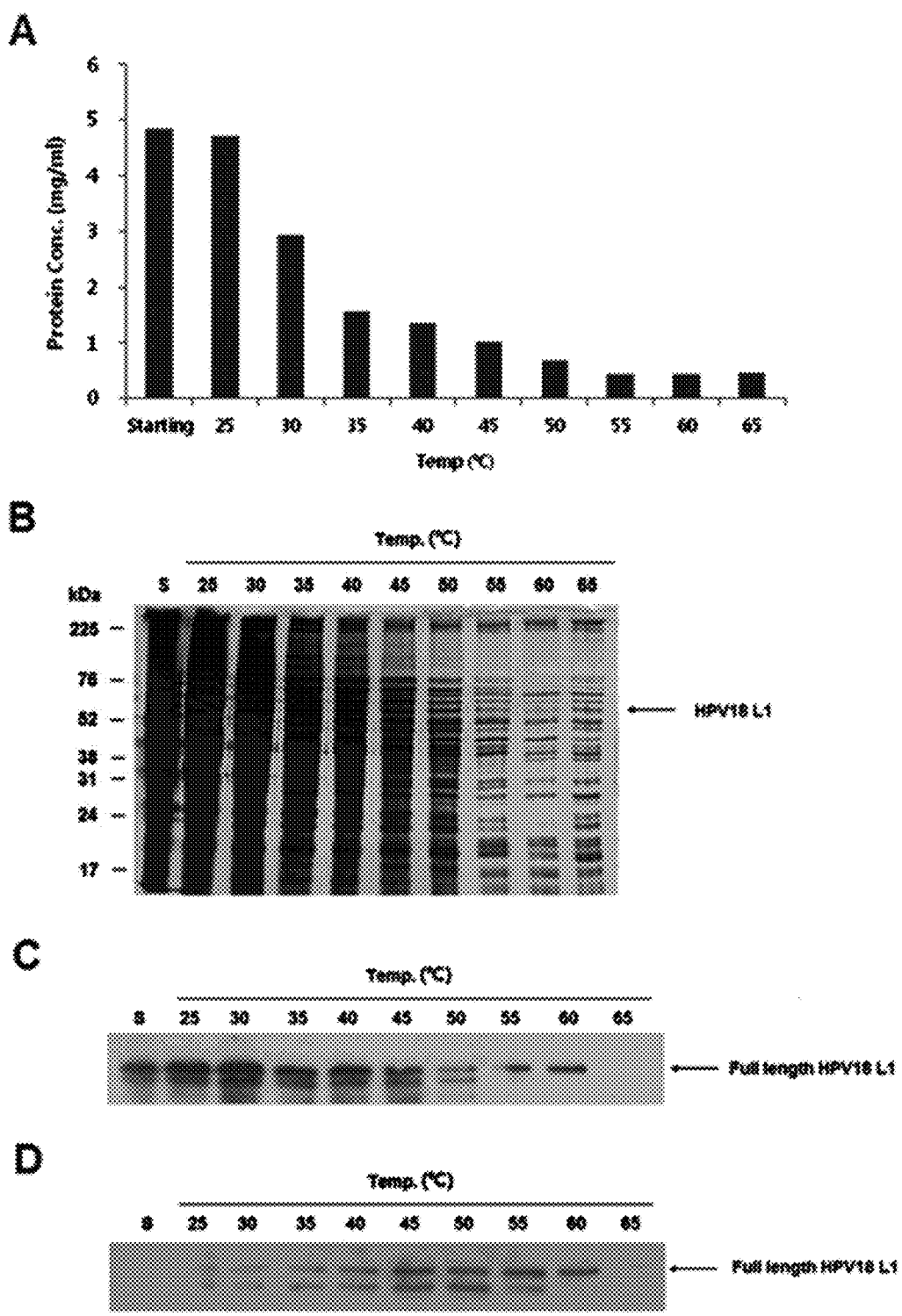

FIG. 26 shows an effect as a function of heating temperature in the step of heating/chilling after treatment with a reducing agent in the purification of HPV18 L1 proteins according to T-5 method. Detail descriptions of each panel are the same as for FIG. 25. According to the result, it was confirmed that HPV18 L1 proteins remained in the cell homogenate up to a heating temperature of 65° C., and a purity of the L1 proteins was increased when the cell homogenate was heated at 45 to 55° C.

Figure 27:
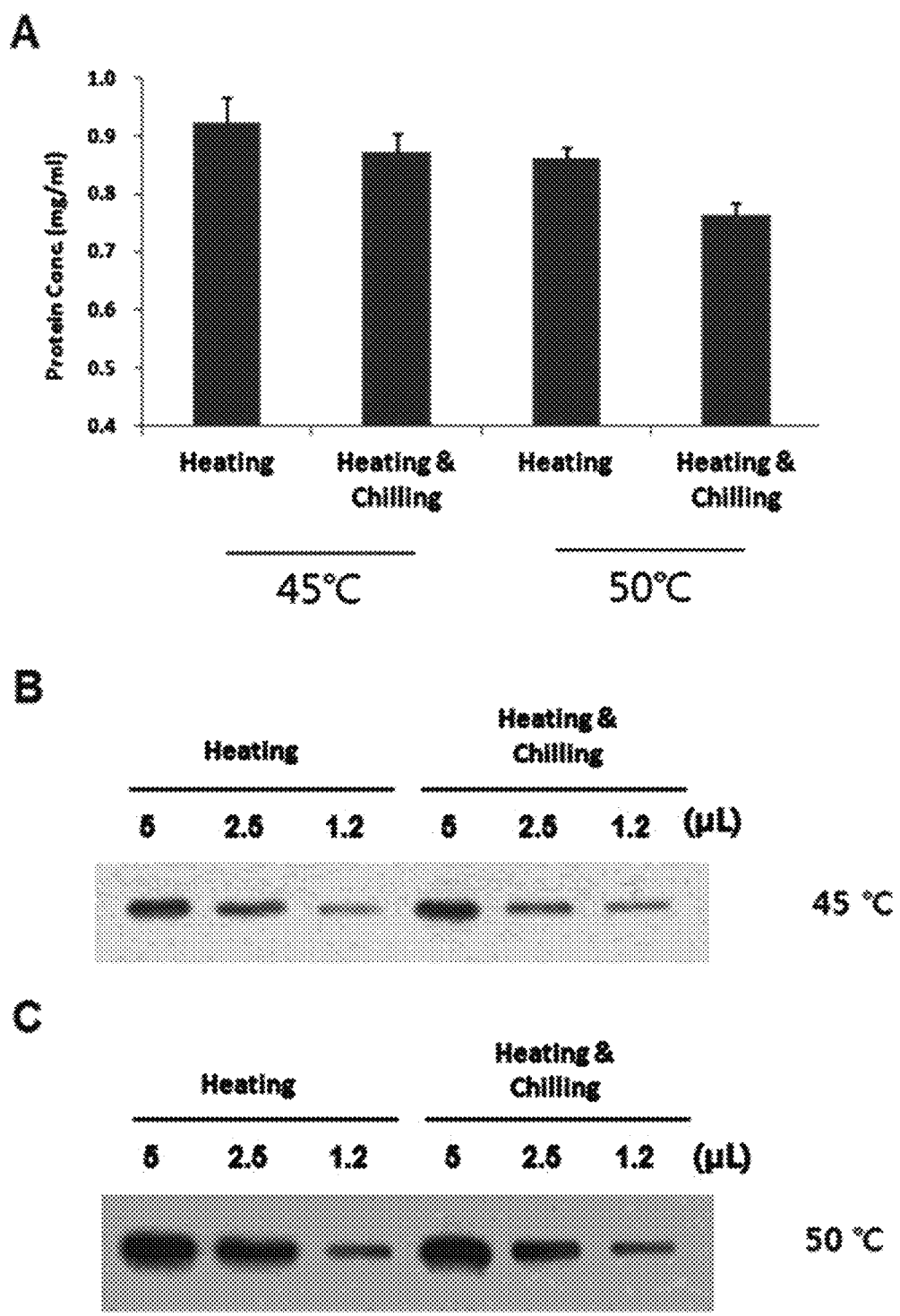

FIG. 27 shows the effect of the chilling step in heating/chilling after treatment with a reducing agent in the purification of HPV16 L1 VLP according to the T-5 method. Panel A shows a difference in protein concentration between a sample which was heated at 45 to 50° C. and chilled (heating & chilling) and a sample which was not chilled (heating). Panel B shows amounts of L1 proteins analyzed by Western blotting for a sample heated at 45° C. and chilled and a sample which was not chilled. Panel C shows amounts of L1 proteins analyzed by Western blotting for a sample heated at 50° C. and chilled and a sample which was not chilled. This result shows that contaminating proteins were removed by precipitation through the chilling step, and in this operation, loss of the L1 proteins did not occur.

Figure 28:
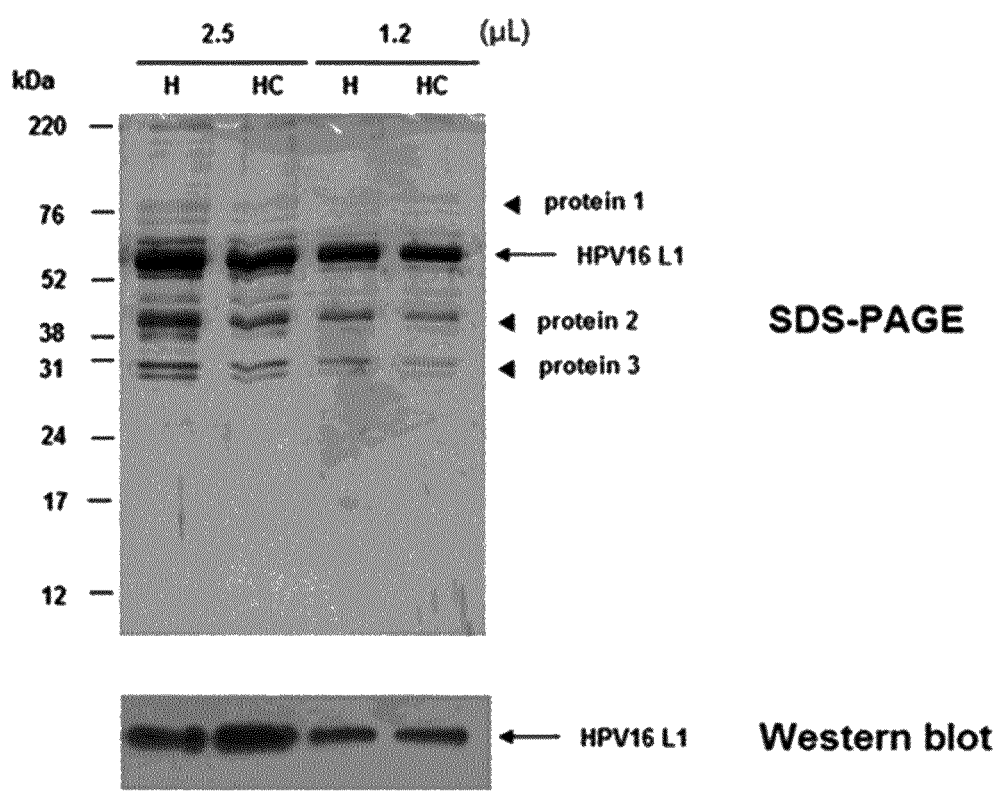

FIG. 28 shows the effect of the chilling step in heating and chilling after treatment with reducing agent in the purification of HPV16 L1 VLP according to the T-5 method. It shows a difference between a sample which was heated at 45° C. and chilled (HC) and a sample which was not chilled (H), which was analyzed by SDS-PAGE and Western blotting. According to the results of the SDS-PAGE and Western blotting, it was confirmed that the L1 proteins were not reduced after the chilling step while the contaminating proteins were reduced.

FIG. 29 shows numerical values of band intensities of contaminating proteins protein 1, protein 2 and protein 3 detected by SDS-PAGE of FIG. 28. This shows that the concentrations of the contaminating proteins were reduced by the chilling step.

Figure 30:
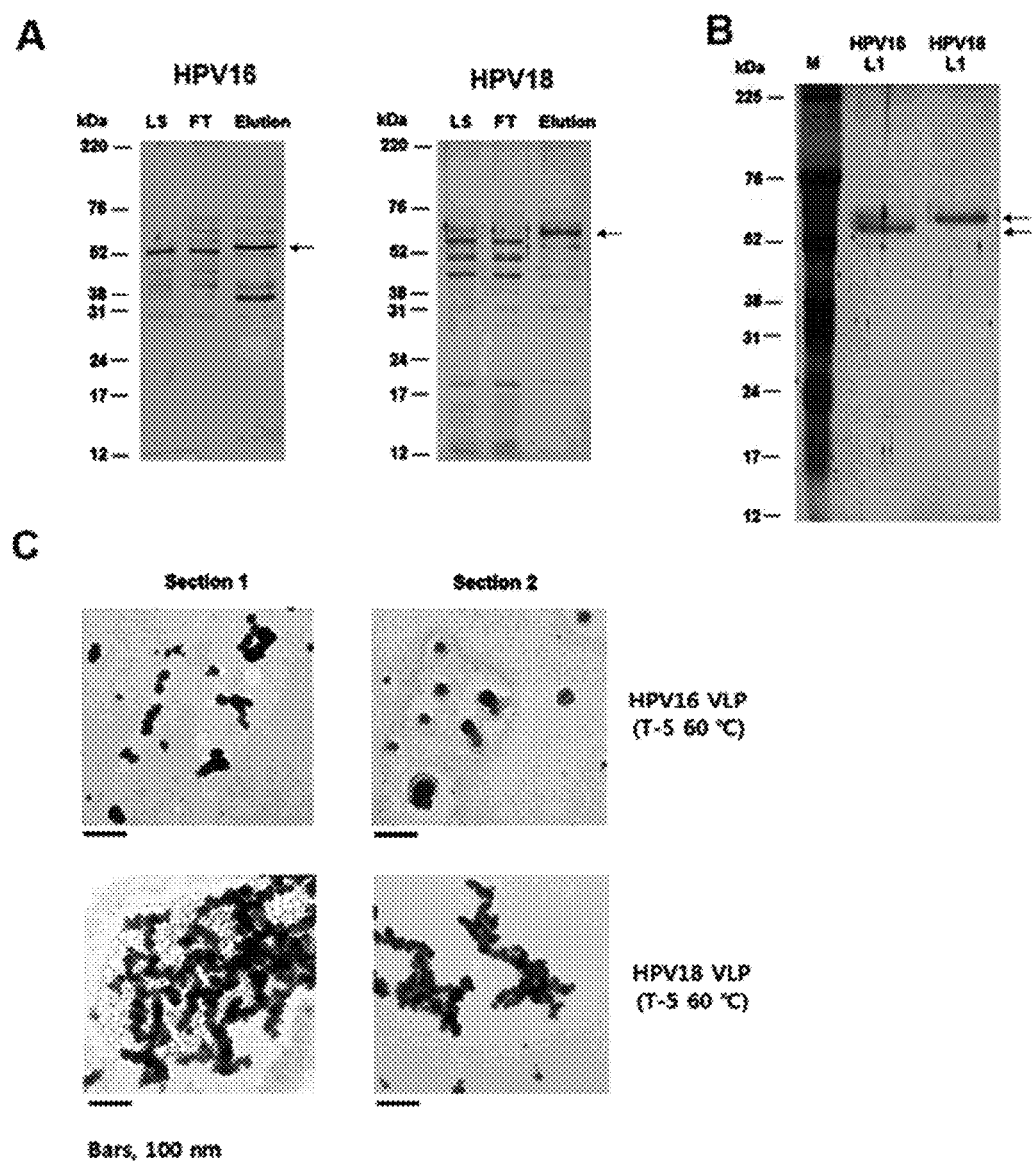

FIG. 30 shows results obtained by purifying HPV16 L1 VLPs and HPV18 L1 VLPs at a heating temperature of 60° C. according to a T-5 method. Panel A shows an SDS-PAGE result for first chromatography. LS indicates a sample loaded onto a column, and FT indicates a sample flowing through without being bound to a column. Elution indicates a fraction eluted after binding to a column resin. Arrows indicate locations of HPV16 L1 and HPV18 L1. Panel B shows SDS-PAGE results for HPV16 L1 and HPV18 L1 finally purified after performing the first and second chromatography. Panel C is a transmission electron microscopy for a product finally purified. According to the electron microscopy result, it was confirmed that purified L1 proteins form VLPs.

Figure 31:
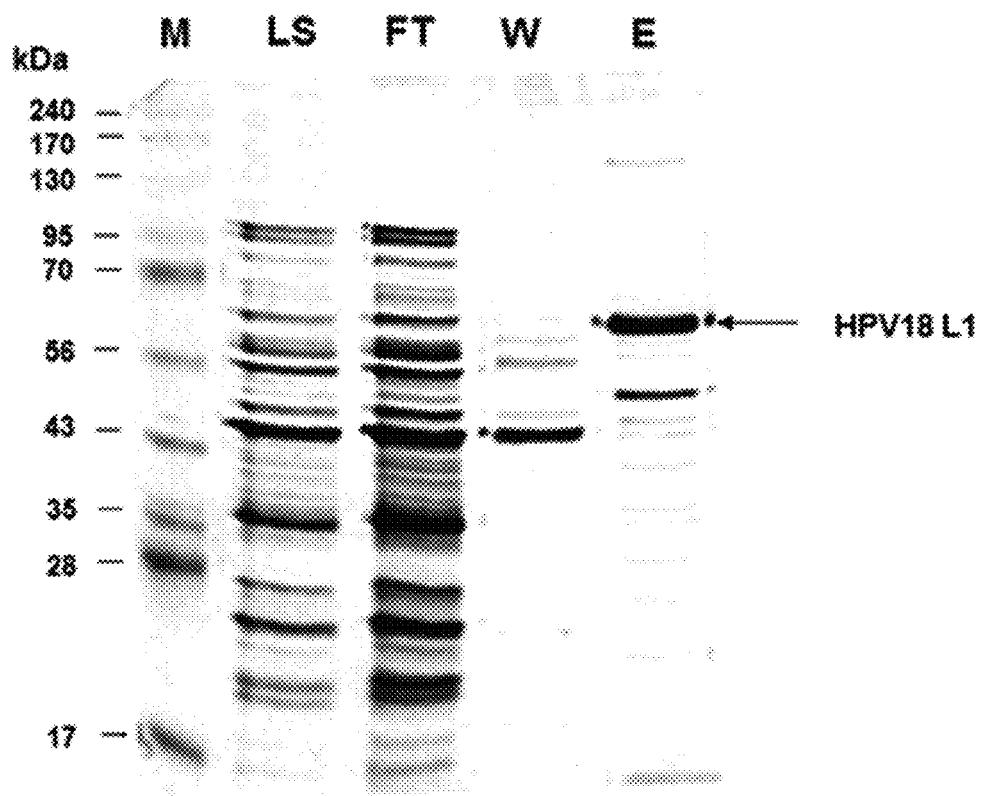

FIG. 31 shows a result obtained by purifying HPV18 L1 by first chromatography according to a T-5 method. Each fraction was analyzed by SDS-PAGE. LS indicates a loading sample, FT indicates a flow-through, W indicates a fraction while a column is being washed, and E indicates a fraction of protein, which was attached to a column, eluted by addition of a buffer solution including 1M NaCl. It was shown that HPV18 L1 was purified with high purity by chromatography after treatment with a reducing agent and heating/chilling.

Figure 32:
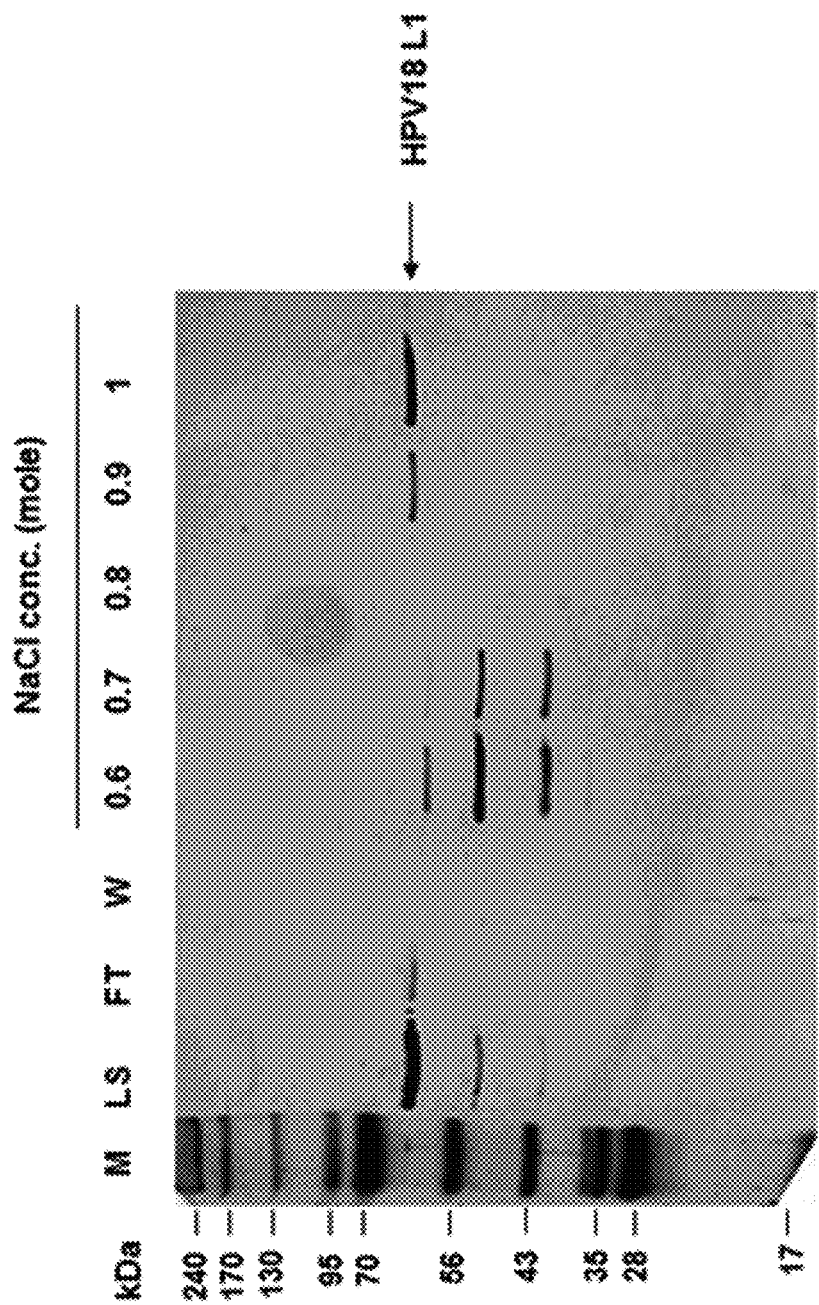

FIG. 32 shows a SDS-PAGE result for a HPV18 L1 protein fraction eluted after second cation-exchange chromatography that was performed using elution fraction of first chromatography of FIG. 31. LS, FT and W are the same as described above. Proteins attached to a column resin were sequentially eluted with a buffer solution containing 0.6, 0.7, 0.8, 0.9 or 1M NaCl. It was confirmed that the HPV18 L1 proteins were eluted in 0.9 M and 1 M NaCl fractions.

Figure 33:
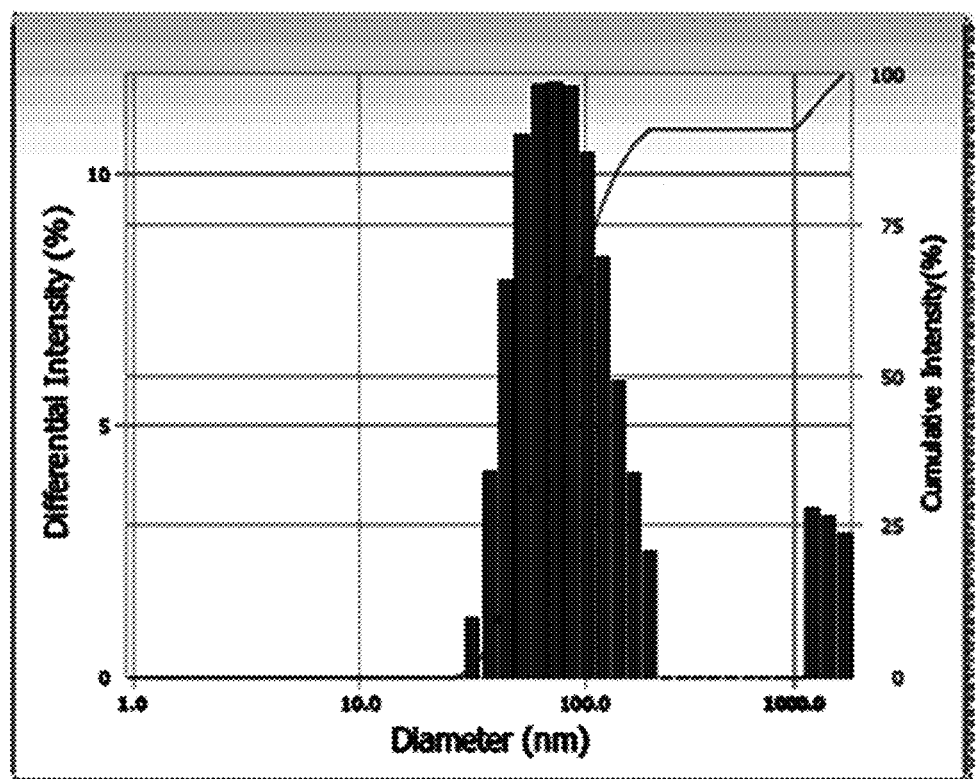

FIG. 33 shows a DLS result for HPV18 L1 VLPs purified by a T-5 method. The DLS of the T-5 HPV18 L1 VLPs was analyzed using an ELS-Z2 system.

Figure 34:
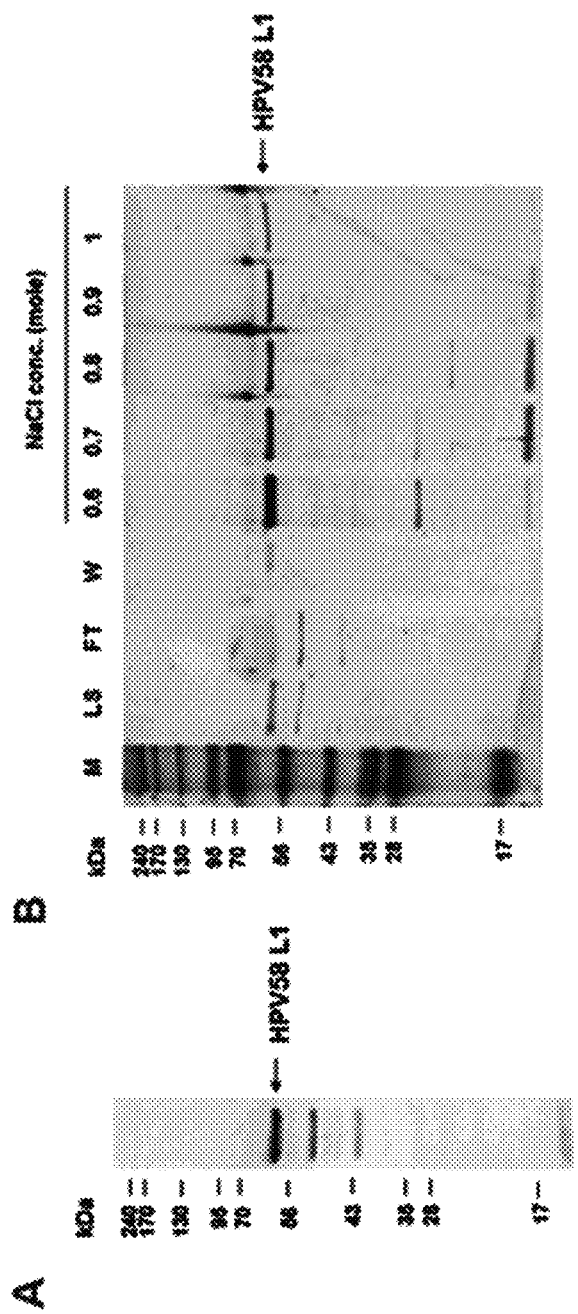

FIG. 34 shows results obtained by purifying HPV58 L1 by a T-5 purification method. Panel A shows an SDS-PAGE result for an L1 protein fraction eluted by first chromatography. Panel B shows an SDS-PAGE result for second chromatography. Detailed description of Panel B is the same as described in FIG. 32.

Figure 35:
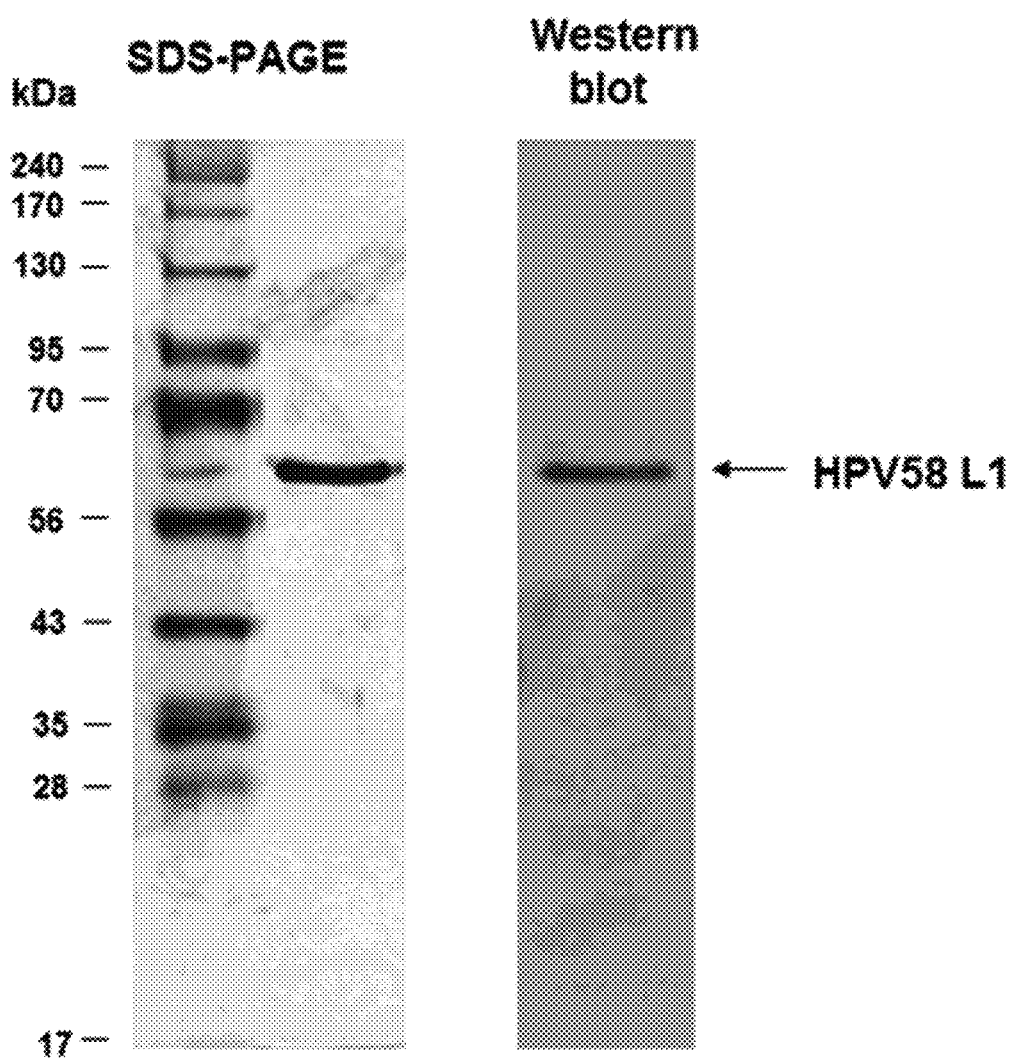

FIG. 35 shows SDS-PAGE and Western blotting results for HPV58 L1 proteins finally recovered by first and second chromatographies according to a T-5 purification method. It shows that HPV58 L1 can be successfully purified by a method for treating with reducing agent followed by performing heating/chilling steps.

FIG. 36 shows a DNA sequence coding for an HPV16 L1 protein (HPV16 L1 NG2). *Saccharomyces cerevisiae* was transformed with expression vector harboring the HPV16 L1 NG2 gene. The transformed cells were used to express and purify the HPV16 L1 protein. A nucleic acid sequence of HPV16 L1 was noticed as accession no. KC792555.1 of GenBank.

FIG. 37 shows a DNA sequence coding for an HPV18 L1 protein (HPV18 L1 NG3). *Saccharomyces cerevisiae* was transformed with expression vector harboring the HPV18 L1 NG3 gene. The transformed cells were used to express and purify the HPV18 L1 protein. A nucleic acid sequence of HPV18 L1 was noticed as accession no. KC792556.1 of GenBank.

FIG. 38 shows amino acid sequences of HPV16 L1 and HPV18 L1 encoded by the HPV16 L1 NG2 and HPV18 L1 NG3, respectively.

MODES OF THE INVENTION

Hereinafter, the present invention will be described in further detail with reference to examples. The examples are merely provided to explain the present invention in further detail, and the scope of the present invention is not limited to examples, but it will be clearly understood by those of ordinary skill in the art that the scope of the present invention is not limited to examples according to the gist of the present invention.

EXAMPLES

Method of Experiment
1. Cell Culture

*Saccharomyces cerevisiae* (*S. cerevisiae*) Y2805 expressing an HPV L1 protein was cultured according to a conventionally known method [25]. HPV L1 protein-expressing cells were plated on a uracil-free synthetic complete medium, that is "SD-ura", and cultured for four or five days. A single colony inoculated an SD-ura liquid medium and was cultured for two days. To express an HPV 16 L1 protein from a GAL10 promoter, the cultured transformed cells were cultured in an YPDG medium containing 1% yeast extract (Duchefa, Netherlands), 2% peptone (Duchefa), 7% glucose (Duchefa) and 1% galactose (Duchefa). After the culture, the cultured cells were centrifuged to remove the medium, and washed with phosphate-buffered saline (PBS). The washed cells were harvested by centrifugation again, and stored at −70° C. before the purification of the protein.

2. Purification of HPV VLPs Using T-1 Method

Purification of HPV VLPs according to a T-1 method was performed by heparin chromatography after proteins in a homogenate were recovered by ammonium sulfate precipitation as a pellet according to a conventionally-known method [22,23,24]. For the heparin chromatography, a HiTrap™ Heparin HP (GE Healthcare, USA) resin was used. A sample recovered from the steps for removing ammonium sulfate and removing precipitated contaminants was dialyzed against PBST containing 0.325 M NaCl, and passed through a heparin resin equilibrated with PBST containing 0.325 M NaCl. The heparin resin was washed with five resin-bed volumes of the buffer (PBS containing 0.325 M NaCl), and the proteins bound with the resin were eluted by linear gradient to increase the concentration of NaCl from 0.325 to 2 M. Among elution fractions, those including HPV L1 were selected by SDS-PAGE. The purified HPV L1 VLPs were dialyzed against PBS containing 0.01% Tween 80 and 0.33 M NaCl (PBST).

3. Purification of HPV VLP by T-5 Method (β-me+ Heating & Chilling Method)

3-1. Cell Disruption, Treatment with Reducing Agent and Heating/Chilling

Cultured HPV L1 protein-expressing cells were mixed in a disruption buffer solution (10 mM sodium phosphate dibasic, 150 mM NaCl, 1.7 mM EDTA, 0.01% Tween 80 pH 7.2). The cell mixture was mixed again with 0.5 mm glass beads (Biospec Product, USA), and the cells were disrupted by vortexing. Cell debris was removed by centrifugation at 12000×g for 15 minutes. Before column chromatography, cell lysates were prepared by two different methods. The first method includes adding β-ME to the cell lysate to have a final concentration of β-mercaptoethanol (β-ME, Sigma, USA) of 4 to 6 wt %, and adjusting pH to 7.0 to 7.3. The second method includes dialyzing the cell homogenate against the cell disruption buffer solution (10 mM sodium phosphate dibasic, 150 mM NaCl, 1.7 mM EDTA, 0.01% Tween 80 pH 7.2) for 4 to 6 hours, and adding β-ME to the cell lysate to have a final concentration of β-ME ranging 4-6%. Subsequently, the β-ME-added cell lysate was stayed in a constant temperature water bath at 25 to 65° C. for 30 to 50 minutes, and chilled on ice for 30 minutes to 3 hours or at 4° C. for 16 hours. The chilled cell lysate was centrifuged at 12000×g for 15 minutes to remove precipitated contaminants.

3-2. First Chromatography

A cell lysate prepared by heating and chilling after treatment with reducing agent was passed through a heparin resin (HiTrap™ Heparin HP, GE Healthcare, USA or POROS® 50 HE, Applied Biosystems, USA) or a cation-exchange resin (POROS® XS, Applied Biosystems, USA). Before the cell homogenate was passed through the heparin resin or cation-exchange resin, the resin was equilibrated with a disruption buffer solution (10 mM sodium phosphate dibasic, 0.15 to 0.48 M NaCl, 1.7 mM EDTA, 0.01% Tween 80, pH 7.2) containing 4 to 6% β-ME. The cell homogenate was loaded onto a resin, and heparin or cation exchange resin was washed with five or more than five resin-bed volumes of wash buffer (PBST containing 0.35 to 0.48 M NaCl and 5% β-ME). The HPV L1 proteins bound with heparin resin were eluted with PBST containing 1M NaCl and 5% β-ME, or by successive addition of buffer solutions prepared to have final NaCl concentrations of 0.6 M, 0.7 M, 0.8 M, 0.9 M and 1 M in PBST containing 5% β-ME. The elution solution including L1 proteins was concentrated using Amicon Ultra (Millipore, USA), and dialyzed against PBST containing 1 M NaCl and 0.2 M ammonium sulfate for 20 to 24 hours.

3-3. Second Chromatography

The solution dialyzed after the first chromatography was additionally dialyzed against PBST containing 0.3 to 0.42 M NaCl, passed through a heparin resin or a cation-exchange resin to perform the second chromatography. A heparin resin or a cation-exchange resin used for the second chromatography were the same as those used in the first chromatography. The heparin/cation exchange resin was equilibrated with PBST containing 0.42 M NaCl prior to sample loading. After the sample loading, the resin was washed with five or more than five resin-bed volumes of PBST containing 0.42 M NaCl. HPV L1 proteins bound with the heparin/cation exchange resin were eluted by increase of concentration of NaCl from 0.42 to 2.0 M, or by successive addition of buffer solutions prepared to have concentrations of NaCl of 0.6 M, 0.7 M, 0.8 M, 0.9 M and 1 M. An elution pattern for the chromatography was monitored at a wavelength of 280 nm, and collected using an Autochro-2000 program (Young Lin Instrument Co., South Korea). An L1 protein-eluted fraction was collected, concentrated using Amicon Ultra (Millipore, USA), and dialyzed against PBST containing 0.33 M NaCl.

4. Non-Treatment Method

For non-treatment purification, cells were prepared by disruption as described above. The prepared homogenate was dialyzed against a buffer solution (10 mM sodium phosphate dibasic, 150 mM NaCl, 1.7 mM EDTA, 0.01% Tween 80 pH 7.2) for 4 to 6 hours. Precipitated contaminants of the dialyzed sample were removed by centrifugation at 12000×g for 10 minutes, and then the preparation passed through a heparin resin equilibrated with the buffer solution above. Afterward, the heparin resin was washed with five resin-bed volumes of PBST containing 0.42 M NaCl, and proteins bound with the heparin resin were eluted with PBST containing 1 M NaCl after the wash step.

5. Purification Method by Treating with β-me (β-me Method)

A purification method by treating with β-me is a purification method excluding heating & chilling step from the T-5 purification method. For the purification method by treating with β-me, cells expressing HPV L1 were prepared as described above, and dialyzed against a buffer solution (10 mM sodium phosphate dibasic, 150 mM NaCl, 1.7 mM EDTA, 0.01% Tween 80 pH 7.2) for 4 to 6 hours. β-me was added to the dialyzed lysate to have a final concentration of 4 to 6% of β-me. The heparin resin was equilibrated with a buffer solution (10 mM sodium phosphate dibasic, 150 mM NaCl, 1.7 mM EDTA, 0.01% Tween 80 pH 7.2) containing 4 to 6% β-me, and the prepared homogenate passed through the resin. The heparin resin through which the lysate passed was washed with five resin-bed volumes of PBST containing 4 to 6% β-me and 0.42 M NaCl. Proteins attached to the heparin resin were eluted with PBST containing 4 to 6% β-me and 1 M NaCl.

6. Heating & Chilling Method

A heating & chilling method is a purification method excluding the β-me treatment step from a T-5 purification method. For purification of HPV L1 proteins, cells were disrupted and dialyzed against a buffer solution (10 mM sodium phosphate dibasic, 150 mM NaCl, 1.7 mM EDTA, 0.01% Tween 80 pH 7.2) for 4 to 6 hours. The dialyzed lysate was treated at 37 to 45° C. for 30 minutes, and chilled on ice for 30 minutes to 3 hours. Precipitated contaminants of the lysate subjected to heating/chilling were removed by centrifugation at 12000×g for 10 minutes, and passed through a heparin resin equilibrated with a buffer solution (10 mM sodium phosphate dibasic, 150 mM NaCl, 1.7 mM EDTA, 0.01% Tween 80 pH 7.2). Afterward, the heparin resin was washed with 5 resin volumes of PBST containing 0.42 M NaCl, and proteins bound with the resin after washing step were eluted with PBST containing 1 M NaCl.

7. Purification Using Size-Exclusion Chromatography (SEC)

Purification using SEC was performed by slight modification of a conventionally known method [20]. HPV L1 expression yeasts were prepared by disruption as described above, and proteins were precipitated by saturating 45% ammonium sulfate. The precipitated proteins were resuspended using PBST, and dialyzed against a buffer solution (10 mM sodium phosphate dibasic, 0.65M NaCl, 1.7 mM EDTA, 0.01% Tween 80 pH 7.2) for 4 hours. Purification of the dialyzed fraction was performed by SEC as first chromatography. The prepared sample passed through a superose-6 resin (1.5×32 cm, GE Healthcare, USA) equilibrated with PBST containing 0.65 M NaCl (first chromatography) [36]. An elution pattern of the SEC was detected with a wavelength of 280 nm, and collected using an Autochro-2000 program (Young Lin Instrument Co., South Korea).

Fractions containing HPV L1 were collected, dialyzed against PBST containing 0.33 M NaCl, and passed through a heparin resin equilibrated with PBST containing 0.33 M NaCl (second chromatography). Afterward, the heparin resin was washed with five resin-bed volumes of PBST containing 0.42 M NaCl. After washing, proteins bound with the heparin resin were eluted by sequentially flowing PBST containing 0.6 M, 0.7 M, 0.8 M, 0.9 M, and 1 M NaCl.

8. Purification Using Ammonium Sulfate Precipitation (Ammonium Sulfate Precipitation Method)

Purification using ammonium sulfate precipitation is a method in which heating & chilling step after β-me treatment in T-5 method is replaced with ammonium sulfate precipitation. Before chromatography, ammonium sulfate precipitation and removal of precipitated contaminants were performed according to a conventionally known method [22, 24]. Proteins in a cell lysate were saturated with 45% ammonium sulfate to precipitate, and contaminating substances were removed (removal of precipitated contaminants). A sample prepared above before chromatography was dialyzed against a buffer solution (10 mM sodium phosphate dibasic, 150 mM NaCl, 1.7 mM EDTA, 0.01% Tween 80 pH 7.2) for 4 hours. A heparin resin was equilibrated with the same buffer solution as used above, and then the dialyzed sample passed through the resin (first chromatography). Afterward, the resin was washed with five resin-bed volumes of PBST containing 0.42 M NaCl, and binding proteins were eluted with PBST containing 1 M NaCl. For second chromatography, an elution fraction was dialyzed against a buffer solution containing 0.33 M NaCl. Afterward, the second chromatography of the SEC was performed in the same manner as described above.

9. Quantification of Protein

A concentration of proteins was measured with bovine serum albumin (BSA; Pierce, USA) as a standard by a protein quantification kit (Bio-Rad Laboratories, USA).

10. SDS-PAGE and Western Blotting

SDS-PAGE was performed according to a Laemmli's method [35], and Western blotting was performed by a known method [26]. A protein developed on an SDS-PAGE gel was visualized by staining. An HPV L1 protein was detected using a rabbit anti-HPV 16 L1 serum as a primary antibody and a goat HRP-conjugated anti-rabbit IgG polyclonal antibody (HRP-conjugated goat anti-rabbit IgG, Bethyl, USA) as a secondary antibody [26]. A band intensity was measured by National Institute Health (NIH) open source software Image J, and estimated according to a known method [25].

11. Electron Microscopy

Purified HPV 16 L1 proteins were adsorbed onto a carbon-coated grid, and stained with phosphotungstic acid or uranyl acetate. A transmission electron microscope image was taken using TEM200CX (JEOL, Japan) at a final magnification of 150,000×.

12. Dynamic Light Scattering (DLS) for HPV VLPs

DLS for HPV VLPs was performed by a known method [26]. Purified HPV VLPs were diluted in PBST containing 0.13 M NaCl to have a concentration of 0.13 mg/ml, and analyzed using a DLS-700 system (Otsuka Electronics, Japan) or an ELS-Z2 system (Otsuka Electronics, Japan).

13. Analysis of Monoclonal Antibody Reactivity Towards HPV VLPs

A reactivity of a monoclonal antibody to HPV VLPs was analyzed according to a conventionally known method [26]. A 96-well enzyme-linked immunosorbent assay (ELISA) plate was coated with 400 ng of purified HPV VLPs. The HPV L1 VLPs purified by different methods were used as coatings after SDS-PAGE was performed to confirm that an amount of L1 proteins of HPV L1 VLPs purified in each method was quantitatively the same. The VLP-coated plate was blocked with PBS-T$_{20}$ containing 3% bovine serum albumin (PBS containing 0.05% Tween 20) at room temperature for 2 hours. Anti-HPV16 L1 monoclonal antibodies, H16.V5 and H16.E70, were diluted with PBS-$T_{20}$ containing 0.3% bovine serum albumin to have concentrations of 0.25 μg/ml, 0.12 μg/ml, 0.06 μg/ml, 0.03 μg/ml, and 0.015 μg/ml, and reacted with the coated HPV VLPs at 37° C. for 90 minutes. The resulting antibodies were washed with PBS-T three times, a HRP-conjugated anti-mouse IgG antibody (Bethyl, USA) was diluted in PBS-$T_{20}$ containing 0.3% bovine serum albumin at a ratio of 1:5000, and reacted on a plate at 37° C. for 40 minutes. The plate was washed with PBS-$T_{20}$ five times, and a color reaction was performed. The color reaction was performed using o-phenylenediamine (Sigma, USA), and an optical density was detected at 492 nm.

14. Mouse Immunization with Purified HPV L1 VLP and Evaluation of Immunogenicity To evaluate immunogenicity of HPV16 L1, a 6-week old Balb/c mouse was used (Orientbio. South Korea). To immunize mice with HPV L1 proteins, purity and concentration of a L1 protein were confirmed according to the known protein quantification method and SDS-PAGE method. The mouse was immunized by subcutaneous injection four times at two week intervals. For a single immunization, 1 ng of L1 protein in combination with 200 μg aluminum hydroxide (Sigma, USA) was injected subcutaneously. 1 ng of a protein was based on a quantification result for T-5 HPV16 L1 VLPs. HPV16 L1 protein purified by another method was quantified using T-5 HP16 L1 as a standard substance. 10 days after the third and fourth immunizations, blood was collected from a vein of a mouse tail. To collect a serum, the mouse blood was centrifuged at 12000×g for 10 minutes to prepare a supernatant, and the supernatant was stored at −70° C. until measurement of antibody titer and evaluation of activity of neutralizing antibody. A titer of an anti-HPV16 L1 IgG antibody and anti-HPV16 neutralizing activity in the mouse blood were measured by ELISA and pseudovirus-based neutralization assay according to a known method [26].

15. Statistic Analysis

Statistical significance of a difference between groups was determined using a two tailed Student's t-test. P<0.05 was considered as a significant difference.

Experiment Results

1. T-5 Purification: Result of L1 Protein Purification by First Chromatography

A T-5 purification process is shown in FIG. 1. Loading samples for first heparin chromatography were prepared into two types including the case in which dialysis was performed and the case in which dialysis was not performed. In the case in which the dialysis was performed, after cells were disrupted, dialysis was performed in a cell disruption buffer solution, and then a reducing agent (β-ME) was added, and when dialysis was not performed, a reducing agent was directly added to the homogenate. Afterward, two samples were heated at 37 to 42° C., and left on ice for 30 to 50 minutes to chill down to approximately 0° C. A contaminating substances precipitated resulting from the heating/chilling step were removed, and heparin chromatography was performed. FIGS. 2 and 3 show heparin chromatography results for the dialyzed sample and the non-dialyzed sample, which were analyzed by SDS-PAGE. It appeared that L1 proteins were obtained with high purity in both cases.

2. T-5 Purification: Results of Purification of L1 Proteins by Second Chromatography The L1 protein elution fraction obtained from the first heparin chromatography was further purified by second heparin chromatography. FIG. 4a shows a purified result obtained by the second heparin chromatography. The L1 proteins bound with a heparin resin were eluted by linearly increasing of a NaCl gradient (FIG. 4b). As the result of SDS-PAGE, L1 proteins flowing through without being bound to the heparin resin were not observed in an FT fraction. It was confirmed that the L1 proteins bound with the heparin resin were eluted by an increase in the linear gradient (Fractions 11-17). FIG. 4b shows eluted substances detected at a wavelength of 280 nm in the heparin chromatography. When considering the SDS-PAGE result, the eluted proteins were not observed in FT (flow-through), but, when detected at 280 nm, it was confirmed that a considerable amount of substances was flowed through in the FT. Accordingly, it was confirmed that contaminating substances, other than the L1 proteins, were removed by the second heparin chromatography.

3. Analysis of Purities of HPV16 L1 VLPs Separated by T-1 and T-5 Methods

A purity of L1 protein collected by the second heparin chromatography (T-5 HPV16 L1 VLP) was compared with a purity of L1 proteins purified by the conventionally known method [22.24] (T-1 HPV16 L1 VLP). The T-1 purification method is shown in FIG. 1, and an SDS-PAGE result for heparin chromatography of the T-1 purification method is shown in FIG. 5. In FIG. 5, LS indicates a sample loaded onto a column (loading sample). According to the heparin chromatography of the T-1 method, L1 proteins were eluted by linear gradient increasing a concentration of NaCl from 0.325 M to 2 M, and the L1 proteins were eluted between fractions 11 to 15. FIG. 6a shows result comparing purities of HPV16 L1 VLP purified by the T-1 and T5 methods. To analyze the purity of VLPs, a purification experiment was independently performed twice, and results were presented in panel A and panel B. T-1 HPV16 L1 VLP and T-5 HPV16 L1 VLP were loaded at 500 ng, 250 ng, 125 ng, and 62 ng per well after the quantification of the proteins, and after fractionation of that from SDS-PAGE, the result thereof was visualized by staining. From two VLPs, a high purities of a 55 kDa L1 bands were observed. However, it was seen that an intensity of the L1 band of T-5 HPV 16 VLP was higher than that of T-1 HPV 16 VLP. FIG. 6b shows values of two experiments conducted in FIG. 6a, which were represented as mean±standard deviation. To yield a result, an intensity of L1 band of T-5 HPV 16 VLP loaded at 500 ng was set to 100%. According to the results, it was confirmed that the purity of T-5 HPV16 L1 VLPs was higher than that of T-1 HPV16 L1 VLPs.

For the electron microscopy, DLS and analysis of monoclonal antibody reactivity that will be described below, an L1 amount of T-1 HPV 16 VLP was adjusted to be the same as that of T-5 HPV16 VLP. FIG. 7 shows an SDS-PAGE result of L1 amounts of two types of VLPs, which were adjusted to be the same.

4. Electron Microscopy of HPV16 L1 VLPs Separated by T-1 and T5 Purification Methods FIG. 8 shows results of electron microscopy for T-1 HPV 16 VLPs and T-5 HPV 16 VLPs. It was confirmed that a size of the T-5 HPV16 L1 VLP ranges from 40 to 65 nm, and a size of the T-1 HPV16 L1 VLP ranges from 20 to 50 nm. Accordingly, a type of the HPV16 L1 VLP purified by the T-5 method had characteristics different from those of a type of the HPV16 L1 VLP purified by the T-1 method. It was known that a size of an HPV virion naturally occurring was 50 to 60 nm [29,30]. Such a result denotes that the size of the T-5 HPV 16 VLP is closer to an original HPV size.

5. DLS Analysis for HPV16 L1 VLPs Separated by T-1 and T-5 Methods

DLS is widely used to investigate a state of VLPs present in a solution [31]. FIG. 9 shows a representative result of analyzing purified T-1 HPV16 L1 VLPs and T-5 HPV 16 L1 VLPs using a DLS-700 system. FIG. 10 shows a representative result of analyzing HPV16 L1 VLPs using an ELS-Z2 system. VLP size was represented as mean±standard deviation. In FIG. 9, the T-1 HPV16 L1 VLPs were distributed between 29 and 438 nm, and T-5 HPV16 L1 VLPs were distributed between 17 to 233 nm. Accordingly, hydrostatic distributions according to sizes of two types of VLPs were different from each other. FIG. 10A shows intensity profiles of DLS of the two VLPs. FIG. 10B shows polydispersity indexes (P.I.) of the two types of VLPs. In FIG. 10B, like in FIG. 10A, it was confirmed that T-1 HPV16 L1 VLPs had a wider range of size distribution than T-5 HPV16 L1 VLPs does. It was confirmed that the P.I. of the T-5 HPV16 L1 VLPs was lower than that of the T-1 HPV16 L1 VLPs (FIG. 10B). As a result, it was confirmed that the T-5 HPV16 L1 VLPs were present in a uniform type in a solution, compared to the T-1 HPV16 L1 VLPs.

6. Analysis of Monoclonal Antibody Reactivity Towards HPV16 L1 VLPs Purified by T-1 and T-5 Methods Reactivity of an anti-HPV 16 L1 monoclonal antibody to HPV 16 VLP is used as an important criterion to evaluate structural superiority of HPV16 L1 VLPs and ability of those to induce the neutralizing antibodies [26, 32-34]. Reactivity of T-1 HPV16 L1 VLPs and T-5 HPV16 L1 VLPs against the monoclonal antibodies were compared using antibodies H16.V5 and H16.E70 which the most generally used to evaluate these properties [26]. An increase in reactivity to the two antibodies is closely related with an increase in immunogenicity [26, 36]. As shown in FIG. 11, it was confirmed that the reactivity of T-5 HPV16 VLPs against two types of antibodies are significantly higher than those of T-1 HPV16 VLPs.

7. Comparison of Immunogenicity of HPV16 L1 VLPs Purified by T-1 and T-5 Methods It was confirmed that a purity of L1 proteins of T-1 HPV16 L1 VLP is lower than that of T-5 HPV16 L1 VLP (FIG. 6a, FIG. 6b). To immunize two HPV16 L1 VLPs at the same amount, the amount of T-1 HPV16 L1 VLP was adjusted to that of T-5 HPV16 L1 VLPs, and the amounts of L1 proteins were evaluated by SDS-PAGE (FIG. 7). For an immunization, 1 ng of HPV16 L1 VLP was injected in combination with aluminum hydroxide. The 1 ng of protein amount (the value obtained from Bradford protein assay) quantified from T-5 HPV16 L1 VLPs was set as a standard. The HPV16 L1 VLPs purified by the T-1 or T-5 purification methods was subcutaneously injected into mice four times at two weeks intervals. Titers of anti-HPV16 L1 IgG in sera detected after third and fourth immunizations are shown in FIG. 12. After the third immunization, the T-5 HPV16 L1 VLP-immunized group had a median value of 450, whereas the T-1 HPV16 L1 VLP-immunized group had a median value of 0. After the fourth immunization, the T-5 HPV16 L1 VLP-immunized group had a median value of 4050, whereas the T-1 HPV16 L1 VLP-immunized group had a median value of 300. Accordingly, it was confirmed that the T-5 HPV16 L1 VLPs induced 10 times or more than 10 times higher level of anti-HPV16 L1 IgG antibody titer than T-1 HPV16 L1 VLPs did.

After the fourth immunization, an anti-HPV16 neutralizing antibody activities in a mouse sera were detected (FIG. 13). A T-5 HPV16 L1 VLP-immunized group had a neutralizing activity (median value) of 78% while a T-1 HPV16 L1 VLP-immunized group had a neutralizing activity of 33%. Between the two groups, the neutralizing activity showed a significant difference.

8. Investigation of Effect of Heating/Chilling after Treatment with Reducing Agent (Comparison in Conditions for Non-Treatment, β-ME Treatment and Heating & Chilling after β-ME Treatment)

As noted from the above results, high purity of L1 proteins could be obtained by the first heparin chromatography. To specifically investigate an effect of heating/chilling after treatment with a reducing agent on the purity of L1 proteins, two types of experiments were performed. In the first experiment, purities of L1 proteins after the heparin chromatography in a non-treatment, when only a reducing agent was treated (β-ME treatment method), and when heating/chilling was performed after treatment with a reducing agent (T-5 purification method, β-ME+heating & chilling) were compared. In the second experiment, purities of L1 proteins after the heparin chromatography in a non-treatment, when only heating/chilling was performed (heating & chilling method), and when heating/chilling was performed after treatment with a reducing agent (T-5, β-ME+heating & chilling) were compared.

Tables 1 and 2 show a protein amount and a rate of removing contaminating proteins of a loading sample in each condition for the heparin chromatography in the first and second experiments, respectively. As shown in Table 1, in the non-treatment and when the reducing agent was treated, 24 to 25% of proteins were removed before the heparin chromatography, but when heating/chilling was performed after treatment with a reducing agent, 66% of proteins were removed. In Table 2, likewise, in the non-treatment and when the reducing agent was treated, 34 to 40% of proteins were removed before the heparin chromatography, but when heating/chilling was performed after treatment with a reducing agent, 70% of proteins were removed.

TABLE 1

| Condition | Protein amount in homogenate (mg) | Protein amount in loading sample for first heparin chromatography (mg) | Rate of removing contaminants (%) |
|---|---|---|---|
| Non-treatment | 196 | 147 | 25 |
| β-ME | 196 | 150 | 24 |
| β-ME + heating & chilling | 196 | 67 | 66 |

TABLE 2

| Condition | Protein amount in homogenate (mg) | Protein amount in loading sample for first heparin chromatography (mg) | Rate of removing contaminants (%) |
|---|---|---|---|
| Non-treatment | 290 | 172 | 40 |
| heating | 290 | 193 | 34 |
| β-ME + heating & chilling | 290 | 89 | 70 |

FIG. 14 shows SDS-PAGE and Western blots of fractions obtained after the first heparin chromatography when loaded at the same volumes (5 μL, 2.5 μL, 1.2 μL). It was confirmed that in the non-treatment, the amount of obtained L1 proteins was considerably decreased. It was also confirmed that since many foreign proteins were included in the recovered solution, purity was also very low. It was confirmed that, when only a reducing agent, that is, β-ME, was treated, the amount of recovered L1 proteins was increased, but due to a large amount of contaminating proteins in the harvested solution, a purity was not high, either. Meanwhile, when a reducing agent, β-ME, was treated, and heating/chilling was performed, the L1 protein was identified as a major band in SDS-PAGE and Western blotting, and thus a recovery rate, as well as the purity, of the L1 proteins was also high.

To compare the purities of the L1 proteins obtained in the above conditions, proteins in the harvested solution were quantified, and loaded at the same amounts (1 μg, 0.5 μg, 0.25 μg) to confirm by SDS-PAGE and Western blotting (FIG. 15). As seen from the results, the purity of the L1 protein was the highest when heating/chilling was performed after β-ME addition.

FIG. 16 shows SDS-PAGE results of elution fractions obtained from the first heparin chromatography in a non-treatment, when only heating/chilling was performed (heating & chilling method), and when heating/chilling was performed after treatment with a reducing agent (T-5, β-ME+heating & chilling). Fractions collected after the first heparin chromatography were loaded at the same volumes (5 μL, 2.5 μL, 1.2 μL), and analyzed by SDS-PAGE and Western blotting. As a result, in the non-treatment and when only heating/chilling was performed, amounts of recovered L1 proteins were considerably decreased. In addition, due to large amounts of contaminating proteins in the collected solution, the purity was also very low. Meanwhile, when heating/chilling was performed after treatment with a reducing agent, the L1 protein was confirmed as a major band in SDS-PAGE and Western blot, and thus a recovery rate, as well as the purity, of the L1 proteins was also high.

As a result, when only a reducing agent was treated, or when only heating and chilling were performed, a high purity of the L1 proteins could not be obtained, and to purify the L1 proteins with high purity, it was confirmed that heating/chilling after treatment with a reducing agent is essential.

9. Investigation of Effect on Heating/Chilling after Treatment with Reducing Agent (Comparison of Ammonium Sulfate Precipitation, β-ME Treatment, Heating & Chilling after β-ME Treatment)

A purification process using ammonium sulfate precipitation is shown in FIG. 17. A purification method by ammonium sulfate precipitation is designed by replacing the heating & chilling step after β-ME treatment in the T-5 purification method with ammonium sulfate precipitation, and is distinguished from the T-1 purification method shown in FIG. 1. The method by β-ME treatment (β-ME method) is the same as described in the above example. Proteins eluted from first chromatography were loaded at the same volumes (10, 5, 2.5 μL), and analyzed by SDS-PAGE and Western blotting (FIG. 18 and FIG. 19). When heating & chilling was performed after β-ME treatment, L1 proteins had an excellent purity, in the ammonium sulfate precipitation and the method by only β-ME treatment, L1 proteins had low purity (FIG. 18). According to the first chromatography results obtained by the ammonium sulfate precipitation and the method of heating/chilling after β-ME treatment, it was confirmed that when heating/chilling was performed after β-ME treatment, all L1 proteins in the loading sample (LS) were bound to the column, and when ammonium sulfate precipitation was used, a part of L1 proteins in the loading sample (LS) did not bind to the column, and flowed through (FT) (FIG. 19).

10. Investigation of Effect of Heating/Chilling after Treatment with Reducing Agent (Comparison of SEC, Ammonium Sulfate Precipitation and Heating & Chilling after β-ME Treatment)

A size-exclusion chromatography (SEC) process is shown in FIG. 17. The SEC method was based on a conventionally known method [20]. The ammonium sulfate precipitation was the same as described above. A representative SEC result is shown in FIG. 20. HPV16 L1 proteins after SEC were eluted with high purity in fractions 3 to 9, and the fractions were used to compare the purity of L1 proteins by first chromatography (FIG. 21). Purities of L1 proteins in first chromatography elution fractions by SEC, ammonium sulfate precipitation, and heating/chilling after β-ME treatment (β-ME+heating & chilling) were compared (FIG. 21). An elution fraction obtained by each method was adjusted to the same volume (7 ml), and a sample having the same volume (0.35, 0.17, or 0.08 μL) was loaded for SDS-PAGE and Western blotting. It was confirmed that one of the first chromatography elution fractions, which was obtained by heating/chilling after β-ME treatment had the highest purity of L1 proteins.

FIG. 22 shows SDS-PAGE and Western blotting results for the elution fractions of second chromatography which were performed using elution fraction of first chromatography presented in FIG. 21. Elution fraction of each condition in second chromatography was loaded at the same volume (2, 1, or 0.5 μL). According to the analysis of the elution fractions of second chromatography, it was confirmed that when heating/chilling was performed after β-ME treatment, the yield of the L1 proteins was the highest.

To analyze antigenicity of HPV16 L1 VLPs purified in each condition, reactivity of HPV16 neutralizing monoclonal antibody, H16.E70, was compared by ELISA (FIG. 23b). To coat the same amount of HPV16 L1 VLPs, the concentrations of HPV16 L1 VLPs purified by the SEC-based purification method and the ammonium sulfate precipitation method were adjusted to the concentration of HPV16 L1 VLPs purified by heating/chilling after β-ME treatment (T-5 HPV16 L1 VLP) before antigen coating. After the concentration adjustment, it was confirmed by SDS-PAGE and Western blotting that there was no difference in amount of L1 proteins between three types of VLPs (FIG. 23a). As the result of analysis of reactivity to the HPV16 neutralizing monoclonal antibody H16.E70, it was seen that HPV16 L1 VLPs purified by heating/chilling after β-ME treatment (T-5) had the best reactivity (FIG. 23b).

In conclusion, it appears that VLPs yielded by the method conducted by heating/chilling after β-ME treatment has a higher purity than those purified by a conventionally known method such as SEC and ammonium sulfate precipitation, and that has an excellent antigenic characteristic.

11. Comparison of Immunogenicity of HPV16 L1 VLPs Purified by SEC, Ammonium Sulfate Precipitation and Heating/Chilling after Treatment with Reducing Agent (T-5)

1 ng each of the three types of HPV16 L1 VLPs finally purified in FIG. 23 was used for immunization. Before immunization, as shown in FIG. 23A, VLPs was adjusted to have the same concentrations. In the immunization of mice, 1 ng of VLP was injected in combination with 200 μg of aluminum hydroxide. Immunization was performed four times at two week intervals. As the result of measuring neutralizing activity in serum of a mouse immunized four times, in the group immunized with HPV16 L1 VLPs purified by the SEC-based method, the neutralizing activity was 16%, and in the group immunized with HPV16 L1 VLPs purified by the ammonium sulfate precipitation, the neutralizing activity was 28%. Meanwhile, in the group immunized with HPV16 L1 VLPs purified by the method based on heating/chilling after treatment with a reducing agent (T-5), the neutralizing activity was 50%. Consequently, HPV16 L1 VLPs purified by the T-5 method had a higher immunogenicity than HPV16 L1 VLPs purified by a known method.

12. Analysis of Effect as a Function of Heating Temperature after Treatment with Reducing Agent FIGS. 25 and 26 show an effect of removing contaminating proteins according to a heating temperature after treatment with a reducing agent in the purification of HPV16 L1 VLPs and HPV18 L1 VLPs. The homogenate was treated with β-ME, and reacted at room temperature (starting), 25, 30, 35, 40, 45, 50, 55, 60, or 65° C. for 15 minutes. Afterward, the sample was left on ice for 1 hour, and centrifuged at 12000×g to remove precipitated contaminants. A concentration of proteins in the sample resulting from which precipitated contaminants were removed was measured and shown in Panel A. Each sample was loaded at the same volume, and the results analyzed by SDS-PAGE were presented in Panel B. Each sample was loaded at the same volume, and an amount of L1 proteins was detected by Western blotting and presented in Panel C. After the concentration of proteins in each sample was measured, the same amount of proteins was loaded, and an amount of L1 proteins was detected by Western blotting, and shown in Panel D. Accordingly, the Western blotting results shown in Panel D indicates the purity of L1 proteins.

It is apparent that a removing rate of contaminating proteins according to heating was highly increased at 35° C. or more (FIGS. 25A, 25B, 26A, and 26B). As shown in FIGS. 25C and 26C, it was confirmed that HPV16 L1 proteins remained in the homogenate at a heating temperature of 65° C. and 60° C., and HPV18 L1 proteins remained in the homogenate at a heating temperature of 60° C. According to the analysis of the purity of L1 proteins by temperatures, the purity of the HPV16 L1 proteins was high at temperature ranging 35 to 50° C. (FIG. 25D), and the purity of the HPV18 L1 proteins was the highest at temperature ranging 45 to 60° C. (FIG. 26D). Accordingly, when the homogenate was heated at 35 to 60° C., contaminating proteins were removed, while the L1 proteins maintained the stability. The thermal stability of the L1 protein can facilitate separation of the L1 proteins from the contaminating proteins by the heating step under the condition of treating with reducing agents.

13. Analysis of Chilling Effect in the Operation of Heating/Chilling after Treatment with Reducing Agent FIG. 27 shows comparison results between the condition in which only heating was performed after treatment with a reducing agent (heating) and the condition in which chilling was performed after heating (heating & chilling). In FIG. 27, Panel A shows concentrations of proteins measured when only heating was performed, and when chilling was performed after heating. Panels B and C showed Western blotting results obtained when only heating was performed at 45° C. and 50° C., and when chilling was performed after heating (heating and chilling). For Western blotting, a sample for each condition was loaded at the same volumes (5, 2.5 and 1.25 μl). As shown in Panel A, it was confirmed that a total amount of proteins was reduced when chilling was performed after heating, compared to when only heating was performed. Meanwhile, it was confirmed that the amount of L1 proteins was not decreased (FIGS. 27B and 27C). Such results show that the purity of L1 proteins was increased by the chilling.

FIG. 28 shows SDS-PAGE and Western blotting results when only heating was performed after treatment with a reducing agent (H) and when chilling was performed after heating (HC). For accurate analysis, each sample was loaded at 2.5 μl and 1.25 μl. Band intensities of contaminating proteins, protein 1, protein 2 and protein 3, were high when only heating was performed, whereas band intensities of the contaminating proteins, protein 1, protein 2 and protein 3, were decreased when chilling was performed after heating (FIG. 28). Meanwhile, it seems that an amount of L1 proteins was not decreased by the chilling (Western blotting results in FIG. 28). FIG. 29 shows band intensities of contaminating proteins, protein 1, protein 2, and protein 3, which were detected by SDS-PAGE, when only heating was performed (H only) and when chilling was performed after heating (HC).

14. Purification of HPV16 L1 VLPs and HPV18 L1 VLPs According to Thermal Treatment at 60° C.

Homogenates of yeast cells expressing HPV16 L1 and HPV18 L1 were treated with a reducing agent, heated at 60° C., and chilled to attempt to perform VLP purification. The panel A in FIG. 30 shows SDS-PAGE analysis results for first chromatography. LS and FT indicate a loading sample and a flow-through, respectively. Elution indicates a fraction formed by L1 proteins eluted. Panel B shows SDS-PAGE analysis results for the final product of second chromatography. Each type of L1 proteins was purified with high purity. Panel C shows transmission electron microscopy results for the final purification product. It was confirmed that VLPs were formed after L1 proteins were purified after being heated at 60° C.

15. Purification of HPV18 L1 VLPs by T-5 Method

FIG. 31 shows SDS-PAGE results for first chromatography when HPV18 L1 VLPs were purified by a T-5 method. Cell homogenate was treated with a reducing agent before first heparin chromatography, heated at 45° C., and chilled on ice. FIG. 31 shows that contaminating proteins were effectively removed by the first heparin chromatography. FIG. 32 shows SDS-PAGE results for second cation-exchange chromatography. In second chromatography, the contaminating substances were eluted from fractions including 0.6 M and 0.7 M NaCl, and L1 proteins were eluted from fractions including 0.9 M and 1 M NaCl. Accordingly, it was confirmed that HPV18 L1 proteins were purified with high purity by a T-5 method. FIG. 33 shows dynamic light scattering (DLS) results for finally purified T-5 HPV18 L1 VLPs.

16. Purification of HPV58 L1 VLPs by T-5 Method

FIG. 34A shows SDS-PAGE results for HPV58 L1 fractions separated by a first chromatography according to the T-5 method. According to the first chromatography, a HPV58 L1 protein was detected as a major band. FIG. 34B shows SDS-PAGE results for HPV58 L1 VLPs separated by second chromatography. The HPV58 L1 proteins were eluted from all of fractions including 0.6 M, 0.7 M, 0.8 M, 0.9 M, and 1 M NaCl. FIG. 35 shows SDS-PAGE and Western blotting results for HPV58 L1 VLPs finally purified by the T-5 method. According to the T-5 method, it was confirmed that HPV58 L1 VLPs were purified with high purity.

While the invention has been shown and described with reference to certain exemplary embodiments thereof, it will be clearly understood by those skilled in the art that such detailed descriptions are merely exemplary embodiments, but the scope of the invention is not limited thereto. Therefore, it will be understood that an actual scope of the invention is defined by the accompanying claims and equivalents thereof.

INDUSTRIAL APPLICABILITY

The present invention relates to a method of purifying HPV L1 proteins with high purity and high efficiency. According to the purification method of the present invention, a purification purity of HPV L1 proteins can be considerably increased, and VLPs of the purified HPV L1 protein form a structure more similar to that of a native HPV virion, and thus have very excellent immunogenicity.

REFERENCES

1. Woodman C B, Collins S I, Young L S (2007) The natural history of cervical HPV infection: unresolved issues. Nat Rev Cancer 7: 11-22.
2. National Cancer Institute (2007) Women's Health Report, Fiscal Years 2005-2006. NCI Women's Health Report FY2005-2006.
3. Burk R D, Chen Z G, Van Doorslaer K (2009) Human Papillomaviruses: Genetic Basis of Carcinogenicity. Public Health Genomics 12: 281-290.
4. de Villiers E M, Fauquet C, Broker T R, Bernard H U, zur Hausen H (2004) Classification of papillomaviruses. Virology 324: 17-27.
5. Clifford G, Franceschi S, Diaz M, Munoz N, Villa L L (2006) Chapter 3: HPV type-distribution in women with and without cervical neoplastic diseases. Vaccine 24 Suppl 3: S3/26-34.
6. Conway M J, Meyers C (2009) Replication and assembly of human papillomaviruses. J Dent Res 88: 307-317.
7. Kim S N, Jeong H S, Park S N, Kim H-J (2007) Purification and immunogenicity study of human papillomavirus type 16 L1 protein in *Saccharomyces cerevisiae*. J Virol Methods 139: 24-30.
8. Li M, Cripe T P, Estes P A, Lyon M K, Rose R C, et al. (1997) Expression of the human papillomavirus type 11 L1 capsid protein in *Escherichia coli*: characterization of protein domains involved in DNA binding and capsid assembly. J Virol 71: 2988-2995.
9. Hanumantha Rao N, Baji Babu P, Rajendra L, Sriraman R, Pang Y Y, et al. (2011) Expression of codon optimized major capsid protein (L1) of human papillomavirus type 16 and 18 in *Pichia pastoris*; purification and characterization of the virus-like particles. Vaccine 29: 7326-7334.
10. Aires K A, Cianciarullo A M, Carneiro S M, Villa L L, Boccardo E, et al. (2006) Production of human papillomavirus type 16 L1 virus-like particles by recombinant *Lactobacillus casei* cells. Appl Environ Microbiol 72: 745-752.
11. Baek J O, Seo J W, Kim I H, Kim C H (2011) Production and purification of human papillomavirus type 33 L1 virus-like particles from *Spodoptera frugiperda* 9 cells using two-step column chromatography. Protein Expr Purif 75: 211-217.
12. Maclean J, Koekemoer M, Olivier A J, Stewart D, Hitzeroth, I I, et al. (2007) Optimization of human papillomavirus type 16 (HPV-16) L1 expression in plants: comparison of the suitability of different HPV-16 L1 gene variants and different cell-compartment localization. J Gen Virol 88: 1460-1469.
13. Garland S M, Smith J S (2010) Human papillomavirus vaccines: current status and future prospects. Drugs 70: 1079-1098.
14. Madrid-Marina V, Torres-Poveda K, Lopez-Toledo G, Garcia-Carranca A (2009) Advantages and disadvantages of current prophylactic vaccines against HPV. Arch Med Res 40: 471-477.
15. National Cancer Institute Human Papillomavirus (HPV) Vaccines, http colon forward slash forward slash www dot cancer dot gov forward slash cancertopics forward slash factsheet forward slash prevention forward slash HPV-vaccine.
16. Mukhopadhyay P, Paul B (2009) Introducing HPV Vaccine in Developing Countries—Addressing the Challenge. Indian J Community Med 34: 370-371.
17. Walsh G (2010) Biopharmaceutical benchmarks 2010. Nat Biotechnol 28: 917-924.
18. Vicente T, Roldao A, Peixoto C, Carrondo M J, Alves P M (2011) Large-scale production and purification of VLP-based vaccines. J Invertebr Pathol 107 Suppl: S42-48.
19. Hofmann K J, Cook J C, Joyce J G, Brown D R, Schultz L D, et al. (1995) Sequence determination of human papillomavirus type 6a and assembly of virus-like particles in *Saccharomyces cerevisiae*. Virology 209: 506-518.
20. Park M A, Kim H J, Kim H-J (2008) Optimum conditions for production and purification of human papillomavirus type 16 L1 protein from *Saccharomyces cerevisiae*. Protein Expr Purif 59: 175-181.
21. Cook J C (2003) Process for purifying human papillomavirus virus-like particles. Merck & Co., Inc.
22. Kim H J, Kim S Y, Lim S J, Kim J Y, Lee S J, et al. (2010) One-step chromatographic purification of human papillomavirus type 16 L1 protein from *Saccharomyces cerevisiae*. Protein Expr Purif 70: 68-74.
23. Kim H J, Lee S J, Kim H-J (2010) Optimizing the secondary structure of human papillomavirus type 16 L1 mRNA enhances L1 protein expression in *Saccharomyces cerevisiae*. J Biotechnol 150: 31-36.
24. Kim H J, Lim S J, Kim J Y, Kim S Y, Kim H-J (2009) A method for removing contaminating protein during purification of human papillomavirus type 18 L1 protein from *Saccharomyces cerevisiae*. Arch Pharm Res 32: 1759-1766.
25. Kim H J, Kwag H L, Jin Y, Kim H-J (2011) The composition of the carbon source and the time of cell harvest are critical determinants of the final yield of human papillomavirus type 16 L1 protein produced in *Saccharomyces cerevisiae*. Protein Expr Purif 80: 52-60.
26. Kim H J, Lim S J, Kwag H L, Kim H-J (2012) The choice of resin-bound ligand affects the structure and immunogenicity of column-purified human papillomavirus type 16 virus-like particles. PLoS One 7: e35893.
27. Jin Y, Kim H J, Yim G W, Tae Kim Y, Chang D Y, et al. (2012) A single serum dilution enzyme-linked immunosorbent assay for determining anti-human papillomavirus (HPV) antibody titres in humans immunised with prophylactic HPV vaccines. J Pharm Biomed Anal 66: 352-355.
28. Han J E, Wui S R, Park S A, Lee N G, Kim K S, et al. (2012) Comparison of the immune responses to the CIA06-adjuvanted human papillomavirus L1 VLP vaccine with those against the licensed HPV vaccine Cervarix in mice. Vaccine 30: 4127-4134.
29. Hagensee M E, Olson N H, Baker T S, Galloway D A (1994) Three-dimensional structure of vaccinia virus-produced human papillomavirus type 1 capsids. J Virol 68: 4503-4505.

30. Baker T S, Newcomb W W, Olson N H, Cowsert L M, Olson C, et al. (1991) Structures of bovine and human papillomaviruses. Analysis by cryoelectron microscopy and three-dimensional image reconstruction. Biophys J 60: 1445-1456.
31. Shi L, Sanyal G, Ni A, Luo Z, Doshna S, et al. (2005) Stabilization of human papillomavirus virus-like particles by non-ionic surfactants. J Pharm Sci 94: 1538-1551.
32. Ryding J, Dahlberg L, Wallen-Ohman M, Dillner J (2007) Deletion of a major neutralizing epitope of human papillomavirus type 16 virus-like particles. J Gen Virol 88: 792-802.
33. Culp T D, Spatz C M, Reed C A, Christensen N D (2007) Binding and neutralization efficiencies of monoclonal antibodies, Fab fragments, and scFv specific for L1 epitopes on the capsid of infectious HPV particles. Virology 361: 435-446.
34. White W I, Wilson S D, Palmer-Hill F J, Woods R M, Ghim S J, et al. (1999) Characterization of a major neutralizing epitope on human papillomavirus type 16 L1. J Virol 73: 4882-4889.
35. Laemmli U K (1970) Cleavage of structural proteins during the assembly of the head of bacteriophage T4. Nature 227: 680-685.
36. Chang D Y, Kim H J, Kim H-J (2012) Effects of downstream processing on structural integrity and immunogenicity in the manufacture of papillomavirus type 16 L1 virus-like particles, Biotechnol Bioprocess Eng 17: 755-763.

The invention claimed is:

1. A method of purifying human papillomavirus (HPV) L1 proteins, comprising the steps of:
   (i) culturing transformed host cells expressing an HPV L1 protein, harvesting the cultured host cells and disrupting the host cells;
   (ii) adding a reducing agent to a homogenate of the host cells;
   (iii) heating and chilling the homogenate of the host cells to which the reducing agent is added;
   (iv) removing precipitated contaminants by centrifugation of the heated and chilled cell homogenate; and
   (v) purifying HPV L1 proteins by performing chromatography on the heated and chilled homogenate of the host cells,
   wherein the chilling is performed at 0 to 10° C.;
   wherein the heating is performed at a temperature higher than 37° C. and equal to or lower than 60° C. for 10 minutes to 12 hours;
   and wherein the chromatography is ion exchange chromatography, heparin chromatography or affinity chromatography.

2. The method according to claim 1, wherein the HPV is selected from the group consisting of HPV type 6a, HPV type 6b, HPV type 11, HPV type 16, HPV type 18, HPV type 30, HPV type 31, HPV type 33, HPV type 35, HPV type 39, HPV type 41, HPV type 42, HPV type 43, HPV type 44, HPV type 45, HPV type 51, HPV type 52, HPV type 54, HPV type 55, HPV type 56, HPV type 58, HPV type 68 and HPV type 70.

3. The method according claim 1, wherein the host cells are bacteria, yeast cells, insect cells, plant cells or animal cells.

4. The method according to claim 3, wherein the yeast cell is *Saccharomyces cerevisiae, Pichia Pastoris*, or *Hansenula polymorpha*.

5. The method according to claim 1, wherein the reducing agent is selected from the group consisting of β-mercaptoethanol, dithiothreitol (DTT), 2-mercaptoethylamine-HCl, tris(2-carboxyethyl)phosphine (TCEP), or cysteine-HCl.

6. The method according to claim 5, wherein β-mercaptoethanol is added to the homogenate of the host cells to have a final concentration of 0.1 wt % or more.

7. The method according to claim 5, wherein DTT is added to the homogenate of the host cells to have a final concentration of 2 mM or more.

8. The method according to claim 1, wherein, in step (iii), the heating is performed at a temperature higher than 37° C. and equal to or lower than 45° C.

9. The method according to claim 1, wherein, in step (iii), the temperature is higher than 45° C. and equal to or lower than 60° C.

10. The method according to claim 9, wherein, in step (iii), the temperature is higher than 45° C. and equal to or lower than 55° C.

* * * * *